US008028928B2

(12) United States Patent
Detweiler et al.

(10) Patent No.: US 8,028,928 B2
(45) Date of Patent: Oct. 4, 2011

(54) SPREADER APPARATUS FOR SAND BASED FORMULATIONS

(75) Inventors: A. Ronald Detweiler, Okemos, MI (US); Nancy M. Dykema, Holt, MI (US); Joseph M. Vargas, Jr., East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 162 days.

(21) Appl. No.: 12/288,193

(22) Filed: Oct. 17, 2008

(65) Prior Publication Data
US 2009/0151243 A1 Jun. 18, 2009

Related U.S. Application Data

(60) Provisional application No. 61/002,898, filed on Nov. 13, 2007.

(51) Int. Cl.
*B05B 17/04* (2006.01)

(52) U.S. Cl. ....... 239/7; 239/214.25; 239/662; 239/663; 239/672; 239/681; 504/261

(58) Field of Classification Search .............. 239/7, 172, 239/214.25, 661, 662, 663, 667, 672, 673, 239/679, 681; 504/261
See application file for complete search history.

(56) References Cited

U.S. PATENT DOCUMENTS

| | | | | |
|---|---|---|---|---|
| 4,886,208 | A * | 12/1989 | Strand | 239/662 |
| 5,860,604 | A * | 1/1999 | Kooiker | 239/672 |
| 6,336,600 | B1 * | 1/2002 | Jessen | 239/663 |
| 7,370,818 | B2 * | 5/2008 | Ward et al. | 239/662 |
| 2004/0077500 | A1 * | 4/2004 | Sakata et al. | 504/261 |
| 2006/0006256 | A1 * | 1/2006 | Smith et al. | 239/672 |

* cited by examiner

*Primary Examiner* — Steven J Ganey
(74) *Attorney, Agent, or Firm* — Melden & Carroll, LLP

(57) ABSTRACT

The present inventions relate to top dressing vehicles for coating, mixing, and dispensing compositions of top dressing materials comprising agriculturally active ingredients (A.I.s). More particularly, these inventions relate to apparatus for spraying liquid formulations comprising active ingredients A.I.s onto top dressing materials prior to and during delivering top dressing applications. Further, these inventions relate to applying liquids comprising A.I.s to top dressing materials at a point-of-application. Even further, these inventions relate to delivering treated top dressing, specifically, to broadcast spreading of top dressing comprising sand and agriculturally active ingredients as moist and dry compositions.

19 Claims, 16 Drawing Sheets
(4 of 16 Drawing Sheet(s) Filed in Color)

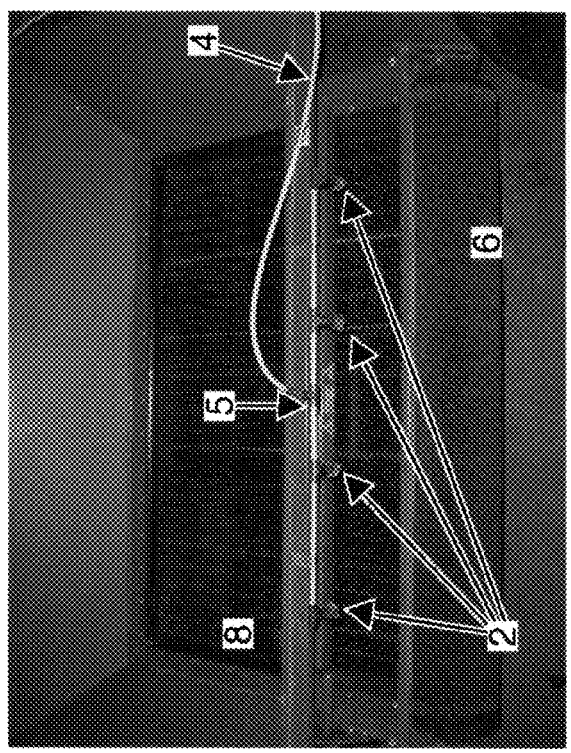
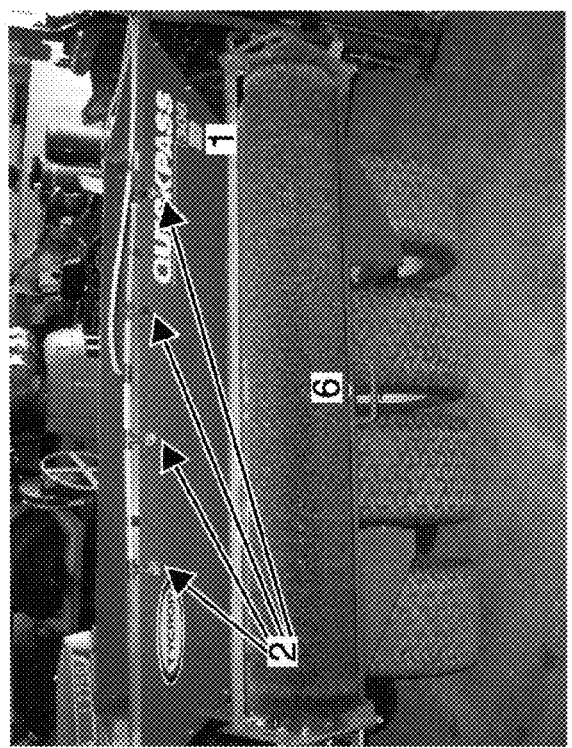
FIG. 5B
FIG. 5A

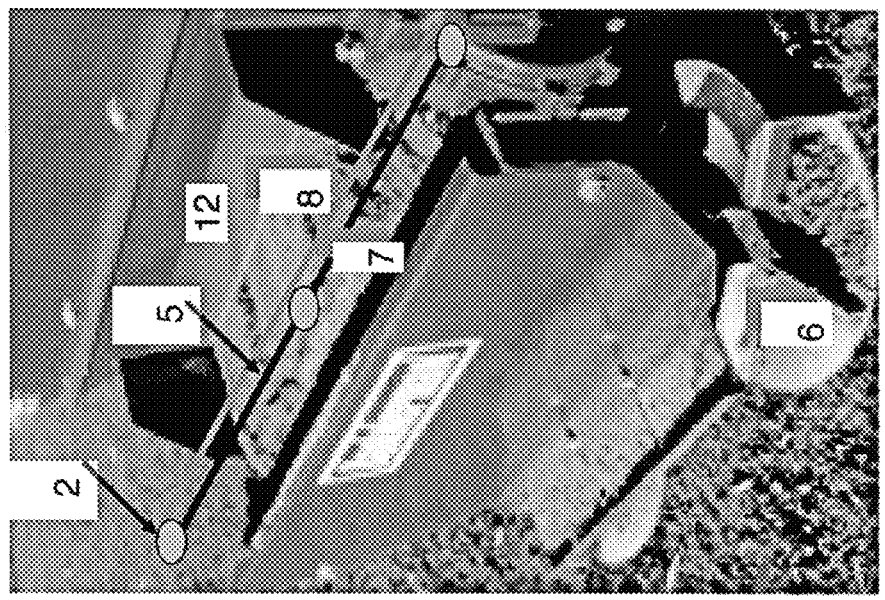
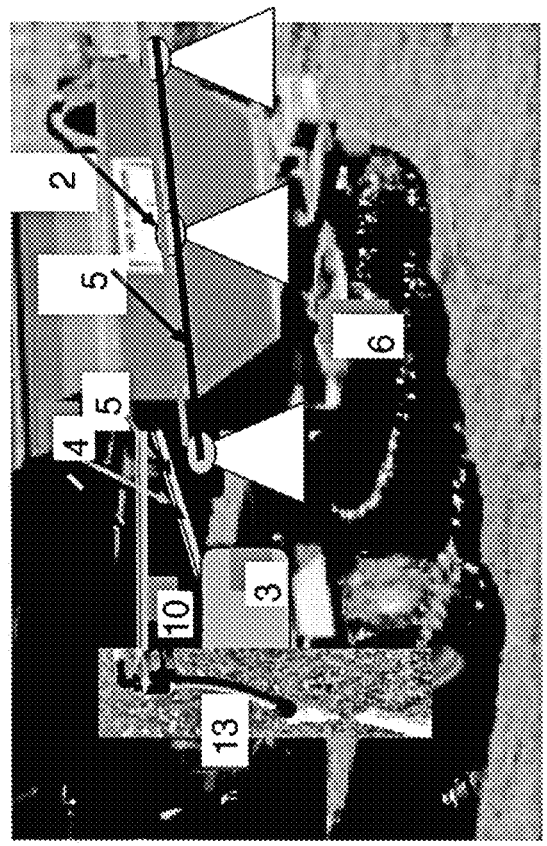
FIG. 7A
FIG. 7B
FIG. 7C

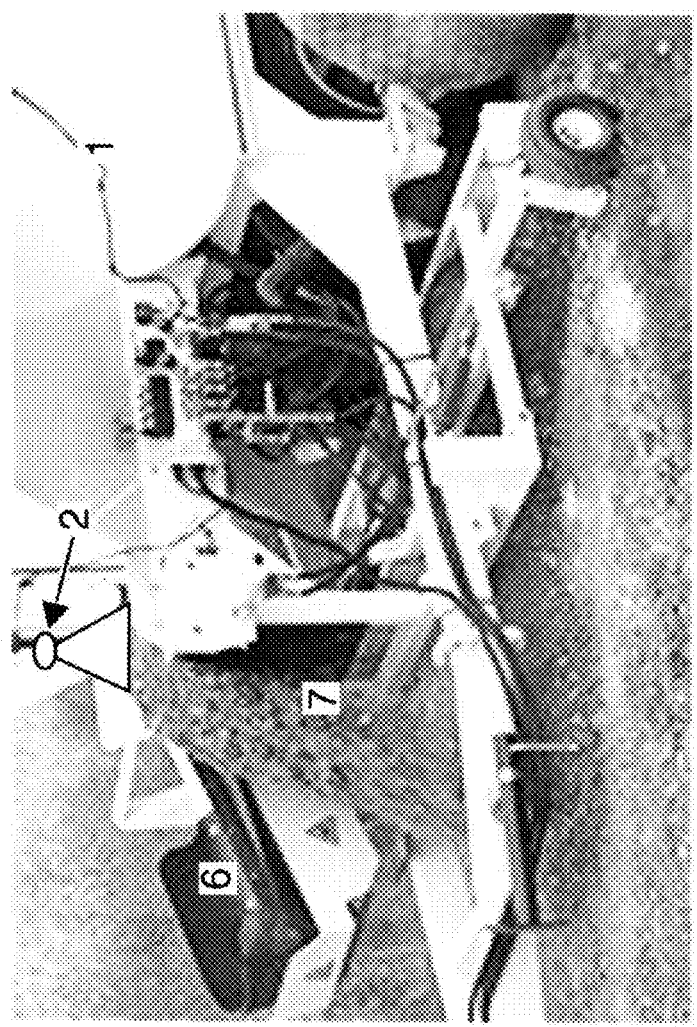
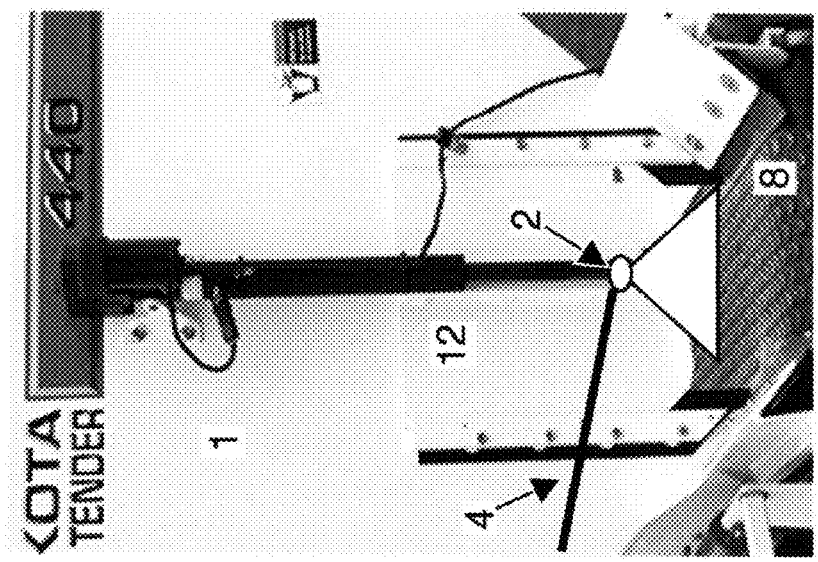
FIG. 11B
FIG. 11A

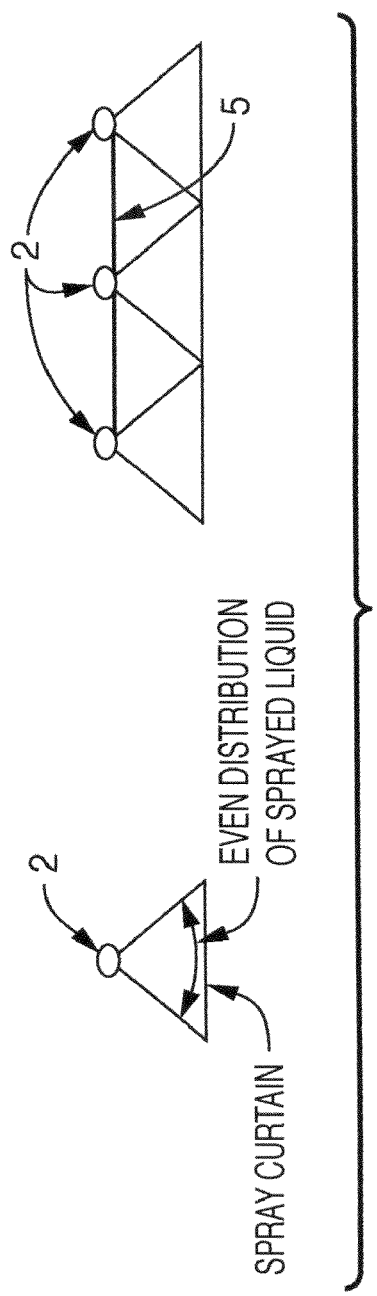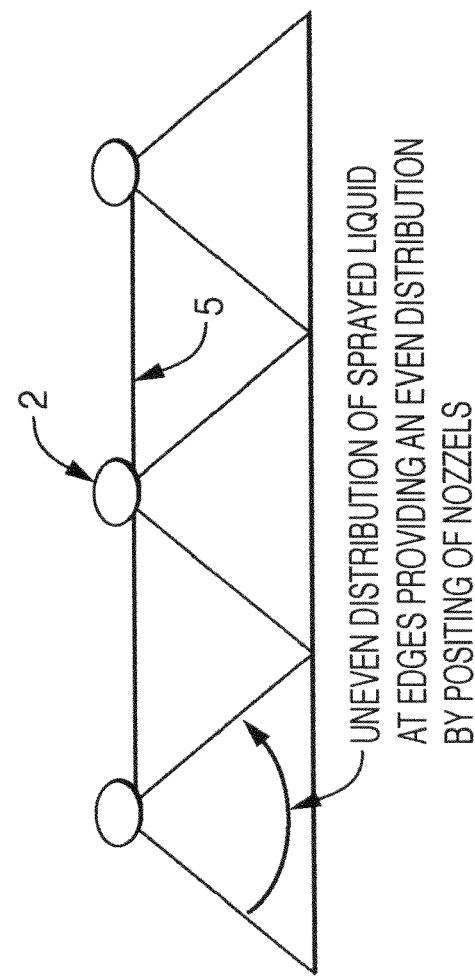

TREATMENT #1

TREATMENT #2

TREATMENT #3

TREATMENT #4

TREATMENT #6

TREATMENT #7

TREATMENT #3

TREATMENT #8

SPREADER APPARATUS FOR SAND BASED FORMULATIONS

This application claims priority to U.S. Provisional Application Ser. No. 61/002,898, filed on Nov. 13, 2007.

FIELD OF THE INVENTION

The present inventions relate to top dressing vehicles for coating, mixing, and dispensing compositions of top dressing materials comprising agriculturally active ingredients (A.I.s). More particularly, these inventions relate to apparatus for spraying liquid formulations comprising active ingredients A.I.s onto top dressing materials prior to and during delivering top dressing applications. Further, these inventions relate to applying liquids comprising A.I.s to top dressing materials at a point-of-application. Even further, these inventions relate to delivering treated top dressing, specifically, to broadcast spreading of top dressing comprising sand and agriculturally active ingredients as moist and dry compositions.

BACKGROUND

Golf turf grass requires extensive cultivation to maintain optimal play quality. Normal machine operations such as top dressing and pesticide or fertilizer applications are disruptive to play and produce soil compaction and turf wear, which reduces overall turf quality. Because these separate operations generally must be performed during the day when golfers are present, equipment which makes it possible to combine two or three maintenance tasks into one operation should reduce the disruption of play, reduce turf wear and compaction, save time and labor expense, and allow for more rounds of golf to be played each day.

Current top dressing spreaders are a drop-type with finished brushes and a spinner-type. These types are used to apply wet or dry sand, and other materials, including other types of top dressing materials onto turf on golf courses, lawns, athletic fields, parks, and other recreational areas as part of a normal maintenance program. Both types of machines, especially the drop-type, are capable of applying wet or dry top dressing materials (generally sand) at fairly uniform thickness to turfs. However, these machines are heavy and produce undesirable turf compaction. The drop-type topdresser machines (topdressers) are slow and apply bands of sand merely as wide as the conveying belt that carries the sand to the dispenser. These types of machines in general range from 3 up to at least 6 feet in width. Thus the use of drop-type topdressers requires many passes over a large area in order to provide desired coverage with a top dressing material (top dressed area). The spinner-type topdressers spread material over much wider swaths (in general up to at least 40 feet in width), but spinner type machines are much heavier than the smaller topdressers. In general, the extra weight produces even greater turf damage and less uniform applications than drop-type top dressing machines.

Sprayer units are used for applying turf products to recreational turf (turf areas primarily used for recreation), especially golf course turf, and is part of a normal maintenance program. This practice generally occurs on a 14-day schedule throughout the growing season when disease, insect and weed pests are active. Sprayer units may be self-propelled or carried on other vehicles, and capable of spraying swaths up to 18 feet wide with the desired fungicides, insecticides, herbicides, soluble fertilizer, soil wetting agents, plant growth regulators and hormones, et cetera. However the weight of sprayer units produced turf compaction and interfered with play. Further, they produce a large amount of spray drift to non-target areas in addition to providing a health hazard by exposing the people applying the spray and the golfers to wet spray residues through inhalation, skin and clothing contact.

SUMMARY OF THE INVENTION

The present inventions relate to top dressing vehicles for coating, mixing, and dispensing compositions of top dressing materials comprising agriculturally active ingredients (A.I.s). More particularly, these inventions relate to apparatus for spraying liquid formulations comprising active ingredients A.I.s onto top dressing materials prior to and during delivering top dressing applications. Further, these inventions relate to applying liquids comprising A.I.s to top dressing materials at a point-of-application. Even further, these inventions relate to delivering treated top dressing, specifically, to broadcast spreading of top dressing comprising sand and agriculturally active ingredients as moist and dry compositions.

The present invention provides a top dressing vehicle comprising, a dispensing unit, a conveying means and a sprayer. In one embodiment, said dispensing unit is selected from the group including but not limited to a blending device, an elevator device, a drop spreader, a brush spreader, and a spinner spreader. In one embodiment, said top dressing material is deposited onto said conveying means. In one embodiment, said deposited is by gravity. In one embodiment, said sprayer is configured to deliver a spray onto said conveying means. In one embodiment, said spray is a liquid. In one embodiment, said spray provides a spray curtain. In one embodiment, said spray comprises particles. In one embodiment, said spray comprises a mist. In one embodiment, said vehicle is selected from the group including but not limited to a carried vehicle, trailer vehicle, a self-propelled vehicle, and the like. In one embodiment, said conveying means is selected from the group including but not limited to a conveyor systems, conveyor belts, belt conveyors, screw conveyors, augers, feeders, elevators, and the like. In one embodiment, said sprayer is selected from the group including but not limited to an electric, a hydraulic, a $CO_2$ sprayer, and the like. In one embodiment, said sprayer comprises a pump, a regulator valve, a tank, a hose, and a nozzle. It is not meant to limit the location or the number of the attached sprayer parts. Indeed a variety of locations are contemplated for an attached part. Thus, in one embodiment, said nozzle is attached to the vehicle. In one embodiment, said nozzle is attached above the conveying means. In one embodiment, said nozzle is attached to the vehicle at one side of the conveying means. In one embodiment, said top dressing vehicle further comprises a boom. In one embodiment, said nozzle is attached to a boom. In one embodiment, said tank is attached to the vehicle. In one embodiment, said hose is attached to the vehicle. In one embodiment, said nozzle is attached in a position for spraying a liquid in between the conveying means and the dispensing unit. In one embodiment, said nozzle is attached to the dispensing unit. In one embodiment, said sprayer is capable of spraying a liquid as a spray curtain. In one embodiment, said sprayer is configured to deliver a spray onto a top dressing material prior to conveying said material to said dispensing unit. In one embodiment, said dispensing unit is attached to a top dressing machine. In one embodiment, said top dressing machine includes but is not limited to a blender machine, a drop spreading machine, a spinner spreading machine, an elevator machine, and the like. In one embodiment, said vehicle further comprises a flow rate adjuster unit. In one embodiment, said vehicle further comprises a calibration aid.

The present invention also provides a flow rate adjuster unit. In one embodiment, the flow rate adjuster unit controls a regulator valve of a sprayer. In one embodiment, the flow rate adjuster unit controls the flow rate of a nozzle. In one embodiment, the flow rate adjuster unit controls the flow rate of a rotating nozzle. In one embodiment, the flow rate adjuster unit provides automatic control of the speed of the conveyor means. In one embodiment, the flow rate adjuster unit provides automatic control of the speed of the blender means. In one embodiment, the flow rate adjuster unit accepts operator input. In one embodiment, the flow rate adjuster accepts automatic input, including but not limited to input from sensors, such as an axel speed sensor, a level sensor (for sensing inclines and declines), and the like.

The present invention also provides a calibration aid. In one embodiment, the calibration aid is an operator manual. In one embodiment, the calibration aid is a chart. In one embodiment, the calibration aid shows top dressing vehicle settings for delivering specific types of mixtures.

The present invention provides a method for making an apparatus, comprising, a) providing, i) a top dressing vehicle comprising a conveying means and a dispensing unit, ii) a sprayer unit comprising a tank, a pump, a hose, and a nozzle, and ii) b) attaching said nozzle of the sprayer unit to said top dressing vehicle. In one embodiment, the method further comprises attaching the nozzle above the conveying means. In one embodiment, the method further comprises attaching the nozzle at one side of the conveying means. In one embodiment, said top dressing vehicle further comprises a boom. In one embodiment, said nozzle is attached to a boom. In one embodiment, said top dressing vehicle is selected from the group including but not limited to a blender machine, a drop spreading machine, a spinner spreading machine, a broadcast spreader machine, and the like. In one embodiment, the method further comprises a dispensing device. In one embodiment, said dispensing unit is selected from the group including but not limited to a blending device, an elevator, a drop spreader, a brush spreader, a spinner spreader, and the like. In one embodiment, said nozzle is attached in a position for spraying a liquid in between the conveying means and the dispensing unit. In one embodiment, said nozzle is attached to the dispensing unit. In one embodiment, the method further comprises attaching the tank to said top dressing vehicle. In one embodiment, the method further comprises attaching the hose to said top dressing vehicle. In one embodiment, the method further comprises attaching a foam-marking unit to a top dressing vehicle. In one embodiment, the method further comprises attaching a flow rate adjuster unit. In one embodiment, the method further comprises attaching a calibration aid.

The present invention also provides a method for making an apparatus, comprising, a) providing, i) a top dressing vehicle selected from the group including but not limited to a carried vehicle, a trailer vehicle, and a self-propelled vehicle; and ii) a sprayer unit comprising a tank, a pump, a hose, and a nozzle, and b) attaching said nozzle of the sprayer unit to said top dressing vehicle. In one embodiment, the method further comprises attaching the tank to said top dressing vehicle. In one embodiment, the method further comprises attaching the hose to said top dressing vehicle. In one embodiment, the method further comprises attaching a foam-marking unit to a top dressing vehicle. In one embodiment, the method further comprises attaching a flow rate adjuster unit. In one embodiment, the method further comprises attaching a calibration aid.

The present invention provides a method of using a top dressing vehicle, comprising, a) providing, i) a top dressing material, ii) a sprayable formulation, comprising an agriculturally active ingredient for treating a top dressing material, iii) a top dressing vehicle, comprising a conveying means and a sprayer unit, wherein said sprayer unit is capable of spraying the formulation onto a top dressing material, and b) spraying the formulation onto the top dressing material with the sprayer unit of the top dressing vehicle for providing a treated top dressing material. In one embodiment, during the spraying of step b) the top dressing material is moving through the spray. In one embodiment, said agriculturally active ingredient is selected from the group including but not limited to a fungicide, insecticide, herbicide, plant growth regulator, soil wetting agent, fertilizer, plant hormone, plant extract, biological control agent, plant nutrients, and the like. In one embodiment, said sprayer unit is attached to the top dressing vehicle. In one embodiment, said sprayer unit comprises a hand-held sprayer. In one embodiment, said top dressing vehicle further comprises a dispensing unit. In one embodiment, the method further comprises calibrating the dispensing of the top dressing material. In one embodiment, said dispensing unit is selected from the group including but not limited to a blending device, a drop spreader, a brush spreader, a spinner spreader, an elevator, a broadcast spreader, and the like. In one embodiment, said nozzle is attached in a position for spraying a liquid in between the conveying means and the dispensing unit. In one embodiment, said nozzle is capable of spraying a spray curtain. In one embodiment, said treated top dressing continues to move to said dispensing unit. In one embodiment, said top dressing material comprises sand. In one embodiment, the method further comprises calibrating the spraying of the top dressing material. In one embodiment, the method further comprises attaching a flow rate adjuster unit to the wherein the top dressing vehicle. In one embodiment, the method further comprises attaching a calibration aid. In one embodiment, the method further comprises attaching a foam ejector. In one embodiment, the method further comprises attaching a foam-marking unit. In one embodiment, said top dressing material is selected from the group including but not limited to sand, peat, soil, blends and mixtures of sand and peat, sand and soil, peat and soil, sand, soil, and peat, and the like. In one embodiment, said top dressing material is sand.

The present invention provides a composition, comprising a marker and a top dressing material, where said top dressing material comprises an agriculturally active ingredient. In one embodiment, said marker is a color. In one embodiment, said marker is biodegradable.

The present invention provides a method of marking a top dressing material, comprising, a) providing, i) a composition comprising a marker and ii) a top dressing material comprising an agriculturally active ingredient, and b) adding said marker to the top dressing material. In one embodiment, said top dressing material comprises sand. In one embodiment, said top dressing material comprises peat.

DEFINITIONS

To facilitate an understanding of the present invention, a number of terms and phrases as used herein are defined below:

The use of the article "a" or "an" is intended to include one or more.

As used herein, terms defined in the singular are intended to include those terms defined in the plural and vice versa, for example, as used herein, the term "apparatus" refers to a device, such as equipment, designed for a particular use.

Thus, an apparatus may be singular or plural, whereas apparati and apparatuses refer to singular and plural pieces of equipment, respectively.

As used herein, the term "material" or "materials" refers to, in their broadest sense, any composition of matter, such as a top dressing material.

As used herein, the term "point-of-application" refers in general to a turfgrass facility, such as a golf course or Turf farm. For the purposes of the present inventions, a point-of-application may specifically refer to an area of turf, such as a top dressing vehicle of the present inventions providing and delivering a composition of the present inventions directly to an area of turf grass.

As used herein, the term "carrier" refers to one or more substances that act as a vehicle for an agricultural chemical and that is suitable for administration to a plant or soil (i.e., turfgrass plant, putting green, and the like). A "carrier" in general, includes but is not limited to, solid and liquid diluents, hydrotropes, surface-active agents, encapsulating substances, and for the purposes of the present inventions, sand as a carrier for an agriculturally active ingredient. For the purposes of the present inventions, a carrier, such as a sand particle, can be combined with an active compound according to methods described herein. The carrier ingredients discussed above are exemplary and not meant to limit the type of carrier of the present inventions.

As used herein, the term "composition" or "formulation" refers to a composition of matter including at least two substances; for example, a composition may be in the form of a liquid, solid or both, such as a suspension. Moreover, in certain embodiments, the compositions of the present invention may be formulated for horticultural or agricultural use. Such compositions include sprays, mists, powders, dusts, and granules.

For the purposes of the present inventions a "dry formulation" or "dry composition" refers to a composition wherein the A.I. is formulated as a solid, such as a granule, particle, dust, powder and the like. In general, a dry formulation refers to a composition comprising less than 1% water. In some embodiments, a dry composition is moistened prior to use, i.e. distributing onto an area of turf. Alternatively, when the A.I. is formulated as a liquid, mist, gel, suspension, and the like, in a composition or mixture, the composition is a "moist composition" or "moist formulation."

In general, "moist" refers to a composition comprising at least 1% water. In some embodiments, a moist composition is dried prior to use, i.e. distributing onto an area of turf. In some embodiments, such as where a saturated mixture is provided, for example, sand soaked in a bucket of liquid A.I. formulation, a "wet composition" or "wet formulation" is created.

As used herein, "solution" refers to when the molecules of a compound or solute are uniformly mixed with the molecules of the solvent.

As used herein, "soluble" refers to a compound that can be dissolved in water. In reference to a fertilizer, refers to a fertilizer that is made up of easily dissolved components in water that are immediately available for plant use.

As used herein, "suspension" refers to particles of a solid dispersed in a liquid but not dissolved.

As used herein, "diluent" refers to an inert material used in the composition of sprays, for example, water, and dusts, for example, diatomaceous earth, clay, and the like. A diluent is usually combined with an active ingredient to dilute or otherwise make the mixed material more suitable for field application.

As used herein, "emulsifier" or "emulsifying agent" refers to a surface-active material that reduces the separation of droplets of one liquid in another.

As used herein, "wetting agent" refers to a compound that reduces the droplet size and lowers the surface tension of the water, making it wetter.

As used herein, "inert" in reference to an "inert ingredient" refers to a material in a fungicide, pesticide, fertilizer, nutrient, growth regulator, composition that have no activity in creating the desired effect of the product. An inert ingredient may serve as a binding agent or carrier for the active ingredients such that they can be applied efficiently and uniformly.

As used herein, "effective amount" refers to the amount of a substance (e.g., including an active substance) sufficient to effect beneficial or desired results. An effective amount can be administered in one or more administrations, applications or dosages and is not intended to be limited to a particular composition or administration route.

As used herein, the term "top dressing" or "top dressing" or "top dress" in reference to an action refers to a maintenance practice of spreading a material substance over an area of turfgrass, such as a putting green, teeing green (tee box), fairway, sports field, and the like, to level and smooth the surface. It also has the effect of improving drainage, controlling thatch and maintaining biological balance, and maintaining quality of play.

As used herein, the term "top dressing" or "top dressing" or "top dress" in reference to a material or substance refers to a composition comprising inorganic and organic matter, such as sand, silt, clay, mulch, compost, and the like. A top dressing may be generally formulated for a wide variety of turf and further specifically formulated for an area of turf grass plants or sand, for example formulations specifically for applying/distributing onto a golf course green, such as tee top dressing, fairway top dressing, green top dressing, rough top dressing, a putting green top dressing, divot top dressing, sod top dressing, or a sandy area such as a bunker top dressing.

A "top dressing component" of the present inventions refer to a material or substance for making a top dressing material or mixture for use in the present inventions, such as a top dressing blended with a substance or active ingredient.

As used herein, the term "forming a concentrate" refers to adding an active ingredient to a top dressing material in an amount that is lower in concentration than the A.I. formulation and higher in concentration than the intended treatment, for example, making a pre-blend is providing a "concentrate" for use in the present inventions.

As used herein, the term "majority by weight" refers to an amount of an ingredient, such as the amount of sand in a top dressing material or top dressing composition where the amount is at least 50% of the total weight of the composition.

As used herein, the term "simultaneously" refers to at least two activates, such as blending and applying, spraying and delivering, mixing and delivering, and the like, occurring sequentially within a relatively short time frame. An exemplary simultaneous activity is provided such that a single top dressing vehicle of the present invention sprays a top dressing being moved by a conveying means to a delivering unit, i.e. a spinner or a brush, et cetera.

As used herein, the term "desired physical properties" in reference to a top dressing refers to physical properties, such as interpacking, compaction, pore space distribution (porosity), root zone compatibility, particle size, saturated hydraulic conductivity (perk rate), bulk density, particle density, pH, water retention, and the like.

As used herein, "interpacking" refers to compaction of particles, such that a wide spread of particle sizes will increase interpacking and decrease drainage.

As used herein, "porosity" in reference to a soil, sand, such as a top dressing, or mixture of soil and sand, refers to a measurement of the volume of water and air that can be held in a certain volume.

As used herein, the term "sand" or "sand particle" or "sand grain" or "sand granule" refers to an inorganic mineral particle whose diameter ranges between 0.053 mm or 53 microns in the United States, 63 microns in the United Kingdom to 2 (mm) (2000 microns) and in size, that may have a shape ranging from round to angular. The size of sand particles in a composition directly affects the amount of water retention, such that the coarser the particles the less water is retained. Conversely, sand composed mostly of fine particles retains more water. Sand may also refer to a loose aggregate of unconsolidated mineral particles or rock particles, such that a sand particle is illustratively formed from minerals selected from the following examples, silica, quartz, cristobolite, flint, chert, opal, chalcedony, feldspar, serpentinite, basalt, magnetite, mica, limestone, calcium carbonate, gypsum, chlorite, glauconite (gypsum), etc., of which at least 50% of particles are sand grain size of between 0.053 U.S./0.63 U.K. and 2 mm. "Sand" in reference to a top dressing material refers to a material comprising at least 50% sand particles.

As used herein, the term "silica" refers to an inorganic compound formed from silicon and oxygen, such as "silicon dioxide" or "$SiO_2$," that in natural form is found as a type of crystalline silica, for example, quartz, cristobalite, tridymite, etc.

As used herein, the term "silica particle" refers to a particle ranging in size from 2.0 mm to 0.053 mm, for example a silica particle ranges in size from coarse to fine silica.

As used herein, the term "particle" generally refers to a piece of solid matter, such as a particle of sand, clay, etc.

As used herein, the term "particle size analysis" or "PSA" refers to determining such parameters as the percentage of particle diameter in a composition, for example, a D15 (particle diameter at which 15% of the particles present are finer), a D85 (particle diameter at which 85% of the particles present are finer), etc.

As used herein, "silt" refers to an inorganic mineral particle between 53 microns (63 microns in the United Kingdom) and 2 microns in diameter, for example, a coarse silt particle ranges between 63 and 20 microns in diameter, a fine silt particle ranges between 20 and 2 microns in diameter. In a further example, the USGA defines silt as an inorganic mineral fraction between 53 and 2 microns in diameter.

As used herein, "clay" in reference to a particle refers to a phyllosilicate particle smaller than 0.002 millimeters (2 microns) in diameter, wherein a clay particle may be classified as very fine ranging from 0.05-0.1 mm, fine ranging from 0.1-0.25 mm, medium ranging from 0.25-0.5 mm, coarse ranging from 0.5-1 mm, and very coarse ranging from 1-2 mm.

As used herein, "gravel" in reference to a particle, refers to an inorganic particle greater than 2 mm up to 64 mm 2.0 microns up to 7.0 mm As used herein, the term "granule" refers to a particle of a certain mesh size, for example, a 15/30-mesh range is common. This means that at least 98% by weight of the particle will pass through a screen with 15 openings per linear inch, but not more than 5% will pass through a screen with 30 openings per linear inch. Particles smaller than 60 mesh are considered dusts.

As used herein, the term "diatomaceous earth" or "diatomite" refers to a particle of rock, high in amorphous silica content, formed from the structures of tiny fresh- and saltwater organisms called diatoms.

As used herein, the term "granular" refers to a composition, such as sand, a pesticide, a fertilizer composition, and the like. In some embodiments, a granular composition includes an agricultural chemical or nutrient attached to small, dry particles of some inert carrier such as sand, ground peanut hulls, vermiculite, ground corn cobs, etc.

As used herein, the term "coat" or "coating" or "coats" or "treating" or "treat" refers to covering a particle with a material, such as covering a top dressing material with a liquid formulation or a powder formulation. Coating may be accomplished by any means, for example, spraying the top dressing material with a liquid or powder, soaking the top dressing material in a liquid, etc., such that the AI is co-applied with the top dressing material. For use in the present invention, "coating" and "applying" may be used interchangeably in reference to covering a top dressing material with an AI, such that, the term "applying" in reference to coating a top dressing material, refers to coating a top dressing material with a substance, such as a fungicide, a pesticide, etc. by spraying, soaking, irrigation, and the like.

As used herein, the term "applying means" refers to a device for coating a top dressing material with an A.I., including devices such as an air-powered backpack sprayer, a bucket, a hand, a drop spreader, a blending device, and a top dressing vehicle, et cetera.

As used herein, the term "point-of-application" or "area of a golf course" or "turf," refers to a desired location for an application of a composition of the present inventions, such as a putting green, a fairway, a rough area, a tee, and a bunker. For use in the present inventions, the term "applying" in reference to a point-of-application, refers to placing one substance onto another, including delivering a top dressing material onto the surface of a golf course, an area of turf grass plants, and the like.

As used herein, the term "treatment" refers to a delivery or application of a composition onto an area of turf, such as an area of a golf course.

As used herein, the term "spot treatment" refers to an application of a top dressing, a composition of the present inventions, a fungicide, a pesticide, etc., to a limited or small area.

As used herein, the term "delivering" or "dispensing" or "application" refers to placing or distributing any composition of matter onto an area covered by turf grass plants, including a composition of the present invention, for example delivery may be accomplished by hand broadcast, machine spreading, brushing, spraying, machine broadcasting, irrigating, top dressing vehicle, and the like, onto an area of turf grass plants.

As used herein, the term "dispensing means" refers to a unit 6 for delivering or distributing a top dressing including a composition of the presenting inventions.

As used herein, the term "agricultural chemical" in general refers to chemicals such as herbicides, fungicides, insecticides, pesticides, nematicides, synthetic fertilizers, organic fertilizers, growth regulators, and the like.

As used herein, the term "active ingredient" or "AI" or "agriculturally active chemical" or "agriculturally active ingredient" or "active compound" or "active ingredient" or "active substance" or "agricultural chemical" or similar term refers to any type of chemical or substance that when applied to a plant or applied to the soil for growing the plant results in obtaining a desired result, i.e. an active agent is that portion of a fungicide product which provides the fungicidal properties, the portion of a pesticide product which provides pesticidal properties, a nutrient that enhances plant growth, and the like. An active ingredient may be organic or inorganic and an ingredient of a formulation, such as a fungicide, a wetting agent, an insecticide, an herbicide, a fertilizer, a synthetic fertilizer, an organic fertilizer, a nematicide, a plant growth regulator, et cetera.

As used herein, the term "cidal properties" in reference to a fungicide, a pesticide, and the like refers to the capability of the chemical to reduce the amount of fungus, pest and the like.

As used herein, "inorganic" refers to a substance of or derived from mineral origin.

As used herein, "organic" refers to a substance of or formed from living things, such as anything produced by or derived from, plants or animals. Organic in reference to a chemical compound refers to a substance containing the element carbon a form other than inorganic carbonates.

As used herein, "organic matter" refers to a substance, such as a top dressing component, comprising organic material.

As used herein, "organic matter" in reference to soil refers to a portion of the soil including substances derived from the life and death of plants, plant parts and other soil organisms.

As used herein, the term "soil" refers to the earth's thin upper layer capable of supporting plant growth, including topsoil, subsoil, et cetera. Soil is characterized by such things as texture, structure, color, and fertility, such as supporting plant and microbial life, which distinguish soil from material like gravel, sand or bedrock that also cover a portion of the earth's surface.

As used herein, "soil pH" refers to a numerical measure of soil acidity or alkalinity based on the hydrogen ion (H+) concentration in the soil. A pH of 7 indicates neutral conditions (neither acidic nor alkaline); above pH 7 is basic (alkaline) soil, below pH 7 is acidic soil.

As used herein, "texture" in reference to a soil refers to a relative proportion (expressed as a percent) of sand, silt, and clay particles in a soil, such that it determines soil "coarseness" or "fineness."

As used herein, the term "turfgrass" in reference to a plant refers to a desirable species or cultivar of grass plant that is maintained at a desired height through regular mowing, examples include, bent grass, annual bluegrass, ryegrass and the like, in particular a golf course green-turfgrass plant. Examples of turfgrass plants include older established turf grass plants and turfgrass plants specifically bred and/or engineered to provide "modern" turfgrass plants.

As used herein, the term "turf" in general refers to an area of land covered with turfgrass plants.

As used herein, "weed" refers to an undesired, uncultivated plant growing in a manner so as to adversely compete with desirable plants for water, light and nutrients, or destroy desired qualities of a golf course green, sports field or lawn, in general, weeds are removed by certain herbicides.

As used herein, "natural growth cycle" in reference to a turf grass plant refers to a sequence of grass root, shoot and flowering growth phases that occur naturally over the course of a growing season.

As used herein, "thatch" refers to a dense, fibrous layer of living and dead grass stems, leaves, and roots, without decomposition or partially decomposed, that accumulates between the green vegetation and soil surface.

As used herein, the term "mulch" refers to a composition of non-living material used to cover the soil surface, generally for such purposes as controlling weeds, conserving moisture, reducing soil temperatures, improving appearance, et cetera. Examples of mulch include, woodchips, compost, leaves, et cetera.

As used herein, "peat" refers to a partly decomposed plant material found in marshy areas. Identification or origination of parent plant material may still be possible (e.g., sphagnum peat moss).

As used herein, "humus" refers to a dark, fertile, partially decomposed plant or animal matter, such that humus forms organic portions of the soil.

As used herein, "compost" in general refers to partially to completely decomposed organic materials and additionally a range of products including simple mixtures of substances such as peat, sand, coir, loam, and actual composed material. "Composting" refers to the breakdown of degradable organic matter by microbes under moist, warm, aerobic (in the presence of oxygen) conditions.

As used herein, "coir" refers to the protective fibrous layer surrounding the hard shell in coconut fruits (*Cocos nucifera*). These fibers are the same used to make ropes and mats. During the fiber stripping process, the pulp surrounding the coir fibers is removed as a waste material. The residue is a crumbly brown substance often used in potting media as a bulk ingredient to increase moisture retention and porosity.

As used herein, the term "loam" refers to a composition of matter, including such substances as fertile soil, humus, sand, silt, clay, et cetera.

As used herein, "rhizome" refers to an underground root-like stem with scale-like leaves and roots originating from the nodes (bud containing areas along a stem).

As used herein, "rhizomatous" refers to a spreading growth resulting from the production and elongation of rhizomes.

As used herein, "root" refers to a fibrous, underground part of a plant associated with mineral and water absorption.

As used herein, "root zone" refers to a portion of the soil column occupied by plant roots.

As used herein, "canopy" refers to a layer of vegetation elevated above the ground As used herein, the term "foliage" refers to a leaf, such as a blade, or more generally, the green part of a plant.

As used herein "surface" in reference to delivering a top dressing refers to the aboveground area of turf, including the aboveground surface of a turfgrass plant, such as a blade or leaf referred to in general as "foliage."

As used herein, "scalping" refers to an undesirable mowing practice that removes an excessive amount of green leaves and shoots at any one mowing. It can seriously weaken or even kill the turfgrass plants.

As used herein, "grain" refers to the tendency of a species of grass to grow in a certain direction.

As used herein, "grainy" in reference to a putting green, refers to the tendency for grass leaves to lie down in one direction and interfere with the natural roll of the golf ball.

As used herein, "scalping" refers to cutting into or below the crown of the grass plant while mowing.

As used herein, "wear" refers to accumulative (usually deleterious) effects of traffic on a turf area.

As used herein, "aeration" refers to a supplying growing mediums and roots with air or oxygen.

As used herein, "aeration" in reference to a soil refers to a movement or exchange of air between the soil and the atmosphere.

As used herein, "aerification" in reference to a soil refers to a mechanical removal of soil cores to improve soil air exchange.

As used herein, the term "soil amendment" refers to a material that adds to the organic portion of a soil, for example, soil, peat, mulch, green compost, and the like.

As used herein, the term "soluble" refers to a compound that can be dissolved in water. In reference to a fertilizer, refers to a fertilizer that is made up of easily dissolved components in water that are immediately available for plant use.

As used herein, the term "suspension" refers to particles of a solid dispersed in a liquid but not dissolved.

As used herein, the term "diluent" refers to an inert material used in the composition of sprays, for example, water, and dusts, for example, diatomaceous earth, clay, and the like. A diluent is usually combined with an active ingredient to dilute or otherwise make the mixed material more suitable for field application.

As used herein, the term "emulsifier" or "emulsifying agent" refers to a surface-active material that reduces the separation of droplets of one liquid in another.

As used herein, the term "wetting agent" or "surfactant" refers to a compound that reduces the surface tension of the water, thus reduces the droplet size of a liquid.

As used herein, the term "spreader" in reference to a substance refers to a chemical or solution that increases the firmness of attachment of materials to surfaces.

As used herein, the term "inert" in reference to an "inert ingredient" refers to a material in a fungicide, pesticide, fertilizer, nutrient, growth regulator, composition that has no activity in creating the desired effect of the product. An inert ingredient may serve as a binding agent or carrier for the active ingredients such that they can be applied efficiently and uniformly.

As used herein, the term "effective amount" refers to the amount of a substance (e.g., including an active substance) sufficient to effect beneficial or desired results. An effective amount can be administered in one or more administrations, applications or dosages and is not intended to be limited to a particular composition or administration route.

As used herein, the term "pesticide" refers to a chemical or mixture of chemicals or biological agents used to control or eliminate any one of a microorganism, an insect, a plant or an animal pest in order to protect and/or preserve desirable plants, such as turfgrass plants.

As used herein, the term "insecticide" refers to a specific category of pesticides used for controlling or eliminating insects.

As used herein, the term "herbicide" refers to a chemical or mixture of chemicals or biological agent used to control or eliminate undesirable plants in a particular location, such as eliminating weeds in a turf plot.

As used herein, the term "phenoxy-type herbicides" refers to a category of systemic weed killers that have a chemical structure composed of six carbon atoms joined together in a ring formation, for example 2,4-D, mecoprop (MCPP), and the like.

As used herein, the term "broadcast application" refers to a uniform distribution of a material over an area of turfgrass, such as a top dressing, a fungicide, a fertilizer, a composition of the present inventions, and the like.

As used herein, "aerial application" refers to applying or delivering a material from an aircraft in flight.

As used herein, the term "cubic foot" refers to a volume measurement in feet, such that width times length times height equals cubic feet.

As used herein, the term "square feet' or "sq. ft." refers to a length (in feet) times width equals square feet.

As used herein, the term "adding" in reference to a method of the present inventions refers to an action of blending, mixing, spraying, and the like, for example, adding an active compound to a material, spraying a liquid onto a carrier, such as sand, and the like.

As used herein, the term "blending agent" refers to a material that enhances the even distribution of a mixture of materials, such as liquids or solids.

As used herein, the term "drying agent" refers to a material, such as anhydrous sodium, calcareous material, that removes water from a material, such as sand.

As used herein, the term "application volume" refers to the volume of a spray liquid (including pesticides, diluents, adjuvants, carriers and other components of the spray solution) applied per unit area (for example, expressed as liters per hectare or gallons per acre).

As used herein, the term "sprayer" in reference to a unit, refers to a means for applying a liquid or powder to a substance, typically comprising a pump, valves, tank, hoses, and a nozzle, for example, a sprayer may be used to coat a top dressing material with an active ingredient.

As used herein, the term "sprayable" refers to any material or substance, such as a chemical, capable of being sprayed by a sprayer.

The term "configured" in reference to "sprayer is configured to deliver a spray" refers to an operable combination of parts, including but not limited to a pump, tank, valve, hose and nozzle, for spraying a formulation.

As used herein, the term "nozzle" or "spray valve" or "spray nozzle" or "Spray Valve Nozzle" refers to a device with an opening, for regulating and directing a flow of fluid.

As used herein, the term "valve" in reference to a device for regulating the flow of liquid refers to a means for modulating the amount of fluid within a conduit, such as a hose, pipe, nozzle, and the like. A valve may alter amount or pressure of liquid within a conduit in response to a signal from a person or a control system, such as a signal from a flow regulator contemplated for use in the present inventions.

As used herein, the term "tank" in reference to a sprayer, refers to a container for holding or storing liquids, solids or gases. It is not intended that a tank be constructed in any particular shape or made up of any particular material.

As used herein, the term "tank tray" refers to a receptacle with or without sides or a raised edge or rim, used for carrying and holding a tank, such that a tank tray may be used to attach a tank to a top dressing vehicle.

As used herein, the term "deck" refers to a platform or surface, such as, a deck for mounting a spray tank. It is not necessary that the surface is uniform, and it may contain gaps or openings. For example, the platform may be designed as a grid with openings configured to permit support of appropriately sized tanks.

As used herein, the term "hydraulic" and "hydraulic system" refers to a system moved by, or operated by a fluid, e.g., oil, under pressure. A hydraulic pump refers to a mechanism for creating fluidic pressure. A hydraulic valve refers to a mechanism for altering the direction of fluidic pressure.

As used herein, the term "vehicle" in reference to a top dressing vehicle 1, refers to any type of machine used for blending a top dressing material and dispensing a top dressing material, including but not limited to a blending machine, a self-propelled machine and a trailer with on-board power or requiring power from a towing machine.

As used herein, the term "trailer" refers to a transport vehicle designed to be hauled by a truck or tractor (e.g., truckbed). A trailer may also be placed onto a transport vehicle.

As used herein, the term "spray" and "spray curtain" refers to the area where a formulation is applied after leaving a nozzle.

As used herein, the term "attach" in reference to attaching parts, such as a tank, hose, nozzle, etc. refers to any means of securing a part to a machine. Examples of attachment devices are direct, bolts, rivets, c-clamps, hangers, tape, wires, screw attachments, and the like, or indirect, for example attaching a nozzle by attaching a pipe where the nozzles are attached to the pipe, attaching a bar to the machine then attaching the nozzles to the bar, a tank tray for attaching a tank, and the like.

As used herein, the term "conveying means" refers to any device 8 for moving a substance, in particular a top dressing, for examples, conveyor systems, conveyor belts, belt conveyors, screw conveyors, augers, feeders, and elevators.

As used herein, the term "topdresser" in reference to a device, refers to a means for delivering a top dressing material to a surface, such as by spreading a top dressing onto a turf, dropping top dressing onto a turf, and the like.

As used herein, the term "drop spreader" or "spreader" "drop-type spreader" in reference to a top dressing vehicle, refers to a means for delivering top dressing materials, often comprising a "brush" for distributing the top dressing materials as the materials "drop" from a conveying means. Alternatively termed a "gravity spreader."

As used herein, the term "blender" in reference to a device refers to a means for mixing at least 2 different materials.

As used herein, the term "pathogen" refers to a organism, microorganism, or agent with the capacity to cause a plant disease including, but not limited to, viruses, bacteria, parasites (including, but not limited to, organisms within the phyla Protozoa, Platyhelminthes, Aschelminithes, Acanthocephala, and Arthropoda), and fungi, such as *Sclerotinia homoeocarpa* (Dollar Spot), Ectotrophic Root Infecting Fungi, Basidiomycete fungi (fairy ring), *Colletotrichum graminicola* (Anthracnose), Take-all Root Rot (black mycelia fungus), etc.

As used herein, "fungus" or "fungi" refers to a lower plant lacking chlorophyll that may attack green plants, such as mold, rust, mildew, and mushrooms are fungi.

As used herein, "fungicide" refers to a product that destroys or inhibits fungal growth, for example, a reduction in brown areas of turf.

As used herein, "fungistat" refers to a product that inhibits a fungus keeping it growth check, for example, stopping the expansion of a brown spot.

As used herein, "disease" refers to an interaction between a grass plant, a pathogen and its environment resulting in abnormal growth and/or appearance.

As used herein, "patch disease" refers to a non-specific term applied to small dead, circular areas in a live turf grass plant area (green) caused by a pathogen. Symptoms may also include the appearance of dead rings of grass, such as "fairy rings" with green grass inside and outside of the ring.

As used herein, "pest" in reference to a plant refers to an insect, mite, rodent, nematode, fungus, weed, or other organism capable of causing plant stress, injury or death through a disease, such as a fungus, a consumption of the plant, such as an insect, or competition with the plant, such as a weed.

As used herein, "pesticide" refers to a chemical or mixture of chemicals or biological agent used to control any one of a microorganism, an insect, a plant or an animal pest in order to protect and/or preserve desirable plants, such as turfgrass plants.

As used herein, "insecticide" refers to a specific category of pesticides used for controlling insects.

As used herein, "phenoxy-type herbicides" refers to a category of systemic weed killers that have a chemical structure composed of six carbon atoms joined together in a ring formation, for example 2,4-D, mecoprop (MCPP), and the like.

As used herein, "fertilizer" refers to a substances containing one or more of nitrogen capable of acting as a plant nutrient, phosphate, potassium and illustratively include urea, sulfur-coated urea, isobutylidene diurea, ammonium nitrate, ammonium sulfate, ammonium phosphate, triple super phosphate, phosphoric acid, potassium sulphate, potassium nitrate, potassium metaphosphate, potassium chloride, dipotassium carbonate, potassium oxide, urea ammonium sulfate, urea ammonium phosphate, proteins, amino acids, and any combination of these.

As used herein, the term "net weight" in reference to a substance in a formulation, such as a fertilizer, refers to an actual weight of the substance contained in a certain volume of formulation, for example, the amount of actual fertilizer in a fertilizer formulation.

As used herein, the term "liquid fertilization" in reference to a liquid fertilizer, refers to a method of applying or delivering plant nutrients as a solution of dissolved fertilizer salts.

As used herein, the term "solid fertilization" in reference to a solid fertilizer, refers to a method of applying or delivering plant nutrients as granules of fertilizer salts.

As used herein, "N—P—K: Chemical symbols for nitrogen (N), phosphorus (P) and potassium (K). On a container of fertilizer, these nutrients are expressed as percentages contained in the package and are shown in the order N—P—K.

As used herein, "Nitrogen" refers to an essential nutrient required for plant growth. It is a significant component of plant proteins. Adequate nitrogen produces good green color and vigorous plants. Yellowing leaves and poor growth usually indicates shortages of nitrogen. Excess nitrogen can result in unhealthy, lush growth making the plants more vulnerable to environmental stresses such as heat, drought, frost, and increased disease susceptibility.

As used herein, "Phosphorous" refers to a one of the major plant nutrients that is important in root growth and plant energy functions. Phosphorous is the middle number of a fertilizer analysis N—P—K.

As used herein, "Potassium" refers to a one of the major plant nutrients important in maintaining general plant health and vigor. Potassium often associated with improved stress and disease tolerance. Potassium is the third number in the fertilizer analysis N—P—K.

As used herein, "all-purpose" or "general-purpose" in reference to a fertilizer refers to a balanced blend of N—P—K, such as an all purpose fertilizer for soil and is used by most growers in the vegetative growth stage, examples include, Miracle-Gro fertilizer and Peters fertilizer.

As used herein, "nutrient" in reference to a plant or "plant nutrient" refers to a mineral element considered essential for plant growth. There are at least 16 minerals known to play essential roles in plant nutrition, for example, macronutrients, such as nitrogen (N), phosphorus (P), potassium (K), calcium (Ca), magnesium (Mg), sulfur (S), and micronutrients, such as boron (B), copper (Cu), iron (Fe), chloride (Cl), manganese (Mn), molybdenum (Mo), zinc (Zn), etc. such that fertilizer is a plant nutrient, in addition to secondary and micronutrients which illustratively include calcium, magnesium, sulfur, iron, manganese, copper, zinc; oxides salts thereof, ligands thereof, and combinations thereof.

As used herein, "nutrient release rate" refers to a speed at which plant nutrients, especially N, become available for plant use following application to a plant. This rate is often determined by the product, water and temperature conditions at the time of application.

As used herein, "plant growth regulator" refers to an active substance or preparation that contains one or more active substances which is intended to influence the life processes of a plant, destroy unwanted plants, or destroy parts of plants or control growth or prevent the undesired growth of plants.

As used herein, "irrigation" refers to a use of automated or manual systems for delivering supplemental water for the benefit of growing plants and replenishing soil moisture.

As used herein, "watering-in" refers to water applied to turf immediately after the application of a top dressing, a fungicide, a pesticide a fertilizer, or a composition of the present invention, in order to dissolve and/or move materials into the soil.

As used herein, "infiltration" refers to a physical process of movement of a substance into a soil, such as water, sand, fungicide, and the like.

As used herein, "leaching" refers to a downward movement in water of pesticides and/or nutrients through the soil column.

DESCRIPTION OF DRAWINGS

The parent or application file contains at least one drawing executed in color. Copies of the patent or patent application publication with color drawing(s) will be provided by the Office upon request and payment of the necessary fee.

FIG. 5 shows an exemplary brush drop-type topdressing vehicle 1 with A) four attached nozzles 2 for spraying topdressing before it drops into brush 6, and B) showing another exemplary embodiment for attaching nozzles where an attached (tape) hose 4, attached (tape) bar 5 was used for indirectly attached nozzles 2, and conveying means 8 for moving a topdressing material through a spray curtain prior to dispensing with brush 6.

FIG. 11 shows an exemplary topdressing vehicle 1 for use in the present inventions where dispensing unit 6, such as an elevator, was not being used and positioned away from conveying means 8 where A) shows one embodiment of an exemplary schematic hose 4 and nozzle 2, for spraying a formulation spray pattern as a schematic white triangle onto a conveying means 8, where the nozzle was located in between the outside of rear door 12 and end of conveying means 8, and B) shows one embodiment where elevator 6 is moved out of position which allowed the conveying means 8 to drop the moist coated topdressing material 7.

TABLE 1

Figure 1:
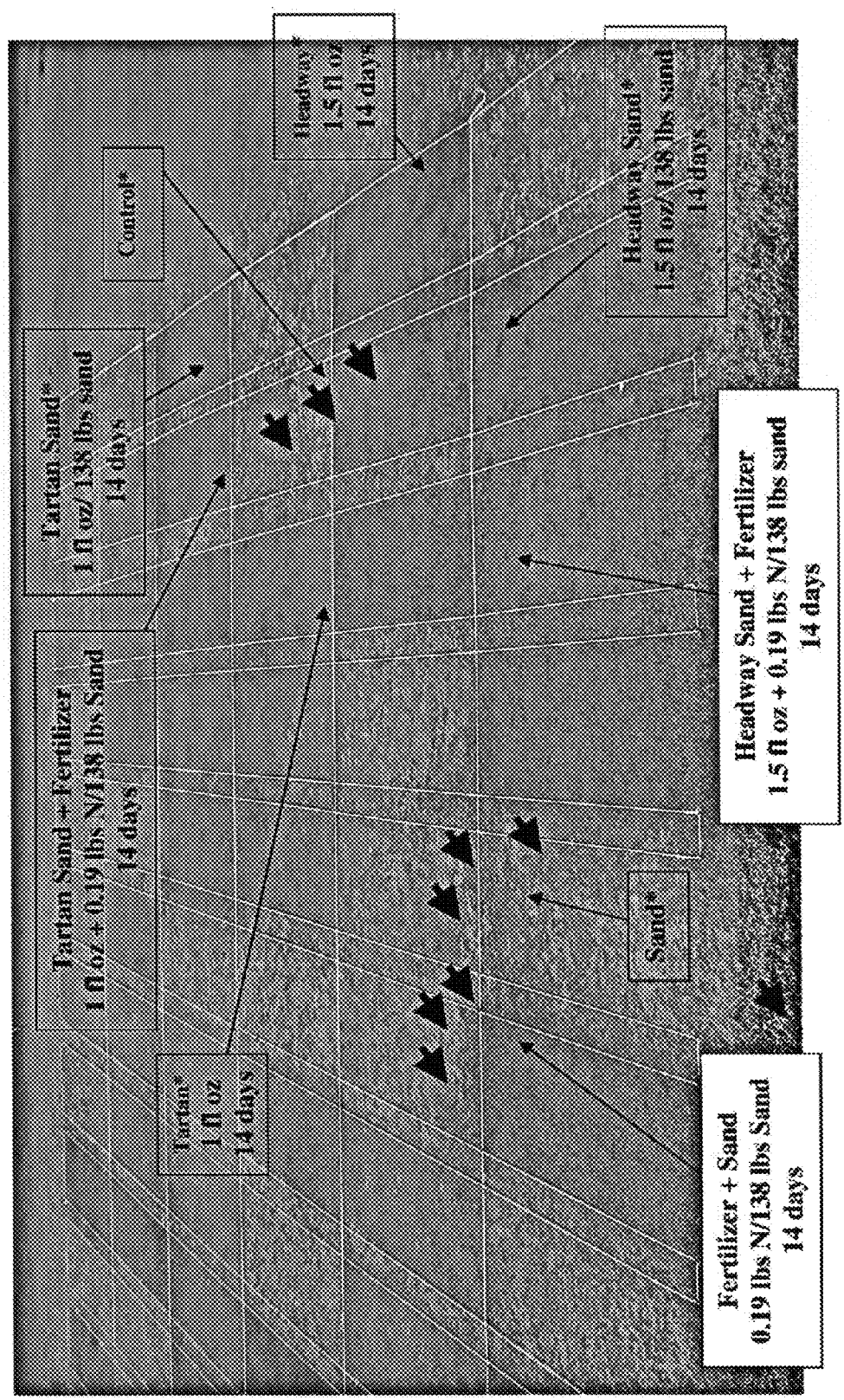
FIG. 1 is an exemplary photograph showing a Suppressive Sand Dollar Spot Study, 2007, demonstrating effectiveness of fungicide treated sand on turfgrass disease (dollar spot). Conducted at the Hancock Turfgrass Research Center, Michigan State University (M.S.U.), East Lansing, Mich. (MI). Treatment rates indicated are per 1000 sq ft. *Treatments received green's grade Country Club fertilizer (18-3-12) at a rate of 0.19 lbs N/1000 sq ft every 14 days. Arrows point to areas of dead turf.

Particle Size Distribution of a United States Golf Association (USGA) Recommended Root Zone Mix*

| Name | Particle Diameter mm | Recommendation (By Weight percentage %) |
|---|---|---|
| Fine Gravel | 2.0-3.4 | ≦10% total particles in this range including a maximum of 3% fine gravel (preferably none). |
| Very Coarse Sand | 1.0-2.0 | |
| Coarse Sand | 0.5-1.0 | Minimum of 60% particles must fall in this range |
| Medium Sand | 0.25-0.50 | |
| Fine Sand | 0.15-0.25 | ≦20% particles within this range |
| Very Fine Sand | 0.05-0.15 | ≦5% Total particles in this range shall not exceed 10%. |
| Silt | 0.002-0.05 | ≦5% |
| Clay | ≦0.002 | ≦3% |
| Total Fines | Very fine sand and silt and clay. | ≦10% |

*USGA Green Section Staff, USGA Recommendations for a Method of Putting Green Construction, Revision date Mar. 1, 2004, herein incorporated by reference.

TABLE 2

Physical Properties of a USGA Recommended Root Zone Mix*

| Physical Property | Recommended Range |
|---|---|
| Total Porosity | 35-55% |
| Air-filled Porosity (at 30 cm tension) | 15-30% |
| Capillary Porosity (at 30 cm tension) | 15-25% |
| Saturated Hydraulic Conductivity | Minimum of 6 inches/hr (150 mm/hr) |

*USGA Green Section Staff, USGA Recommendations for a Method of Putting Green Construction, Revision date Mar. 1, 2004, herein incorporated by reference.

Regular and repeated application of sand as a "top dressing" to golf course putting greens and tees is standard practice for increasing the quality of the playing greens and the preservation of putting quality. Sand top dressing increases playability by increasing surface firmness and smoothness, decreasing thatch, and decreasing grain. Insufficient sand top dressing may result in excessive organic matter accumulation in the upper soil profile. Excessive organic matter, or thatch, results in greater pest damage, shallow rooting, poor soil air exchange, and may cause the turf to be more prone to scalping.

Plants grown in excess sand frequently exhibit nutrient deficiencies and rapidly changing nutrient levels due to the low nutrient-holding capacity of this medium. Sand use may also alter soil pH, for example, calcareous sands used for putting greens in the Midwest have a high pH. For example, a fungus "take-all patch," caused by *Gaeumannomyces graminis* f. sp. avenae, is favored by alkaline soils. Bent grass greens constructed with high sand content or to USGA specifications are especially prone this disease. Further, turf grass plants, such as bent grass plants growing on sand mixtures, often appear more succulent and more susceptible to brown patch and Pythium blight.

Agricultural chemicals, such as pesticides, fertilizer, plant growth regulators, wetting agents, etc, are routinely and repeatedly applied to golf course turfs as part of a normal maintenance program. Rapid grow-in of golf greens is essential for quickly generating revenue at both newly constructed golf courses and those undergoing renovation. This is particularly important when using sand top dressing with their inherent deficiencies.

Repeated applications of a sand based top dressing for increasing playability and frequent applications of agricultural chemicals disrupts golf course operation, increases application efforts, and itself adds physical stress to the vegetation.

I. Overview of Problems with Current Golf Course Turf Grass Maintenance Practices.

Agricultural formulations comprising active ingredients, A.I.s, currently used for turf grass maintenance, such as fungicides, pesticides, etc., are applied as a single operation. These applications of A.I.s are separate operations from other types of turf operations, such as applications of topdressing. Further, these A.I.s are provided and used as either a spray or a dry formulation. Generally the dry formulations are typically more desirable to use since the A.I. is generally more concentrated than a comparable spray and easier to apply. However, both types of formulations have numerous limitations such as allowing A.I.s to be highly susceptible to loss of efficacy during and after application due to numerous factors. In particular, spray applications render A.I.s susceptible to factors such as spray drift, runoff from wind erosion, traffic, photodegradation, precipitation or irrigation thereby loosing efficacy, especially in the soil. Dry formulations increase the incorporation of the A.I. into the soil matrix however efficacy is lost when the A.I. moves into surrounding areas. Dry formulations are subject to removal from point-of-application by wind, runoff from precipitation and irrigation, traffic, and the like. Moreover both types of formulations allow the A.I. to undergo further losses in efficacy due to environmental factors such as photo-degradation, volatilization, oxidation, and further mere mechanical removal by operations such as mowing the turf grass plants.

The inventors contemplate that by formulating and using A.I.s as described herein, specifically by adding A.I.s directly to top dressing materials, such as sand, prior to or simultaneously in a single application, these types of looses would be significantly reduced. Such that formulations and methods of the present inventions are contemplated to protect A.I.s and increase their efficacy by providing A.I.s as part of a protective layer of topdressing which provides a greater solid volume and mass of the A.I. formulation than the usual methods of A.I. applications. Further, the formulations of the present inventions are contemplated to allow a greater incorporation and stability of the A.I. into desired parts of the soil matrix, which should overcome many of the limitations of current types of A.I. applications. For example, fungicides and pesticides are highly inefficient when applied directly onto turf grass plants due to factors such as a lack of proper placement and retention of A.I. at the most opportune site of action, i.e. where the pests are active on the foiler surface, in the upper layers of sod and in the soil. Because the majority of pest problems in turf (e.g. fungus, weeds, pathogens, insects, etc.) originate in the soil, the soil surface and the space immediately above represent a preferred area of placement for many active ingredients. It is contemplated that current application methods are not capable of providing an effective amount of an A.I. where the pathogens reside. Therefore, the capability of the solid matrix of an A.I. coated sand layer of the present inventions to retain the A.I. within its structure seems to be one key to explain why the inventors observed improved or equivalent efficacy with the use of formulations of the present inventions, in particular combined with new methods of application of the present inventions when compared with conventional approaches, i.e. formulations and methods of application currently in widespread use on turf areas.

Even further, these is a need to discover greater cost effective and simpler ways, i.e. reduced manpower, of treating turf, in particular golf course turfgrass which is high maintenance and expensive to properly maintain properly. Primarily, there is the cost and difficulty in hiring and retaining the skilled highly trained applicator personnel for first determining when and how much A.I. should be applied and secondly the process of actually handling and applying or delivering toxic chemicals, including many active ingredients. Additionally, any one of the following is burdensome to personal and expensive to golf courses, i.e. cost of machinery, cost of fuel, pollution from burning fuel, cost of other energy required for separate uses of powered applicator equipment, et cetera. For many turf maintenance operations, the cost of custom application of A.I.s due to outbreaks of pathogens and diseases is very burdensome to golf course managers.

Previous attempts were made by others with the goal of reducing maintenance of turf grass areas by combining fertilizers with fungicides in one composition that was then applied onto turf grass. As one example, fungicides, specifically imidazolyl structurally based fungicides, were described as several types of combinations, such as combinations of imidazolyls with a wetting agent, fungicides in combination with a carrier, such as water, water and silicas, and fungicides in combination with surface active agents, such as emulsifying agents, dispersing agents, and wetting agents, in U.S. Pat. No. 4,853,400, herein incorporated by reference. However, there is no indication that any of these combinations other than an imidazolyl in combination with an unnamed wetting agent that was sprayed onto an unnamed plant, were actually made and used. Another example described combinations of fertilizer with plant growth regulators, including a plant growth regulator that functioned as a fungicide, i.e. paclobutrazol, in a family of applications including U.S. Pat. No. 4,704,160, herein incorporated by reference, and "[a] fertilizer-fungicide combination product" Lebanon Turf ProScape 14-2-14 comprising PCNB (Terraclor, 1,2,3,4,5-pentachloro-6-niro-benzene) at 12.5%, that provides "control of many turf damaging diseases including . . . . Dollar Spot" was described in publications posted by "Horizon Fertilizers," available online at world wide web.horizononline.com. In yet another example, a nematicide was disclosed, specifically thiadiazole based compounds, where mixtures of the disclosed nematicide were described with a long list of materials including granulated non-adsorptive carriers, such as sand, in U.S. Pat. No. 4,861,787, herein incorporated by reference.

In even further published examples, sand was mixed with peat, as in a publication by Harford TD 1000 Top Dressing Material, available online at worldwide web.harfordminerals.net/topdressing.html, herein incorporated by reference. This reference discloses the combination of quartz with an organic (humus or sphagnum peat) and silica sand with peat for use in top dressing applications. The authors state that the material meets USGA specifications as "Construction Blends" comprising "Harford Mineral's multi-washed silica sand, pre-sized to USGA specifications and blended with humus or sphagnum peat, where top dressing is available in various proportions of sand to peat: 80/20, 90/10 as well as straight sand top dressing." and "Divot & Tee Mix—50/50 Divot Mix, replace those divots with Harford's blend of 50% USGA silica sand and 50% peat. The mix is not dried and its dark color and high moisture content enable heat to be retained for faster seed germination."

In contrast, a publication indicated that spraying fungicide on turf grass plants growing in pots of sand would not protect these plants from fungal diseases. Specifically, turfgrass plants growing in sand were sprayed with imidacloprid, as Merit 75 WP (Bayer), and fertilized, in separate applications for successful control of curvularia fungus on Kentucky bluegrass plants, but not on several other grasses, such as bent grass plants, Bermuda grass plants, nor were these treatments successful in preventing or controlling other diseases that broke out on these plants, see PCT Publication Number WO 2006/023899/US 2007/0287720, herein incorporated by reference.

II. Compositions and Formulations of the Present Inventions.

During the course of development of the present inventions, the inventors observed that recommended frequency range (weekly to monthly) of top dressing applications is parallel to the typical application intervals for A.I.s, such as pesticides and fertilizers. Further, newer varieties of turf grass plants benefit from applications of 14-day intervals of sand topdressing, which is similar to recommended applications of a fungicide or other chemical treatments for control of pathogen outbreaks. Thus the inventors contemplated and provided formulations of the present inventions comprising A.I.s and topdressing for use as part of an ongoing maintenance practice of top dressing. In a preferred embodiment, the top dressing of the present inventions would be applied on 14-day intervals during the period of infestation or for preventative maintenance. However, single applications of topdressings of the present inventions are contemplated on an as needed basis. Further, the inventors contemplate delivering top dressings of the present inventions on an interval basis as needed for the particular application of A.I. with top dressing. This combined application of top dressings of the present inventions would remove the need for separate applications of active ingredients. The inventors contemplate that even further; the combination of operations would significantly reduce the cost of turf maintenance and improve the quality of turf grass plants. This reduction of cost is supported in part by a publication comparing the cost of separate applications of sand and fungicide, Alexander et al. (2004) "Increasing Dollar Value for Compost Products," BioCycle 45, 48-51, herein incorporated by reference, including the separate applications of fertilizer and fungicide for the treatment of turf.

Therefore, the inventors contemplated and tested the composition and use of a variety of types of top dressing compositions comprising a sand particle carrier, as described herein. These formulations include moist top dressing formulations (i.e. liquid chemical (A.I.) coated moist sand, liquid chemical (A.I.) coated dry sand, dry sand sprayed with liquid chemicals at point-of-application, in particular providing this type of composition using topdressing vehicles of the present inventions, liquid chemical coated sand that was subsequently dried prior to use, and the like) and dry top dressing formulations (i.e. A.I. chemicals provided within granules blended with dry sand, A.I. chemicals provided within granules blended with moist sand, and the like), and the like).

In one preferred embodiment, the top dressing material is local sand for matching the soil type and composition of root zone materials. In another preferred embodiment, the sand used is kiln-dried sand, which is then sprayed while on the conveying means prior to entering the drop or spinner units. In another embodiment, the sand is moist sand, which is then sprayed while on the conveying means prior to entering the drop or spinner units. In general, the methods comprising topdressing vehicles of the present inventions provided herein in the Examples, were conducted with moist sand, i.e. 1/3 kiln dried sand and 2/3 moist greenhouse sand, yielding approximately 1-10% weight per volume water prior to application. The inventors contemplate the exemplary use of a topdressing material for blending or coating in the range of 1-10% weight per volume water prior to application.

Therefore, in one embodiment, the inventions provide a moist top dressing formulation comprising an A.I. and sand. In one embodiment, the formulation is a liquid formulation that is used to coat a sand particle. In one embodiment, the formulation is a liquid formulation that is used to form a solution with a sand particle. In a further embodiment, the inventions provide a moist topdressing formulation, which is subsequently dried prior to application. The inventors contemplate drying compositions by air-drying, drying with an on-site kiln, drying with a kiln located on the golf course premises, or near the golf course, or in the vicinity of the area of turf targeted for topdressing applications, or any manner of drying a composition of moist topdressing prior to application.

The inventors contemplate various types of formulations for specific applications. In particular, embodiments comprising solutions intended for spray applications are contemplated. Specifically in a preferred embodiment, a spray is prepared as a liquid solution comprising an active ingredient and a solvent. The type of solvent used to prepare solutions will depend upon the use of the formulation. For example, in agricultural applications, such as applications to turfgrass, water is a preferred solvent. In some embodiments, ethanol is used as a solvent for spraying an A.I. onto a top dressing material. In some embodiments, sprays are targeted for foliage applications. In other embodiments sprays are targeted for soil applications. In yet other embodiments, sprays are targeted for both foliage and soil.

According to the present invention an agricultural chemical is applied to a top dressing component and preferably at least a portion of the sand component of a top dressing. The agricultural chemical optionally is itself a liquid that coats a sand particle or other top dressing particle. Alternatively, the agricultural chemical is part of a solution or emulsion that coats a sand particle or other top dressing particle. The agricultural chemical optionally is a wettable powder that is used to form a suspension with a sand particle or other top dressing particle. In another embodiment, wettable powders which are soluble or dispersible in water may be formed by mixing the chemical in particulate form with a particulate carrier or spraying the chemical compound onto the particulate carrier and grinding the whole powder mixture into a granule or particle. In another embodiment, the composition of a wettable powder of the present inventions further comprises a wetting agent and a dispersing agent.

Further, embodiments comprising granules for blending with topdressing are also contemplated. Therefore, in another embodiment, the inventions provide a dry top dressing composition comprising an A.I. and sand. In one embodiment, the formulation is a solid formulation, such as a particle, i.e. dust, granule, and the like which is used to mix with a top dressing material such as a sand particle.

In a preferred embodiment for a dry formulation, the agricultural chemical, A.I., is provided as a solid composition, such as a dust, or granule, which is used to mix with a sand particle or other top dressing particle. The present inventions further provide methods of application of mixed granular material, such that conventional topdresser machines would broadcast premixed compositions. However, application of pre-mixed material transported over long distances is contemplated to undergo transport settling and further, transporting large volumes of sand, especially moist sand, over long distances is expensive and time consuming. Therefore, in a preferred application, mixing of granular materials of A.I. with top dressing material would occur at point-of-application. Several exemplary blender-type top dressing vehicles are provided herein for use at point-of-application, however these examples are not meant to limit the methods of the present inventions. In a preferred embodiment, blending dry granule formulations would be done using a commercially available blender, such as a Dakota 440 TurfTender (Dakota Peat and Equipment, Grand Forks, N. Dak.) with an attached blending unit. This machine was designed to blend two types of granular materials for subsequent spreading (see, at world wide web.dakotapeat.com/news/equipment/022508.html with a blender option, and United States Patent Applications Number 20060006256 and related portfolio, all of which are herein incorporated by reference). In another preferred embodiment, a combination blender/topdresser machine is contemplated to be particularly well suited for blending and delivering compositions of the present inventions at point-of application. In particular, a machine combination blender/topdresser machine takes the separate top dressing feedstock components and mixes the components as the mixture is broadcast distributed, for example, a Dakota 440 TurfTender (Dakota Peat and Equipment, Grand Forks, N. Dak.) with an attached blending unit.

A second exemplary machine is a TURFCO blender (see, at world wide web.turfco.com/html/osforsptd.htm, herein incorporated by reference). In these embodiments, distribution in concert with mixing has the added advantage of precluding transport settling and eliminates the need to transport large volumes of heavy material of relatively low value to the turf site. The advantages gained over current practices would include a distribution of top dressing and A.I.s with a high degree of uniformity.

A. Active Ingredients for Use in Formulations of the Present Inventions.

The inventors contemplate a range of active ingredients for including in compositions of the present inventions for delivering as a single application as part of routine turf grass management. In particular as part of routine top dressing applications for reducing personal time and cost of managing turf, such as found on golf courses, playing fields, and the like.

Exemplary compositions comprise top dressing materials in combination with at least one A.I. for application to turf grass. In further exemplary methods, mixing, blending or spraying is used for combining top dressing with an A.I. In even further embodiments, methods comprising mixing, blending and spraying include the use of top dressing vehicles of the present inventions. In yet further embodiments, application of compositions of the present inventions include the use of top dressing vehicles of the present inventions.

In a preferred embodiment, the topdressing/A.I. composition comprises a fungicide. In other embodiments, the topdressing/A.I. composition further comprises a fertilizer. In another embodiment, the topdressing/A.I. composition further comprise a plant growth regulator (PGR), which is often applied to highly managed, cool-season turf grasses every few weeks throughout the growing season to reduce clipping production, increase sward density, reduce seed head formation and enhance sward color (Lickfeldt et al., 2001, Agron J. 93:1164-1168, herein incorporated by reference). In other embodiments, the topdressing/A.I. composition further comprise an active ingredient as described herein as exemplary compounds however the inventors do not intend for these examples to limit the types of A.I.s that would find use in compositions and methods of the present inventions. Indeed, as the field of agricultural chemicals advances, numerous types of A.I.s are continually being developed and used. Therefore the inventors contemplate including and using future chemicals as they are available for use in the compositions of the present inventions.

In general, exemplary fungicides for use in compositions of the present inventions include phenylamides, morpholines, phosphorothiolates, orathiins, hydropyrimidines, Anilinopyrimidines, N-Phenyl Carbamates, Melanin Biosynthesis Inhibitors, Hydroxyanalides, Phenylureas, Benzimides, Phosphonates, and any type of plant host defense inducer/activator that would protect a turf grass plant from infections and death. For example, an exemplary plant defense activator is acibenzolar-5-methyl (ASM, Actigard, Syngenta Corp., Basel, Switzerland). Acibenzolar-5-methyl is reported to induce systemic acquired resistance in plants and has been shown to have antifungal, antibacterial, and antiviral activity (Cole, 1999. Crop Prot. 18:267-273, herein incorporated by reference). This chemical has no known direct antifungal properties (Lawton, et al., 1996. Plant J. 10:71-82 in office, herein incorporated by reference). However, when ASM was applied to bent grass, the number of S. homoeocarpa infection centers in a blend of Cato:Crenshaw (50:50) was reduced by 38%; however, disease pressure was high, and turf quality was unacceptable through much of the study period (Lee, et al., NHortScience). Lee, et al., Plant Management Network. Published 26 Jun. 2003. http://at worldwide web.plantmanagementnetwork.org/pub/php/research/2003/dollar/, herein incorporated by reference.

The inventors contemplate formulations comprising sand with an active compound, such as fungicides listed herein, and further for example, those fungicides described in U.S. Pat. No. 4,853,400, herein incorporated by reference, benzoyl phenyl urea derivatives having insecticidal activities, for example, those described in U.S. Pat. No. 4,013,717, herein incorporated by reference), nematicidal compositions, for example, those described in U.S. Pat. No. 4,861,787, herein incorporated by reference, and herbicides comprising benzoylcyclohexanediones and safeners, for example, those described in U.S. Pat. No. 7,101,827, herein incorporated by reference), and 4-trifluoromethylpyrazolyl-substituted pyridines and pyrimidines, for example, those described in U.S. Pat. No. 7,211,673, herein incorporated by reference.

Additional representative fungicidal active ingredients and representative microbiocidal active agents, for treating and preventing pathogen infections and infestations are provided. These chemicals and chemical classes are provided to illustratively include plant and general disease control agents including but not limited to fungicides, fungistats, antibiotics and bacteriocides of the following chemical families and functional groupings; imidazole heterocyclic derivative, triazole heterocyclic derivative, demethylation inhibitor (DMI), strobilurins, triadimefon, trifloxystrobin, propiconazole, azoxystrobin, various acetamides; sterol inhibitors or demethylase inhibitors; dicarboximides (such as iprodione); phthalides; phthalmic acids; triadiazoles; isophthalates; triazines; triconazoles; strobilurins; Stobin (e.g., azoxystrobin, dimoxystrobin, fluoxastrobin, kresoxim-methyl, metominostrobin, orysastrobin, picoxystrobin, pyraclostrobin, trifloxystrobin, etc.); benzimidazoles; benzithiazoles; dithiocarbamates, such as polymeric dithiocarbamate fungicide is mancopper, mancozeb, maneb, metiram, polycarbamate, propineb, zineb, etc.; carboxamides; carboxides; anilides, such as phenylanilide, benalaxyl, benalaxyl-M, boscalid, furalaxyl, metalaxyl, metalaxyl-M, etc.; chlorphenyls; indolecarboxylic acids; isoxazoles; imidazoles; oxazolinediones; guanidines; diguanidines; piperidines; pyridines; sulfenamides; sulfonamides; quinolines; cyanoimidazoles; pyrazoles; pyrrolecarbonitriles; spiroketalamines; thiazoles; various chemical families of oomycete (pythium) fungicides; nitriles; chlorinated hydrocarbons; phenylpyrroles; polyoxins; pyridazinones; mycotoxins (e.g. penicillin) or other antibiotics (e.g. streptomycin, kasugamycin, blasticidin, polyoxins, validamycin, mildiomycin, and oxytetracyline); morpholines; other organic compounds such as piperalin, piperazine derivatives and tolylfluanid, bronopol, organic compound mixtures (e.g. bacticin and harpin protein), organic acids such as trinexapac ethyl, cinnamic acid and its derivatives, bacteria such as *Agrobacterium radiobacter, Bacillus, Erwinia carotovora, Pseudomonas flourescens* and *P. chlorophis*, and any varieties or strains thereof, fungi such as *Candida oleophila, Fusarium, Tricoderma, Gliocladium, Polyversum, Streptomyces*, and *Ampelomyces* and any species, varieties or strains thereof, and viruses such as tomovax.

The inventors further contemplate preferred embodiments using an herbicide as an A.I. for reducing weeds. For purposes of this invention, herbicide active agents illustratively include but not limited to dintroanilines such as benefin, trifluralin, pendimethalin, and prodiamine, oxadiazoles such as oxadiazon, triazines such as atrazine and simazine, triazolinones such as carfentrazone and sulfentrazone, Aryloxyphenoxy propionates, Arylaminopropionic acid, Cineole (such as cinmethylin), Cyclohexanediones, Sulfonylureas such as trifloxysulfuron and metsulfuron-methyl, Imidazolinones, Pyrimidinylthio-benzoate, Triazolopyrimidine, Pyridazine, Phenoxys (or Phenoxies), Benzoic acids, Carboxylic acids (such as DCPA, clopyralid, trichloroacetic acid, and fluoroxypyr), Quinoline carboxylic acid, Semicarbazone, Triazinones, Uracils, Pyridazinone, Phenyl-carbamates, Nitriles, Benzothiadiazoles, Organoarsenicals, Phenyl-pyridazine, Triketones such as mesotrione, Ureas and substituted ureas (such as diuron, linuron, siduron, tebuthiuron, dymron etc.), Amide (such as propanil and bromobutide), Thiocarbamates, Pyrazolium (such as difenzoquat), Phosphoric acid compounds (such as glufosinate-ammonium and glyphosate), Triazole, Pyridazinone, Nicotinanilide, Pyridinone (such as fluridone), Isoxazolidinone, Diphenylethers, N-phenylphthalimides, Oxadiazole, Triazolinone, Chloroacetamides, Oxyacetamides, Phthalamate, Phthalamate Semicarbazone, Nitrile, N-phenylphthalimides, Oxadiazole, Triazolinone, Acetamides, Benzoylisoxazole, Isoxazole, Pyrazole, Pyrazolium, Triketone, and Benzofuran, various ALS inhibitors, and plant extract herbicides such as the allelopathic exudates of various plants.

For purposes of this invention, insecticides include but are not limited to pyrethroids such as bifenthrin, permethrin, deltamethrin, lambda cyhalothrin, cyfluthrin, or betacyfluthrin; organophosphates such as chlorpyrifos; limonoids such as azadirachtin or meliartenin; phenyl pyrazoles or oxadiazines such as indoxacarb; phthalic acid diamides such as flubendiamide and anthranilic diamides, carbamates such as carbaryl (1-naphthyl N-methylcarbamate), neonicotinoids or nitroguanidines such imidacloprid, thiomethoxam, clothianidin or dinotefuran; diacylhydrazines such as halofenozide; neonicotines such as floconamid; organophosphates such as trichlorfon and pyrazoles such as fipronil. It is appreciated that multiple active pesticide agents are readily formulated within a pesticide powder operative herein.

The inventors further contemplate compositions of the present inventions comprising a nematicide, for examples, substituted 2-mercapto-5-furyl-1,3,4-oxadiazoles, substituted 2-mercapto-5-furyl-1,3,4-thiadiazole derivatives, 2-mercapto-5-thienyl-1,3,4-oxadiazole derivatives, 2-mercapto-5-thienyl-1,3,4-thadiazole derivatives and the like.

The inventors further contemplate compositions of the present inventions comprising a fertilizer. There are numerous types of fertilizers that would find use in the present inventions, including but not limited to slow release, soluble, and water insoluble formulations, and synthetic fertilizers.

1. Concentrations of A.I.s in Formulations of the Present Inventions.

It is appreciated that the amount of top dressing applied, as well as the component mixture of conventional top dressing varies with factors illustratively including soil drainage, root zone water holding capacity, water percolation rate, air circulation ability, pore space, compaction, pH level, thatch, black layer, or hydrophobia. In addition, A.I.s formulated in high concentrate granules for some treatments would remain at too high of a concentration even after blending with a top dressing material.

As a result, the inventors contemplate providing a "pre-blend" for use in the present inventions for providing even greater flexibility and economy for making and using the present inventions. In one embodiment, the pre-blend mixture would allow an intermediate mix for lowing the concentration of A.I. prior to the mixing with a top dressing material at a point-of-application.

Therefore, in one embodiment, the inventors contemplate making a "pre-blend" or "pre-blended top dressing material" for use as a concentrated form of an A.I. prior to subsequent spraying or further blending of mixtures of the present inventions. For example, a first top dressing component is added to or blended with a concentrated formulation of an active ingredient such that the pre-blend is at a higher volume or weight than the original granules and at a lower weight or volume than the intended final mixture for delivering onto an area of turf. Therefore in one embodiment, the first top dressing component is contemplated as a light weight or adsorbent material, such as ground corncobs, peanut hulls, coconut fibers, vermiculite, and the like. In other embodiments, the top dressing component is sand, peat, soil, and the like. In a preferred embodiment, the pre-blend concentrate is dry.

As an example, the inventors contemplate a recommended range of using pre-blended sand topdressing amounts, in rates ranging from 0.025 cubic yd./1000 sq. ft./14 days between treatments on quality greens (with minimal thatch) to 0.2 cubic yd./1000 sq. ft./14 days for lower quality greens, such as bermudagrass greens with heavy thatch (Beard, J. B. 1982. Turf Management for Golf Courses p. 144, Burgess Publishing Co, Minneapolis; Beard, J. B. (and The United States Golf Association) 2002. Turf Management for Golf Courses, second Ed, Ann Arbor Press. p. 159 and Table 3.1, Ann Arbor Press, Chelsea, Mich., herein incorporated by reference). However, for last top dressing treatments of the season in northern regions, even higher sand rates are sometimes used to help protect the turf crowns from desiccation, low temperature kill, etc., during the winter. Therefore, the inventors further contemplate an amount of A.I. in granular product used in a pre-blend to range from 46%, to 50% or higher for the final pre-blend amount.

However it would depend upon the type of A.I., for example, in the case of a product such as a urea fertilizer or a very efficacious granular systemic fungicide like Andersons Compass G then the amount is contemplate to be 0.157%, or less of the pre-blend.

The inventors further contemplate using the pre-blend at a point-of-application by mixing the pre-blend concentrate with varying amounts of top dressing components or varied types top dress materials to customize a treatment to serve as both a top dressing function as well as to simultaneously delivery an agricultural chemical. By way of one example, a 50 pound bag of sand having individual sand particles coated with a fungicide, is contemplated for loading into the small hopper 15, of a Dakota Top dresser comprising a Blender unit 9, along with a pre-blend of 1500 pounds sand, 300 pounds of loam, and 200 pounds of peat loaded into the primary hopper 14, see, FIG. 10. The fungicide formulation would be simultaneously blended into the pre-blend mixture to form a composition of the present inventions as it is applied to turf in a preselected amount per unit are of turf, in a quantity sufficient to improve turf quality through top dress and to apply the fungicide at a preselected amount per unit area of turf for controlling or prevention a fungal infection of the turfgrass plants, see, FIG. 15 for example.

Contemplated ranges of A.I.:top dressing (sand) ratios for compositions of the present inventions. Depending on the type of chemical (fungicide, herbicide, insecticide, plant growth regulators, etc.) being applied to sand, the A.I. can range from 0.01 oz/1000 sq. ft. to 8-oz/1000 sq. ft. or more. Some fertilizers, soil wetting agents and conditioners, etc., would generally be applied at even higher A.I. rates, measured in pounds of A.I./1000 sq. feet. Thus the inventors contemplated an attribute of the inventive compositions of the present inventions where turf treatment of a liquid agricultural chemical component would be at a lower amount of the total weight percentage of the composition than conventional spray distribution compositions or solid applications for that agricultural chemical.

Concentrations of fertilizers would depend upon the type of fertilizer and application goal. In general, the inventors contemplate using fertilizer concentrations comprising amounts of nitrogen ranging from a half pound per thousand square feet to two pounds per thousand square feet. Such fertilizers include nitrogen:oxygen:phosphorous (N—O—K) ratios as described herein in the examples, and further exemplified by ratios such as 36-6-6, 18-3-12, 13-12-0, 18-4-12, 3-1-12, and the like, in general ranging as nitrogen:oxygen:phosphorous ratios of 36-18:6-3:6-12. In particular, as new varieties of turf grass plants are being developed, and as older varieties adapt to various growing conditions, the inventors recognize that fertilizer requirements are likely to also change. Thus any concentration of fertilizer that would support and further encourage growth of turf grass plants is contemplated to find use in compositions of the present inventions.

As further exemplary descriptions, active ingredients as provided herein comprising herbicidal, pesticidal, nematicidal, insecticidal, etc. activity typically would be present from 0.01 to 0.4 total weight percent of an inventive top dressing composition; a synthetic fertilizer agricultural chemical would typically present from 0.05 to 2 total weight percent of an inventive top dressing composition; and a growth regulator would typically represent from 0.0001 to 0.05 total weight percent of an inventive top dressing composition. These amounts are significantly lower than currently applied sprays and granules. These low concentrations of active ingredients in an inventive composition relative to conventional applications are further contemplated to prevent turf injury from concentrated chemicals due to misapplication or spills. While the mechanism of action is not fully understood, the properties of top dressing also promote efficient usage of the agricultural chemical and allow for less overall usage of the agricultural chemical to achieve a desired result.

However certain applications require higher concentrations of A.I. for effective applications. Therefore, when higher levels of A.I. are required for effective treatments of turf, the inventors contemplate a preferred embodiment of a dry formulation comprising blends of A.I. granules and top-dressing, i.e. sand. Thus in additional embodiments, A.I.s would be applied to sand in amounts ranging from 0.025 cubic yard/1000 sq. ft. to 1 cubic yard/1000 sq. foot. Alternatively, the inventors contemplate using concentrated spray solutions for achieving similar results. For any contemplated concentration of A.I. treatment, the final concentration used will depend upon the interval between applications, and the type of grass being top dressed, and the like. Thus for higher concentrations of A.I., in one preferred embodiment, a concentrate of the agricultural chemical mixed with at least one top dressing component is provided that has the agricultural chemical present from 10 to 300 times that of a broadcast application concentration of the agricultural chemical alone. More preferably, the agricultural chemical is applied to a single top dressing component or a combination of components that at density matched to within 30% so as to lessen settling that would necessitate added mixing time upon addition to a larger volume of top dressing material. Most preferably, an agricultural chemical is applied to a volume of sand that is then intermixed with a larger volume of conventional top dressing sand and optional loam and peat see examples described herein.

2. Types of Formulations and Components.

The inventors further contemplate embodiments comprising a variety of types of formulations for use in compositions of the present inventions. In one embodiment, the formulation is a solution, such as a spray prepared as a solution comprising an agricultural chemical and a solvent. The type of solvent used to prepare solutions will depend upon the use of the composition. For example, agricultural applications, such as applications to turfgrass, would use water as a solvent. However in one embodiment In one embodiment, the formulation is a wettable powder formulation that is used to form a suspension with a sand particle. A "wettable powder" or "WP" in general refers to a dry chemical formulation that does not dissolve in water but remains suspended in it. A wettable powder may also be referred to as a flowable, for example, a flowable powder, such as Cypermethrin products (Demon WP, Cynoff WP). When a wettable powder is mixed with water or other liquids, a suspension spray is formed. Wettable powders in general extend the efficacy period of the active ingredient. In some embodiments, a liquid flowable (LF) contains insoluble, finely ground solid active ingredients mixed with a liquid (and inert ingredient) to form a suspension. In some embodiments, a dry flowable (DF) active ingredient is prepared as dry, granular-sized A.I. particles such that when the granules are mixed with water, the granules break into fine particles and form a suspension for application, such that advantages of using DFs include easier to measure and mix than wettable powders with less inhalation hazard to mixers Furthermore in some embodiments, "WSP" or "water soluble pouches" for example, MERIT®SOLUPAK® INSECTICIDE, Solupak 50% Wettable Powder in Water Soluble Packets, and the like, are contemplated for use in coating and spraying topdressing formulations of the present inventions. Water-soluble pouches in general contain an A.I. formulation in a pre-measured amount that when water comes into contact with the pouch, the pouch material dissolves and releases the pre-measured A.I. formulation.

Thus in another embodiment, the formulation is an emulsifiable concentrate for coating or mixing with a sand particle. These compositions are prepared by dissolving the agricultural chemical and an emulsifying agent in a solvent, such that solvents may be inorganic or organic. Inorganic solvents are usually not soluble in water; therefore, an emulsifier may be used so that the three or more chemicals will produce an emulsion spray when mixed with water.

In some embodiments, the inventors contemplate the use of microencapsulated concentrates in compositions of the present inventions. For example, microencapsulated pesticide or fungicide particles comprising an active ingredient (liquid or dry) would be surrounded in a plastic coating for mixing with water or ethanol and applied as spray or liquid for coating a sand particle or mixing with a topdressing material. The encapsulated A.I. would be released, quickly or slowly depending upon the type of encapsulation, following application. Advantages of using microencapsulated A.I.s would be to further increase safety to the human applicator, easy to mix, handle and apply; controlled release of active ingredient.

In some embodiments, the inventors contemplate the use of dusts in the compositions of the present inventions as ready-to-use dry formulations that contains a low percentage of the active ingredient plus a dry, inert carrier (talc, chalk, clay, ash, etc.). Advantages of using dusts include low concentrations of toxic A.I. amounts, usually ranging from 0.12 to 20% of weight within a diluent. Diluents or dust carriers are typically talcs, clays or diatomaceous earth. Sometimes wheat flour or powdered nut hulls are used as diluents for special purposes.

In another embodiment, the formulation is a granular composition (GR). In some embodiments, the inventors contemplate the use of granule or pellet ready-to-use dry formulations of A.I.s in the compositions of the present inventions. In general, pellets are larger and more uniform in shape than granules. Granular compositions in general are primarily soil treatments and may be applied either directly to the soil or over plants. When applied over plants, tend granules fall through the foliage to the soil. Some granules are applied to water either directly or over foliage. Since the granules do not adhere to the foliage of most plants, phytotoxicity and residue problems are reduced. However new types of granular compositions are contemplated comprising foliage efficient concentrations for sticking to foliage and delivering an A.I. prior to when the granule falls onto the soil. Since granules are typically prepared in advance prior to application, the active ingredient as a smaller granule, i.e. dust and the like, is contemplate to be attached to a carrier by spraying the granules onto the carrier, i.e. sand, and then drying the composition, binding the granule to the carrier with a binding or adhesive material, and the like. In treating granules with an active ingredient, a rotating drum-type blender may be used.

B. Additional Compounds for Use in Formulations of the Present Inventions.

For purposes of this invention, further exemplary embodiments of compositions of the present inventions comprising additional protectants and beneficial ingredients including but not limited to attractants, baits, herbicide safeners, anti-dessicants, antitranspirants, frost prevention aids, inoculants, dyes, brighteners, markers, synergists, pigments, UV protectants, antioxidants, leaf polish, pigmentation stimulants and inhibitors, surfactants, moisture retention aids, molluscicides (e.g., slugs and snails), nematicides, rodenticides, defoliants, desiccants, sticky traps, and IPM (integrated pest management) lures. In some embodiments, multiple active agents are readily formulated within a given formulation, for example, multiple active agents may include two or more of any of the following, fungicides, fertilizers, pesticides, herbicides, and any type of active ingredient or class of active ingredient, present and future.

The inventors also contemplate compositions of the present inventions comprising, pesticides including animal and bird repellants, attractants, baits, herbicide safeners, anti-dessicants, antitranspirants, frost prevention aids, inoculants, dyes, brighteners, markers, synergists, pigments, UV protectants, antioxidants, leaf polish, pigmentation stimulants and inhibitors, surfactants, moisture retention aids, humic acids and humates, lignins and lignates, bitter flavors, irritants, and malodorous ingredients, molluscicides (e.g., slugs and snails), nematicides, rodenticides, defoliants, desiccants, sticky traps, and IPM lures, chemosterilants, plant defense boosters (harpin protein and chitosan) desiccants (may also be used as a harvest aid), and other beneficial or detrimental agents applied to plant or other surfaces. Additional exemplary active ingredients include phosphites, and related plant stress reduction compounds and biostimulants, many of which are absorbed through foliage of grass plants.

The inventors further contemplate compositions of the present inventions comprising active ingredients such as dew control compounds for reducing the amount of moisture on foliage. Reducing the moisture on foliage should also reduce fungal growth and reduce other types of pathogens. The use of dew control compounds include surfactants comprising monoethanolaminedodecylbenzene sulfonate and nonylphenoxypoly-(Ethyleneoxy) ethanol, siloxane copolymer, etc. compositions of the present inventions comprising active fertilizers, as described herein and in the Examples.

The inventors also contemplate compositions comprising sand and plant growth regulators (PGRs), which are often applied to highly managed, cool-season turfgrasses every few weeks throughout the growing season to reduce clipping production, increase sward density, reduce seed head formation and enhance sward color (Lickfeldt et al., 2001, Agron J. 93:1164-1168, herein incorporated by reference). In additional embodiments, the inventors contemplate compositions of the present inventions further comprising plant growth regulators such as trinexepac-ethyl, maleic hydrazide, gibberellic acid, gibberellins, cytokinins, benzyladenine, glycines, quinolenes, phosphoric acid compounds, organic carbamates, quaternary ammonium compounds, acetamides, ethychlozate, azoles, paclobutrazol, anilides, pyradazidine, pyrimidines, napthaleneacetamide, phthalmides, phenoxies, pyrimidines, hybridizing agent, biostimulants, seaweed extracts and herbicides (typically at low use rates), phthalmides, phenoxies, and organic or carboxylic acids (e.g. gamma amino butyric acid and L-glutamic acid, naphthalene acetic acid, clofencoet, sintofen, nicotinic acids).

In additional embodiments, the inventors contemplate compositions of the present inventions further comprising mulches. Mulches in general are layered on to the soil surface to suppress weeds, conserve moisture, improve its visual appearance and minimize erosion. Alternative mulches include organic materials such as animal manure, compost, leaf mould, bark chippings, shredded prunings, and compost. Additionally, the inventors contemplate using a "peat alternative" in addition to or to replace mulch, for example, cocoashell, and the crushed shells of cocoa beans (*Theobroma cacao*) that are a by-product of the chocolate industry. Inorganic mulches contemplated for use include but are not limited to pebbles, sand, gravel, blanket mulches, polythene sheets, carpet, newspapers and even cardboard.

In additional embodiments, the inventors contemplate compositions of the present inventions further comprising compost. The inventors further contemplate the use of soir as an alternative to peat or in combination with peat.

Areas of turf lacking live plants or comprising dying plants may have hydrophobic soil where additional benefits of delivering compositions of the present inventions including wetting agents. For example, localized dry spots or patches formed by dollar spot fungal infections in turf are likely to become a serious turf management problem during the summer months, especially during periods of drought. Despite frequent irrigation, the soil in these spots resists wetting, resulting in even larger patches of dead or severely wilted turf. The applied water wets the dying and dead turf but does not adequately penetrate the soil surface to reach the root zone.

So, although soils in general absorb water, certain soils may be or are water repellent; a soil wetting agent would be added to the spray solution. Certain soils, in particular sandy soils, soils high in organic matter and potting mixes are the most likely to become hydrophobic resulting in excluding the liquid A.I. from entering the soil. When these types of soils are watered, such as with a sprinkler or hose, the water merely rolls off and is poorly absorbed where it is needed. Exemplary soil wetting agents are design to overcome water repellence for allowing the A.I. to enter the soil. Soil wetting agents are granular products and liquid products. Granular products tend to be easier to use than liquid products, especially in greenhouses because they can be readily incorporated into potting mixes. With granular products, the soil wetting agent is incorporated into granules of either clay or organic material such as coir. The wetting agent is then leached out gradually whenever the granules are watered or when it rains. Soil wetters help to overcome the effects of waxy organic coatings on the surface of the soil and the surface of organic matter so allowing the water to penetrate and be absorbed. Thus the inventors further contemplate preferred embodiments comprising a wetting agent. For purposes of this invention, soil wetting agents (including water absorbents) include ionic and nonionic surfactants. Active ingredients include alkoxylated polyols, poloxalene, 2 butoxyethanol, gleucoethers, propoxylated polyethylene glycols, polyoxyethylene ester of cyclic acid, polyoxyethylene ether of alkylated phenols, tri-ethanolaminedodecyl benzene sulfonate, C9-C10-C11 alcohol 6 EO ethoxylate, acrylamide potassium acrylate copolymer, polydimethylsiloxane, kelp extract, dehydrooxyrane, epihydrin, polyhydroxyethyl alkoxy alkene oxides, propylene oxide, ethylene oxide, et cetera.

In additional embodiments, the inventors contemplate compositions of the present inventions further comprising gypsum and the use of "clay-breaking" products that affect the chemical composition of the soil so that particles clump together and create pore spaces through which water and air can move. These substances may be added individually or together.

In additional embodiments, the inventors contemplate compositions of the present inventions further comprising extenders, that is, liquid solvents, liquefied gases under pressure, and/or solid carriers, optionally with the use of surface-active agents, that is emulsifying agents and/or dispersing agents, and/or foam-forming agents. When using water as an extender, organic solvents can, for example, also be used as auxiliary solvents. Suitable liquid solvents include aromatics, such as xylene, toluene, or alkylnaphthalenes, chlorinated aromatics or chlorinated aliphatic hydrocarbons, such as chlorobenzenes, chloroethylenes, or methylene chloride, aliphatic hydro carbons, such as cyclohexane or paraffins, for example, mineral oil fractions, alcohols, such as butanol or glycol as well as their ethers and esters, ketones, such as acetone, methyl ethyl ketone, methyl isobutyl ketone, or cyclohexanone, strongly polar solvents, such as dimethylformamide and dimethyl sulfoxide, as well as water. Suitable liquefied gaseous extenders or carriers include liquids that are gaseous at ambient temperature and under atmospheric pressure, for example, aerosol propellants, such as halogenated hydrocarbons, as well as butane, propane, nitrogen, and carbon dioxide. Suitable solid carriers for extenders include ground natural minerals, such as kaolins, clays, talc, chalk, quartz, attapulgite, montmorillonite, or diatomaceous earth, and ground synthetic minerals, such as highly disperse silica, alumina and silicates. Suitable solid carriers for granules include crushed and fractionated natural rocks such as calcite, marble, pumice, sepiolite, and dolomite, as well as synthetic granules of inorganic and organic meals, and granules of organic material such as sawdust, coconut shells, maize cobs, and tobacco stalks. Suitable emulsifying and/or foam-forming agents include non-ionic and anionic emulsifiers, such as polyoxy-ethylene fatty acid esters, polyoxyethylene fatty alcohol ethers, for example alkylaryl polyglycol ethers, alkyl-sulfonates, alkyl sulfates, arylsulfonates, as well as albumen hydrolysis products. Suitable dispersing agents include lignin-sulfite waste liquors and methylcellulose.

The inventors further contemplate compositions of the present inventions comprising In general adhesives contemplated for use in the present inventions refer to such compounds a carboxymethylcellulose and natural and synthetic polymers in the form of powders, granules or latices, such as gum arabic, polyvinyl alcohol, and polyvinyl acetate, as well as natural phospholipids, such as cephalins and lecithins, and synthetic phospholipids, can be used in the formulations.

In additional embodiments, the inventors contemplate compositions of the present inventions further comprising mineral oils and vegetable oils.

The inventors further contemplate compositions of the present inventions comprising synthetic acids including acid substances used to improve soil structure and flush bicarbonates and salts from the root zone.

The inventors further contemplate compositions of the present inventions comprising thatch reducers. Examples of thatch reducers include combinations of sea plant extracts, meals, microorganisms, etc., that purport to reduce thatch without cultivation.

In additional embodiments, the inventors contemplate compositions of the present inventions further comprising colorants such as inorganic pigments, such as iron oxide, titanium oxide, and Prussian Blue, and organic dyestuffs, such as alizarin dyestuffs and azo dyestuffs, and trace nutrients, such as salts of iron, manganese, boron, copper, cobalt, molybdenum, and zinc.

C. Turfgrass Plant Cultivars and Pathogens.

The inventors contemplate the use of compositions and topdressing vehicles of the present inventions for use with any type of turfgrass plant and areas of turf. In particular, the compositions of the present inventions may be applied to turfgrass plants such as Bermuda grass, creeping bent grass, perennial ryegrass, tall fescue, fine-leaf fescue, zoysia grass, et cetera. These turf grass plants include warm season grasses and cool season grass plants. These examples are not meant to limit the type of grass plant that would benefit from the formulations of the present inventions. Exemplary species and cultivars of turfgrass plants include but are not limited to Kentucky bluegrass, exemplary cultivars Adelphi, Bono, Enmundi, Midnight, Rugby, Admiral, Bristol, Estate, Mona, Sydsport, America, Brunswick, Freedom, Monopoly, Touchdown, Argyle, Challenger, Georgetown, Mystic, Trenton, Aspen, Cheri, Glade, Nassau, Victa, Banff, Columbia, Holiday, Nugget, Welcome, Barblue, Coventry, Majestic, Parade, Baron, Dormie, Merion, Plush, Bensun (A-34), Eclipse, Merit, Ram I, creeping bentgrass, exemplary cultivars CBentgrass, Mackenzie, Declaration, Authority, Shark, 007, Independence, Tyee, 13-M, Benchmark DSR, Bengal, zoysiagrass, exemplary cultivar Meyer, et cetera.

Further, areas of application include but are not limited to fairways, tees, putting greens, athletic fields, and lawns.

The inventors contemplate making and using compositions of the present inventions for preventing, reducing and eliminating pathogen infestations, including fungal infections, insect infestations, microbial infections, in addition to eliminating weeds and any type of treatment for improving the health of a turfgrass plant and use of an area of turf, such as increasing the playability of golf course turf treated with compositions and methods of the present inventions. Therefore, the inventors further contemplate preferred embodiments making and using compositions of the present inventions for reducing and eliminating dollar spot fungal infections of turf grass plants.

The inventors contemplate delivering compositions of the present inventions as preventative and curative means of managing areas of turf. The inventors contemplate delivering compositions of the present inventions as preventive treatments, for example the first application of top dressing in the spring, after long periods of rain, and the like. In particular delivering such compositions as curative treatments along with regular top dressing applications when turf grass managers observe signs of fungal infections, such as drying, dying, moldy, browning, graying areas of turf, or dark spots on turf foliage, and the like.

The fungus, *Magnaporthe poae*, causes summer patch disease. The disease begins as scattered light green patches 5 to 10 cm in diameter. These patches may grow as large as 1 meter in diameter as rings and circular patches of dead or dying turfgrass that turn dull-tan to reddish-brown, or yellow or tan areas up to 1 foot in diameter, consisting of dead and dying plants. The most diagnostic of these larger patches in turf may exhibit a "frog-eye" pattern. Distinct streaks, crescents, and circular patterns are found in the affected turf area. Roots, crowns, and stolons are affected by a dark brown rot. Young roots may appear healthy, although dark brown hyphae may be present on these tissues. Vascular discoloration and cortical rot occur in later stages of the disease. The fungus can survive as mycelia in plant debris or in host tissue. This disease was reported infecting red fescue, Chewing's fescue, hard fescue, perennial ryegrass, and creeping bent grass, but appears to be most destructive to annual bluegrass and Kentucky bluegrass plants. Therefore, the inventors further contemplate preferred embodiments making and using compositions of the present inventions for reducing and eliminating summer patch fungal infections of turf grass plants.

In even further embodiments, the inventors contemplate preferred embodiments comprising making and using compositions of the present inventions for reducing and eliminating snow mold diseases. Snow mold diseases, including grey and pink-crusted areas of grass in which the blades are dead, bleached and matted together. These crusted areas range from several inches to several feet across.

The inventors further contemplate preferred embodiments comprising fungicides for controlling and removing additional fungal infections including but not limited to *Fusarium* species, *Leptosphaeria korrae*, and Necrotic Ring Spot.

The inventors further contemplate preferred embodiments using an herbicide as an A.I. for reducing weeds. The inventors further contemplate preferred embodiments comprising a wetting agent.

The inventors contemplate that top dressing compositions of the present inventions contains distribution of the agricultural chemical throughout the top dressing. While it is appreciated that an agricultural chemical is optionally added to a large quantity of conventional top dressing and with sufficient mixing or agitation a homogenous distribution of the agricultural chemical through the top dressing occurs, preparation of a quantity of inventive composition needed to treat an area of several acres with conventional mixing equipment is both time consuming and of questionable quality. Owing to the different density of sand and the optional top dressing components of loam and/or peat, segregation and compositional sieving can occur during transport of an inventive top dressing prior to broadcast distribution. Additionally, handling of concentrated quantities of agricultural chemical often requires special skills and safety equipment. Therefore, the inventors further contemplate topdressing vehicles of the present inventions for use in delivering the formulations of the present inventions, as described herein.

III. Top Dressing Vehicles of the Present Inventions.

Specifically, the inventors contemplate "best mode" apparatuses as top dressing vehicles for delivering compositions and formulations of the present inventions, in particular a formulation comprising an A.I. and a top dressing material. In particular, the inventors contemplate a top dressing vehicle of the present inventions that combines a sand top dressing operation and a chemical application operation normally practiced on golf courses into one procedure.

The application of any active ingredient, such as a fungicide, to an area of land with conventional spray equipment is prone to numerous problems. For example, the application of pesticides with conventional spray equipment for liquid applications is prone to numerous types of environmental problems due to spills, which contaminate land and ground water, particularly near wellheads where water is drawn for human and animal consumption, and used for dilution of tank mixes for a variety of chemical applications. In particular, when spraying liquids, liquids form aerosols and are prone to cause spray drift issues. Spray drift contaminates neighboring land, crops, waterways, etc.

For many embodiments of the present inventions, the inventors contemplate numerous advantages for spraying top dressing materials. In particular, applying a liquid formulation onto a top dressing composition of the present inventions would not present drift problems since top dressing particles settle out of the air quickly, unlike aerosols. Even further, in another embodiment, the inventors contemplate spraying particle formulations onto top dressing materials using top dressing vehicles of the present inventions. Further advantages of using and delivering solids as in the compositions and methods of the present inventions are to overcome problems with application of pesticides with conventional spray equipment. Conventional spraying is prone to worker safety problems due to skin exposure, inhalation, etc., which is not as severe with dry applications. These types of advantages are also provided by using granular top dressing compositions of the present inventions since they are heavier than a liquid spray alone.

The inventors contemplate that 'on-the-go blending' and simultaneous mixing and application technology as described herein would also solve the problem of leftover spray mix when using traditional spraying methods. Normally, such leftover 'tank mix' is wasted, used improperly, disposed of improperly, and the like, which creates waste. Further, liquid left in the spray tank often leads to adverse changes in the chemical components due to salting out, corrosion, or chemical/microbial decomposition. In contrast, the inventors discovered the methods of the present inventions reduce left over spray.

Further, there is a public relations concern associated with the sight of sprayers operating nearby to living spaces, recreation areas, schools, etc. whereas granule applications such as applications of sand do not raise as much concern.

In summary, the application of pesticides with conventional spray equipment is prone to environmental problems due to spray drift, which contaminates neighboring land, crops, and spills, which contaminate land and ground water, waterways, particularly near wellheads where water is often drawn for dilution of tank mixes. etc., whereas the inventors contemplate that spray compositions of the present inventions and granular compositions do not present drift problems since particles quickly settle out of the air.

Unrelated to the problems with traditional spray and granular A.I. applications, some of which are described herein, the inventors also discovered during the course of development of the present inventions, that the majority of commercially available top dressing vehicles were found in general to lack the capability to efficiently apply topdressings to golf course turfs. Thus not only do the inventors contemplate significantly modifying currently available top dressing vehicles for use with the present inventions, they further contemplate the design and use of top dressing vehicles for more efficient application of topdressing and topdressing formulations of the present inventions while minimizing damage to turf areas at point-of application and reducing the cost of maintaining turf grass areas, including but not limited to golf course turf.

Previous attempts were described or made to solve some of the problems related to using conventional machines for the application of top dressing. In particular, although broadcast spreaders are known for spreading seed and fertilizers, broadcast spreaders did not widely penetrated the top dressing market until the introduction of the broadcast spreading top dresser of the type of U.S. Pat. No. 6,149,079, herein incorporated by reference. In particular, the majority of commercially available broadcast spreaders utilized mesh type conveyors having hinged links that are formed from metal or similar material. These hinged links form an array of cells open at the top and bottom. These hinges would allow materials such as sand to fall through the conveyors rather than be conveyed. Additionally, such previous broadcast spreaders were often driven by the power take off of the towing vehicle, with the spinners and conveyor being driven together. This increases the power demands on the towing vehicle. Further, with previous broadcast spreaders, material was often present on the spinners at initiation of spinner rotation. This material may initially be dispensed in a clump or, at a minimum, may initially be distributed at a rate greater than under normal operating conditions. Thus, previous commercially available broadcast spreaders required a towing vehicle of considerable power and including a power take off, dispensed material in an amount greater than desired in a top dressing application and unevenly at least at the start of spinner operation. These types of top dressing vehicles would be problematic for obtaining optimal applications of compositions of the present inventions.

Top dressers of the broadcast spreading type disclosed in U.S. Pat. No. 6,149,079, herein incorporated by reference, have penetrated significant portions of the top dressing market. In particular, considerable market success has been experienced by the top dressers of the type of U.S. Pat. No. 6,149,079, herein incorporated by reference because of their ability to spread top dressing over wide areas while avoiding the problems and deficiencies of previous commercially available broadcast spreaders.

However, top dressers of the type of U.S. Pat. No. 6,149,079, herein incorporated by reference, were unable to dispense top dressing at heavy rates equivalent to that with top dressers of the drop type. Prior attempts to dispense top dressing with spinners at heavier rates utilized shrouds such as of the type disclosed in U.S. Pat. No. 4,032,074, herein incorporated by reference, which in some cases were moveable between operable and nonoperable positions. However, such shrouds basically stopped the kinetic energy of the top dressing material being propelled radially by the spinners and deflected the material downwardly in a controlled configuration, much like a drop-type topdresser. Thus, it should be immediately appreciated that the width of the dispersed material perpendicular to the operation direction is then a function of the angle of the sides of the shroud, that the beneficial effect of radial propulsion by the spinners is lost, and in the case of most powered spinners, did not result in even distribution. Therefore, turf managers who owned top dressers of the broadcast spreading type also were required to purchase top dressers of the drop type to perform both light and heavy applications of top dressing in order to compensate for the uneven applications of topdressing from the spinner-type machines.

Particularly and specifically for heavy applications, the distribution pattern for materials distributed by one or more spinners of a broadcast spreader is often uneven. The distribution of material can be uneven along either or both the direction that the broadcast spreader is moving and the width perpendicular to the direction that the broadcast spreader is moving. Controlling the distribution of material along the direction that the broadcast spreader is moving is typically controlled by a combination of spinner configuration, broadcast spreader ground speed and spinner velocity. However, controlling the distribution of material from a powered broadcast spreader perpendicular to the direction that the spreader is moving has not been satisfactorily addressed by prior broadcast spreaders. Thus, prior broadcast spreaders have continued to generate an uneven depth of material perpendicular to the direction of the broadcast spreader's movement. Generally, the uneven depth is an artifact of loading the material at a particular location on the spinner. The placement of material at a particular position on the spinner will inherently concentrate the distribution of that material within a particular radial arc about the axis of rotation of the spinner. The particular radial arc is determined by the configuration of the spinner and the speed that the spinner is rotating. Providing multiple spinners typically merely changes the distribution profile across the perpendicular and, typically, results in an uneven distribution profile across the perpendicular. Thus spinner type machines that are capable of distributing even layers of top dressing material would be preferred for use in the present inventions Finally, none of these devices comprises compositions and methods for point-of-application liquid coating of top dressing materials.

A. Providing Top Dressing Vehicles of the Present Inventions.

The inventors show a need for providing a top dressing vehicle capable of use in the present inventions. The inventors contemplate top dressing vehicles for combining individual chemical applications and top dressing applications, individual operations normally practiced on golf courses, into one procedure by providing a new type of top dressing vehicle comprising, a topdressing vehicle and a chemical spray unit, i.e. sprayer. This combination of operations was contemplated to be accomplished in its simplest embodiment, by attaching a chemical spray nozzle to a commercially available topdressing vehicle. Exemplary top dressing vehicles, in addition to those described herein, include but are not limited to those described in Topdressers, such as those disclose in exemplary U.S. Pat. Nos. 5,307,952, 4,438,873, 5,307,952, 5,287,999, 6,149,079, 6,932,286 and United States Patent Applications Nos. 20030155453, 20030089805, 20030098373, and 20060006256, each of which are herein incorporated in their entirety. In a further embodiment, a sprayer unit comprising a tank, pump, valves, compressor unit, spray nozzles, in addition to any component compatible with the function of a sprayer unit, are mounted onto top dressing vehicles, such as exemplary finishing brush drop-type topdressers and spinner-type topdressers, both of which are currently commercially available. Commercially available topdressing vehicles do not have any type of attachment for spraying a substance, such as a liquid or solid, onto a top dressing material. Even further, none of the commercially available top dressers were designed for use in blending toxic chemicals with top dressing materials. Even further, none of the commercially available top dresser vehicles were designed for applying or delivering toxic chemicals. Thus the inventors further contemplate embodiments of top dressing vehicles that are specifically designed for use with solid and liquid forms of chemicals. In yet further embodiments, the inventors contemplate making dedicated top dressing vehicles of the present inventions comprising spryer units for incorporating embodiments as described herein for new types of commercial top dressing vehicles.

The inventors further contemplate embodiments of top dressing vehicles that are specifically designed for optimal weight distribution over tire area to protect turf. In additional embodiments, the inventors contemplate top dressing vehicle comprising flow adjustor units for automatically calculating and adjusting the flow rate from either the nozzles or directly released by a flow valve in between a tank and hose leading to the nozzles. Specifically the amount of sprayed formulation and volume of top dressing material vs. forward speed of the machine. Further contemplated is downsizing the sand bin of current vehicle designs, providing more area available for attaching a sprayer unit. See for example a Dakota 440, see, FIG. 9. Thus a top dressing vehicle of the present invention would have a similar size and weight of current top dressing machines while incorporating the weight of filled spray tanks and a sprayer unit with the additional function for providing a sprayed material for delivering to an area of turf.

The inventors contemplate in one embodiment, applying a concentrated spray solution to a top dressing material, in particular sand, through commercially available spray nozzles mounted just above a conveyor belt that carries sand from a bin to the finishing brush or to the spinners, depending on the type of top dressing vehicle. In either configuration, the sand would be treated just prior to being spread on the turf as a moist material. As the sand exits the machine, mixing of the treated sand with any remaining untreated sand would occur so that an active ingredient (A.I.) is applied evenly across the turf treated with the swath of sand. The inventors contemplate adjusting volume and spread width of sand, such as the adjusting capability of certain current topdressers, for example, a Dakota 440 with a control means for adjusting application parameters.

Further, in one preferred embodiment of the present inventions, the top dressing material is pre-coated by a top dressing vehicle comprising a conveying means for dispensing the top dressing material, and a means for spraying top dressing during dispensing. In one embodiment, the means for spraying is a sprayer, comprising a tank, pump, valves, hose, nozzle and means for moving the formulation from the tank, through the hose, optionally into a pipe and ending at a nozzle for evenly spraying the formulation onto the top dressing material. In a preferred embodiment, the top dressing vehicle is capable of spraying a top dressing material, such as sand, with formulation as the sand moves along the conveyer means, just before it drops onto the turf or is spun out/broadcast onto an area of turf. Examples of a means for moving the formulation include but are not limited to hydraulic and electrical units.

In one preferred embodiment of the present inventions, a top dressing vehicle of the present inventions provides a wet top dressing material coated with a formulation comprising an AI. In one further embodiment, the coated top dressing is conveyed, such as by an elevator unit, into a topdresser vehicle as moist material. Further, in one embodiment, the wet coated top dressing is applied by the topdresser vehicle as a moist material to an area of turf. In one preferred embodiment the wet material is dispensed using a spinner unit of a top dressing vehicle. In one preferred embodiment, the moist material is dispensed using a finishing brush unit of a topdresser vehicle.

In another embodiment, the coated moist top dressing material undergoes drying prior to application to an area of turf. In another further embodiment, the coated top dressing is conveyed onto a surface for drying. Drying may be done in several ways, such as drying the coated material in an onsite kiln, spreading the material out on the ground or on a drying surface, such as concrete or plastic, for air drying, and by adding a drying ingredient for removing the moisture from the coated top dressing material.

Specifically, the inventors contemplate advantages of top dressing vehicles of the present inventions, in other words a two-in-one sprayer/topdresser design over the current practices and top dressing devices without spray attachments include: 1) less damage to golf course turfs as two trips over the turf (spraying and top dressing) with heavy equipment are reduced to one trip, 2) savings in time and labor costs, 3) less interruption of play, and 4) reduced golfer anxiety as the pesticide/fertilizer applications are concealed in a sand application.

Further, the inventors contemplate advantages of top dressing vehicles of the present inventions as two-in-one sprayer/topdresser design over the recently developed and marketed granule/sand blending machine include: 1) a greater number of A.I.-treated particles being distributed to the turf, 2) better distribution of A.I. over the spread swath because no particle mass (weight) differences exist between the heavier sand and the lighter chemical granules, 3) the ability to use moist/wet sand (cost savings) without fear of "gumming up" the equipment or sand due to dissolving particles, 4) time, equipment, and labor savings because the blended granule/sand material does not have to be loaded into a standard topdresser for application, 5) lower equipment costs because a separate topdresser is not required, 6) the ability to adjust sand application volumes at will without affecting the rate of chemical/fertilizer application, and 7) no left-over treated sand product to store or dispose of, and 8) potentially greater selection of A.I.s that could be sprayed on the sand.

Even further contemplated advantages of making and using top dressing vehicles of the present inventions as two-in-one sprayer/topdresser designs and applications over the pre-treated and dried sand of conventional applications include: 1) time, labor, and equipment cost savings in the preparation of the treated sand, 2) less worker exposure during the preparation and application procedures, 3) the ability to use wet or dry sand of any type and in any application volume, 4) reduced equipment costs compared to treating and drying sand, 5) no shipping costs to get the treated sand to the end user, 6) time, labor, and equipment cost savings in the application.

B. Providing Top Dressing Vehicles of the Present Inventions.

The inventors further contemplate a top dressing vehicle with fan adjustable foam-marking boom to allow the operator to locate the edges of the throw pattern. This will prevent skips and over-laps, which result in either untreated or damaged turf. Spinners that require 100% overlap greatly reduce skips and overlaps. Additionally, as currently available on some commercial sprayers, spray volume could possibly be correlated with ground speed to increase/reduce spray volumes to the sand to adjust for increased/decreased ground speeds. This unit could be used to apply virtually any materials that can be sprayed on golf course turfs.

The inventors contemplate methods of providing a top dressing vehicle of the present inventions by attaching sprayer units to currently commercially available topdresser machines. In further embodiments, the foam marking units would be supplied and attached to specially designed top dressing vehicles of the present inventions. The inventors contemplate devices for combining the chemical applications and sand top dressing applications normally practiced on golf courses into one procedure by mounting a chemical spray tank, pump, spray nozzles, etc., onto finishing brush drop-type topdressers and spinner-type topdressers, both of which are currently commercially available. Exemplary topdressers/machines include but are not limited to the following vehicles. As described herein, the inventors contemplate attaching sprayer units onto topdressing vehicles for providing and using formulations of the present inventions. In one embodiment, a topdresser vehicle is a brush drop-type topdresser machine. Exemplary finishing brush drop topdresser machines are also shown in the Figures and described herein in the Examples.

In a preferred embodiment, a topdresser vehicle is a spin-type top dresser vehicle. An exemplary BTD-05 Bannerman Ultra Spin Topdresser has dual hydraulically driven disks that broadcast top dressing material to various widths. Maximum spread width ranges between 12-20 feet, and the literature indicates a capability of spreading, sand, peat, top dressing mix, rock salt and grit. With a holding capacity of 1.5 cu. Yds of material, listed with a capacity to be calibrated to achieve cost control of the materials to be spread prior to dispensing, powered by tractor hydraulics or an optional engine drive hydraulic power pack, a "Walking-beam axle" such that tires never leave the turf surface, in particular treadless turf tires providing a consistent pressure of only 10-12 p.s.i. on the surface, in addition to a variable-speed conveyor floor (see, at world wide web.sportsturfmagic.com).

Another exemplary top dressing spinner machine as shown in the Figures is commercially available from Dakota Sand and Peat and contemplated for use in the present inventions. The inventors contemplate the use of a Dakota Peat & Equipment 440 that has an eight cubic foot blender option for the Dakota 440 Turf Tender that allows superintendents to blend materials on site. Thus, in one embodiment, the sprayer is mounted over the axle, on the left side of the Dakota 440 (opposite side of the side conveyor) and other spinner-type topdressers, with a nozzle(s) mounted over or beside the sand conveyor belt at the rear of the machine, just above, and in front of the spinners. The Dakota 440 has a long, open sand belt area just before the sand falls onto the spinners. If the nozzle was mounted directly above the belt, an even-pattern flat fan band spray nozzle with a capacity of 1 gallon/minute (Ex.: Tee Jet 8010E or 1110E) to 1.5 gallon/minute (Ex.—TeeJet 8015E or TeeJet 11015E) would deliver sufficient spray volume to apply a 10-15 gallon/acre (GPA) spray volume to sand being applied to 4048+sq. ft. in a 20 ft. swath traveling at 2.3 MPH in a 1 minute duration.

In one embodiment, the nozzle(s) are mounted above and to the side of the sand belt at the rear of the machine (as an example, the Dakota 440 has 2 ideal locations for mounting nozzles, see, Figures). An off-center, directed band spray nozzle could possibly be used, with a TeeJet OC12 or OC16 nozzle delivering 1.0-1.5 gallons/minute to the sand on the conveyor belt. Off-center nozzle tips apply an even band of spray below, and off to the side of the nozzle itself. The number and size of nozzles used may depend on various factors such as travel speed, swath width; sand volume applied and desired GPA. Some flexibility could be achieved through the use of a rotating spray head, which might contain 3 or more individual nozzles of various capacities. The operator (or computer) would simply rotate the spray head to utilize the appropriate spray tip for the speed of travel, swath width, and desired sand volume. Rotating spray heads already in use on spray booms for agriculture uses are contemplated for use with top dressing vehicles of the present inventions.

In another embodiment, the inventors contemplate using a sprayer mounted onto a top dressing vehicle comprising a conveying means and a blending means. Thus one example, a blending means is a mechanical blender capable of mixing a top dressing material, such as sand, with another solid material, such as peat, compost, and the like, prior to application of a spray formulation. An exemplary vehicle applicable to the present invention comprising a conveying means and further comprising a blending means, and even further comprising an elevator attachment, is a Dakota 440 Blender (Dakota Sand and Peat Company). The Dakota 440 Blender is a sand/granule blender trailer machine that deposits the blended product into a traditional topdresser, via the elevator, for application to the turf. These blended granules may be impregnated with pesticides, plant growth regulators, fertilizers, etc. However these machines do not have a spray attachment or a means for spraying a formulation onto a top dressing material. The inventors contemplate that any vehicle comprising a conveying means is application to the present invention. In another preferred embodiment the inventors contemplate spraying a formulation onto a top dressing material and using a conveying means such as an elevator of an exemplary Dakota 440 Blender machine to convey coated top dressing material into a top dressing machine for distributing the moist material onto turf or for dropping the material onto the ground while the Dakota 440 Blender machine is stationary or moving.

The inventors further contemplate that any type of compost blending machine is applicable for use in the present inventions for attaching a sprayer.

C. Embodiments of Sprayer Units for Attaching to Top Dressing Vehicles.

In general, any type of sprayer unit capable of dispensing liquids or powders is contemplated for use in the present inventions. Basic components of sprayer units include but are not limited to desired combinations of tanks, valves, hoses, nozzles, pumps, compressors, strainers, couplings/fittings, wands, controllers, regulators, et cetera.

1. Sprayer Units.

In preferred embodiments sprayer unit parts are contemplated for attachment to top dressing vehicles. Various means of attachment are contemplated, however any means for attaching a sprayer unit, including but not limited to attaching any individual sprayer part, directly and indirectly, are included. Examples of means for direct attachment of a sprayer unit and/or parts includes but is not limited to c-clamps, tape, clip on parts, such as clip on spray nozzles (United States Plastic Corp., Lima Ohio), U-bolts and the like. Examples of means for indirect attachment of a sprayer unit and/or parts includes but is not limited to welding tank holders, tank clamps, pump clamps, hose clamps, nozzle clamps, bars, booms, etc., onto top dressing vehicles. Further means for indirect attachments include any means for bolting, screwing, etc. and a sprayer unit onto a top dressing vehicle.

Attachments may be permanent, such as built in, for example, a nozzle spring clamp is welded to a top dressing vehicle, tank holding clamps or straps, hose clips, are bolted onto a top dressing vehicle, and the like. In other embodiments, attachment is temporary, for example, taping a sprayer part onto at top dressing vehicle, such as a nozzle, hose, and the like. In other embodiments, the sprayer unit is a detachable unit. For example, a sprayer unit comprising any of the sprayer parts, such as a tank and pump, may be readily detached from a top dressing vehicle. Alternatively, a detachable sprayer unit may be readily attached to top dressing vehicle using indirect permanently attachments to the top dressing vehicle. Thus in another embodiment, the attached sprayer unit may be configured as a detachable unit.

Thus in one embodiment, a sprayer unit is contemplated for attaching to either side or both sides of the top dressing hopper on the spinner-type machines and on the front hitch area for the drop-type topdressers. Such that in another embodiment, the top dressing vehicle comprises permanently attached nozzle clips.

However, for other embodiments, a sprayer unit is contemplated for use as an unattached unit, where the nozzle is attached to the top dressing vehicle. For example, a hand-held sprayer unit sprays through a nozzle attached to a top dressing vehicle. In some embodiments, the unattached unit is a hand-held sprayer. In other embodiments, the sprayer is used as an unattached unit for providing a composition of the present inventions. In some embodiments, the nozzle used with an unattached unit is a hand held wand. In other examples, the nozzle is attached to the top dressing machine. For example, in one embodiment, a sprayer unit is contemplated for use mounted on a flatbed for use in the present inventions. The flatbed may be mobile or immobile. A mobile flatbed would find use with smaller topdressing vehicles where the extra weight of the sprayer unit and liquid chemicals would harm the turf due to compaction. In another embodiment, the flatbed is mobile for moving along with the top dresser vehicle, wherein the nozzles are attached to the vehicle. In another embodiment, the flatbed is immobile, for use in coating a topdressing material prior to application. In a further embodiment, the immobile flatbed finds use for coating topdressing material provided by a blender type topdressing vehicle, such as a Dakota 440, wherein the nozzle(s) are attached to the topdressing vehicle.

The inventors contemplate the use of any suitable chemical tank for use in the present inventions. Exemplary tanks are provided by the tank size, such as 10, 20, 30, 40, 50, 80-gallon tanks. The optimal size of the tank is a small tank, such as a 5, 10, and 20 up to a 50-gallon tank. However the optimal tank size for the vehicle will depend on several variables including but not limited to the concentration of the spray formulations (gallons/acre) intended for use, the weight of the topdresser, and how much sand the superintendent intends to deliver as regular treatments.

Tank sizes are contemplated to match certain factors as follows. On the spinner type machines, the spray area is typically a 10"-12" conveying means, i.e. belt, with a range of swath widths from 12'-36' such that a 1×-3× spray volume tank capability is contemplated to accommodate these ranges. By adding in variables such as various ground speeds, it becomes apparent that volume adjustments, such a flow adjusters, are necessary.

In the examples, the inventors are delivering the sand at the low end of the recommended amount, such as those quantities recommended by an acknowledged expert (Beard, J. B. 1982. Turf Management for Golf Courses p. 144, Burgess Publishing Co, Minneapolis; Beard, J. B. (and The United States Golf Association) 2002. Turf Management for Golf Courses, second Ed, Ann Arbor Press. p. 159 and Table 3.1, Ann Arbor Press, Chelsea, Mich., herein incorporated by reference). However the inventors contemplate other amounts for delivering top dressing as recommended in Beard (Beard, J. B.

1982. Turf Management for Golf Courses p. 144, Burgess Publishing Co, Minneapolis; Beard, J. B. (and The United States Golf Association) 2002. Turf Management for Golf Courses, second ed., Ann Arbor Press. p. 159 and Table 3.1, Ann Arbor Press, Chelsea, Mich., herein incorporated by reference).

Thus in the compositions of the present inventions, the amount of spray applied was 9 gallons/acre, on the low end of recommended amounts based upon the average concentration of commercially available chemicals, however the inventors contemplate even further lowering of the amount of liquid necessary for a treatment, up to 50%, or greater. Such that, using a 9 GPA spray solution, a spray tank with a 50-gallon capacity, would be the minimum size contemplated for the smaller topdressers of 1 cubic yard sand capacity, such as the Dakota 410 top dresser. At 9 GPA and the exemplary 1.1 cu. yd. sand/applied in the examples, this would allow for an estimated 5 re-fills of the sand hopper (covering 5.5 acres) for every refill of the spray tank. Another exemplary tank size calculation provided for the Dakota 440 with a 5 cubic yard hopper capacity, the estimated necessary tank capacity would be at least a 150-gallon tank at recommended A.I. concentrations. This would allow for 3 re-fills (for 13 acres of coverage) of the larger hopper 14, FIG. 10, for every spray tank 3, re-fill. For contemplated concentrated spray solutions, undiluted concentrates, the inventors estimate using a 5-gallon tank on small topdressers and a 15-gallon tank on the large units. In one embodiment, a tank is contemplated for mounting over the axle of a top dressing vehicle, for example on the left side of a Dakota 440 (opposite side of the side conveyor) and where appropriate on other spinner-type topdressers. However the inventors contemplate the use of larger tanks for applying and delivering A.I.s at current application rates.

However, on top dresser machines of the present inventions, where the sizes of the sand hoppers are contemplated for reduced sizes of sand hoppers in order to compensate for the extra weight of the spray unit, in order to avoid damaging weight compaction of turf, tanks on the smaller size, 50 gallons or less, are contemplated for use. The inventors contemplate reducing water volumes need in the tanks for the spray solutions, as far as possible while retaining efficacy, to provide an even coverage of A.I. to the topdressing, with no visible turf phytotoxicity after treatment of the grass plants, and without nozzle plugging during treatment. Tank size will also depend on what size the current topdresser designs will accommodate, thus the inventors further contemplate using custom contoured tanks, et cetera.

Figure 4E:
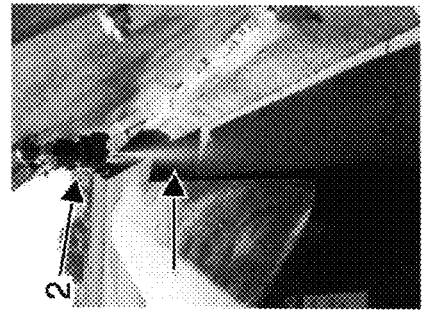
FIG. 4 shows an exemplary self-propelled brush drop-type topdressing vehicle 1, such as a 3 foot Meter-R-Matic™ Top Dresser, Turfco™, with A) two attached nozzles 2, hose 4, for spraying a topdressing material as it drops from the conveyor belt, B) showing another embodiment for an attached nozzle 2, hose 4, for spraying a topdressing material 7 where C) shows a close up view of the nozzle 2 placement, D) shows sand 7 being moved on the conveyor belt 8 while being sprayed using nozzles 2, further showing the type of spray pattern, black arrows, and E) shows a side view of an exemplary spray pattern/spray curtain, white arrow, sprayed from nozzles 2.
Figure 4C:
Figure 4D:
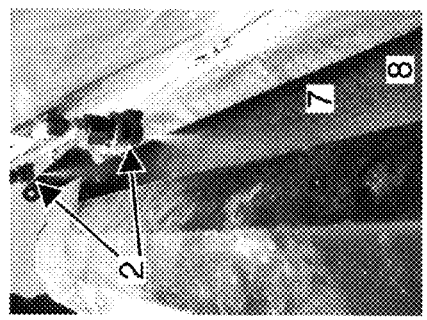
Figure 4A:
Figure 4B:
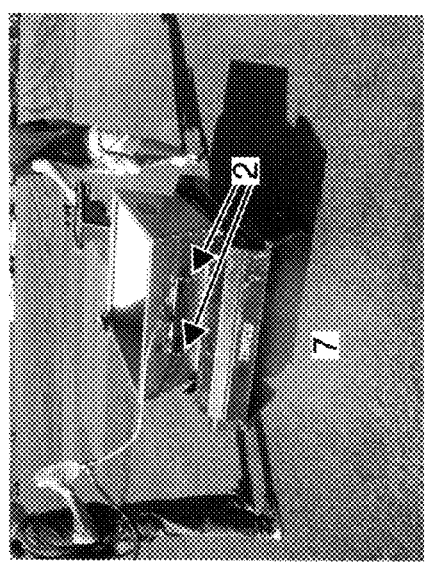
Figure 6B:
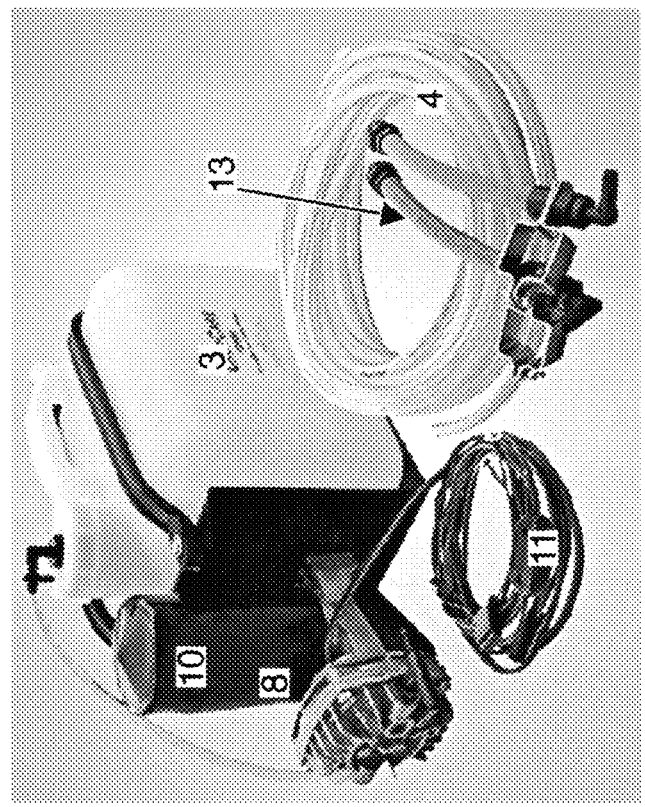
FIG. 6 shows an exemplary brush drop-type topdressing vehicle 1, also shown in FIG. 5, further showing A) an attached spray tank 3, hose 4, with a schematic of pump/compressor 10 and B) an exemplary foam marking unit comprising tank 3, hose 4, pump/compressor 10, electrical wiring 11 and outlet tube 13.
Figure 6A:
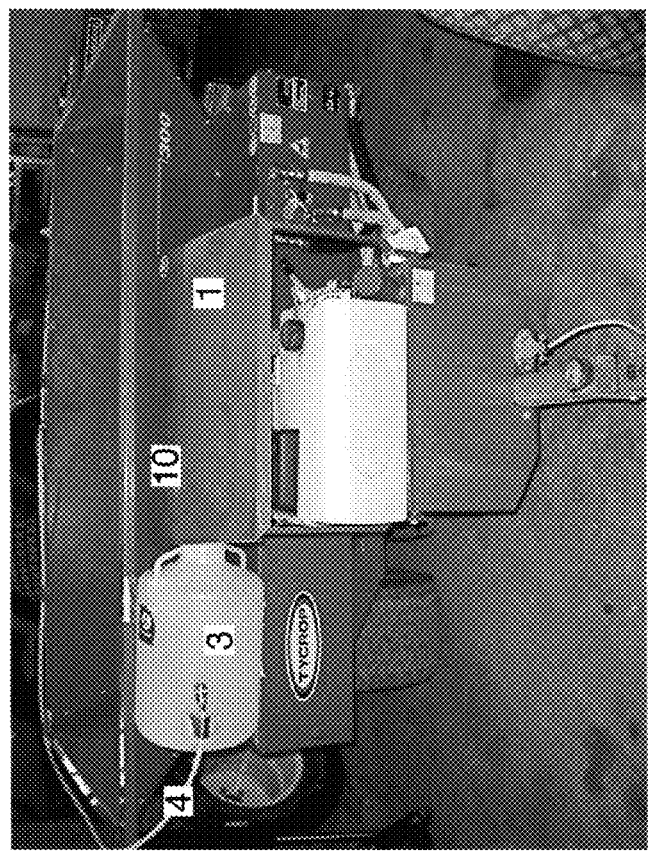
Figure 8C:
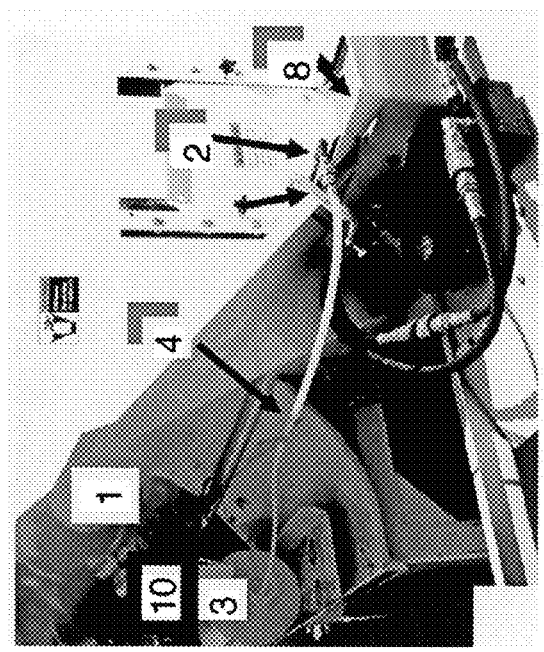
FIG. 8 shows an exemplary spinner topdressing vehicle 1 A) demonstrates a sprayer tank 3, compressor 10, hose 4 attached to vehicle 1, cover for spinner device 6 and dispensed top dressing 7, B) shows an exemplary attached off set nozzle 2 and hose 4, spinner device 6, and rear gate 12, while C) shows a conveying means 8 moving a topdressing material for coating 7 as regulated by a rear door 12, where a schematic of pump/compressor 10 is contemplated for attaching adjacent to tank 3, arrow points to c-clamp attaching nozzle 2, D) shows an exemplary attached off set nozzle 2 for spraying to a topdressing 7, amount controlled by rear door 12, being moved by conveyor 8, and E) showing an exemplary hose 4 leading to nozzle 2 (a 95006E flat fan nozzle for spraying a liquid curtain (marked by schematic lines)) attached above conveying means 8 as it was spraying fungicide onto sand 7, whose amount was controlled by gate 12, on the conveying means 8 prior to entering a spinner 6.
Figure 8A:
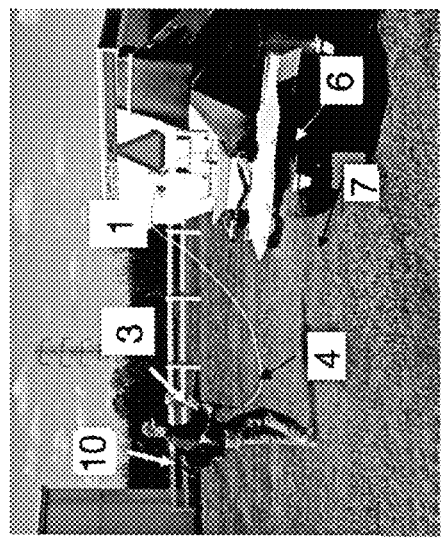
Figure 8B:
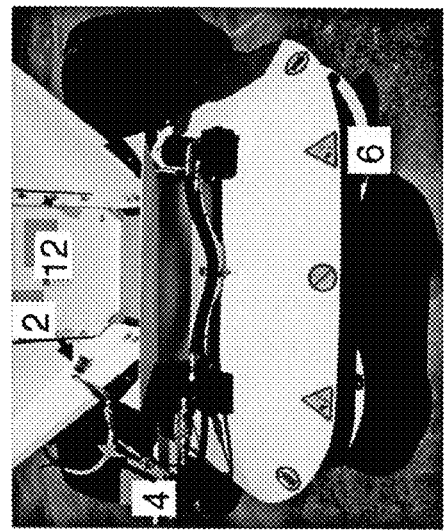
Figure 8E:
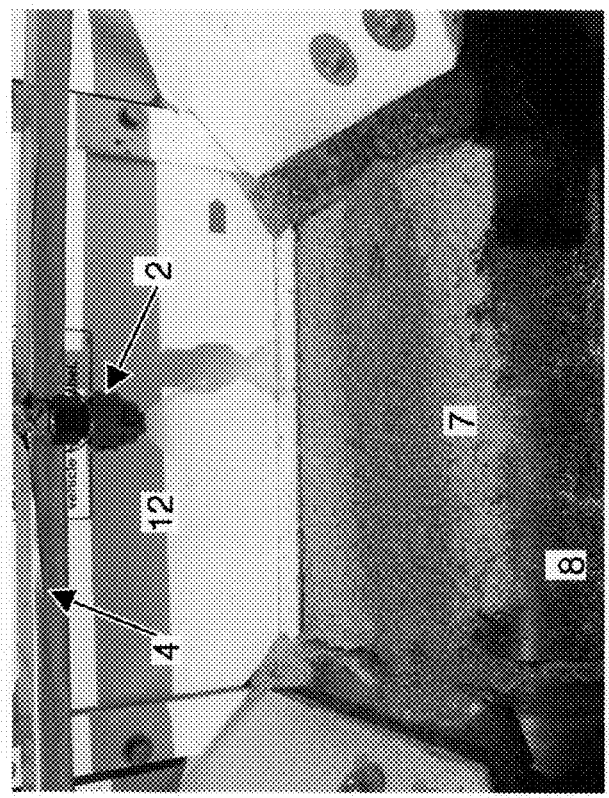
Figure 8D:
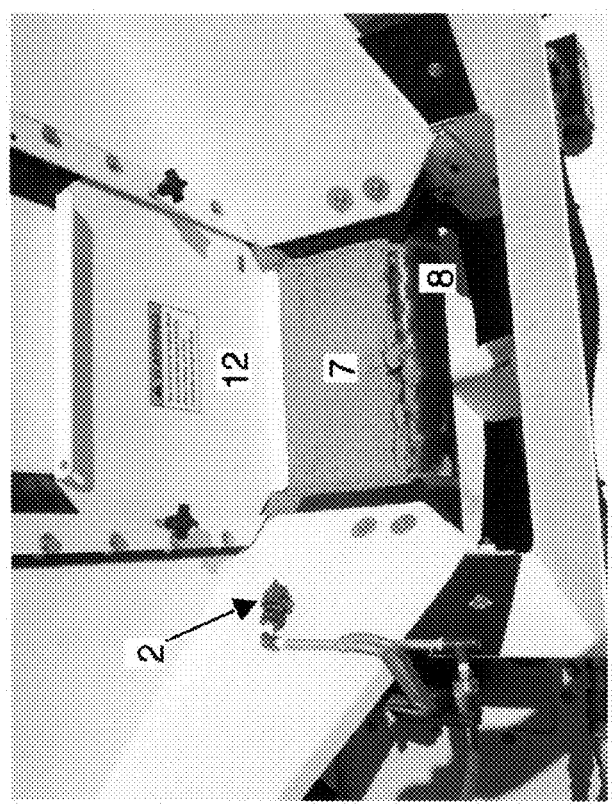

The inventors further contemplate the use of valves, compressors, and pumps as additional components of a sprayer unit. The inventors contemplate using valves compatible with the sprayer systems of the present inventions. Various types of valves are contemplated, including regulator valves, regulated manually or automatically. Other types of valves include shut off valves, for example an emergency shut off valve, ball valve et cetera.

The inventors contemplate using compressors compatible with the sprayer systems of the present inventions, such that the compressor provides stuffiest pressure for combination of tank size, valves, hose diameters, hose lengths, etc., for providing a desired flow rate through the attached nozzles, for example providing a specific p.s.i. (pounds per sq. inch) of liquid ejected from the nozzle. In a preferred embodiment, the inventors contemplate a $CO_2$ sprayer attached to the top dressing vehicle, for blending, dropping and spinner applications. An exemplary $CO_2$-powered sprayer, see, for example, at worldwide web.masspray.com, is provided for use in the present inventions. The inventors contemplate the use of a larger capacity sprayer unit, i.e. larger in volume, than used for the Examples described herein. Specifically, the inventors contemplate a sprayer system capacity capable of treating a top dressing, i.e. sand moving onto an exemplary path 40' swath at 7 MPH (miles per hour) axle speed. In another exemplar speed of application is broadcasting a 12'-20'-swath at a 3-5 MPH axle speed. In particular, the inventors contemplate the use of an electric pump. In another embodiment, the inventors contemplate the use of a hydraulic pump as part of a tank sprayer unit. The inventors further contemplate the use of a $CO_2$ compressor.

Regarding the Dakota 440 and a sprayer attachment, the inventors contemplate a blender option, in one embodiment for commercial availability, where a sprayer unit is installed/attached to the machine location in place of the granule bin 15, FIG. 10. This would provide a large area for the spray curtain to cover the conveyor belt, covered with topdressing material, before the top dressing drops onto the next conveyor, in addition to allowing greater operator access to the sprayer equipment. In other embodiments, where both granule blending and sprayed sand options are included in the same machine, the inventors contemplate design changes to house the spray tank, pump, etc., see, FIG. 10 for examples. Where multiple options are provided, the nozzles are contemplated to be attached in a location for applying a spray near the base of the elevator (after the sand has dropped onto the belt), using the elevator housing to support the nozzles, for example, see FIG. 10. Alternatively, the inventors contemplate attaching nozzles where the belt passes under the granule-blending unit for spraying the sand as it drops onto the belt. In other embodiments, the spray unit is attached at the rear of the Dakota 440 TurfTender for spraying the belt conveying means. In this embodiment, a nozzle would be attached where the spray coat sand being moved on top of the conveying means before the sand drops onto the spinners, see FIG. 8.

These examples are not meant to limit the type of sprayer unit, nor types of components, such as valves, compressors, pumps, nozzles, hoses, etc., nor location of sprayer unit or components. Any sprayer unit capable of applying the formulations of the presenting inventions when attached to a topdresser vehicle finds use in the present inventions.

2. Types of Nozzles.

Nozzles contemplated for use in the present inventions include but are not limited to commercially available nozzles. Any nozzle capable of providing a uniform application across a topdressing material, including mixtures of top dressing materials, sand, and the like, are contemplated for use.

In general, the nozzles would preferably be attached toward the rear of the top dressing machine (drop-type, and spinner-type). However other locations are contemplated depending upon the type of top dressing vehicle being used. The inventors contemplate attaching a nozzle(s) mounted above or at the side of a sand conveyor belt at the rear of a top dressing machine, just above, and in front of the spinners, as one example, the Dakota 440 TurfTender has an accessible, long, open sand belt area just before the sand falls/drops onto the spinners. However any location is contemplated where appropriate on other spinner-type topdressers and drop-type top dressing machines. Many brush-drop type topdressers have space in front of the sand bin for a sprayer unit and large areas of access to the conveyer belt where nozzles could be mounted behind the sand bin just in front of the brushes.

In a preferred embodiment for both types of top dressing vehicles, the attached nozzle is an even-pattern nozzle (also called band nozzles. Such that, in one embodiment, an exemplary nozzle is directly mounted directly above a conveying means, such as a belt, see, for example, FIGS. 4D and 5B. In these examples, the inventors used an even-pattern flat fan band spray nozzle with a capability of allowing a flow of 1 gallon/minute (for example, a Tee Jet 8010E, 1101E, and the like, TeeJet Technologies, Carol Stream, Ill.) for at least allowing a flow of 1.5 gallon/minute (for example, a TeeJet 8015E, TeeJet 11015E, and the like). These nozzles are contemplated to deliver a sufficient spray volume to for applying an exemplary range of 10-15-gallon/acre spray volume to sand as the sand is being distributed/applied to a 4000+ sq. ft. area of turf as a 20 ft. swath, while the vehicle is traveling at 2.3 MPH in a 1 minute duration.

In general, any nozzle that sprays a liquid in a preferable flat spray pattern is also contemplated for use. Nozzles contemplated for use in the present inventions are attached at an approximate 95-degree angle for spraying approximately 0.2 gallon/minute at 40 PSI. In a further embodiment, a TeeJet Flat Fan 9502E nozzle is contemplated for use.

Figure 12A:
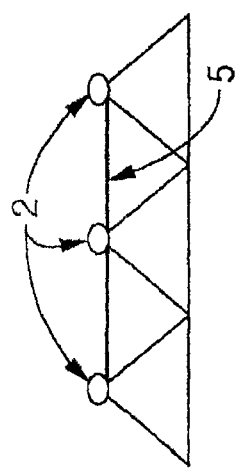
FIG. 12 shows an exemplary A) even spray nozzles 2 with a corresponding schematic of a spray curtain (white triangle) to show spray coverage from at least one nozzle and several nozzles attached to bar 5 and B) uneven spray nozzles 2 attached with bar 5 showing a schematic of an overlapping spray curtain (triangles).

As used herein, the "E" of the nozzle number refers to the capability of the nozzles to spray the same volume across the entire pattern (band), see, FIG. 12A. E nozzles are not meant to be overlapped. However other types contemplated for use include flood jet nozzles, cone jet nozzles, twin jet nozzles, full jet nozzles, etc. These other types of nozzles would allow changing spray volumes to accommodate various swath widths, ground speeds, etc. on the top dressing machines.

On the other hand, the inventors contemplate one nozzle type and size for attaching to top dressing vehicles for each of the applications, regardless of sand volume, travel speed, or swath width. The nozzle height above the sand belt would depend on the nozzle type finally selected. A 110 degree even band nozzle would likely be mounted 4"-6" above the sand belt, while an 80 or 95 degree even band nozzle would likely be mounted at 5"-7" above the sand belt. An off-center, directed spray nozzle would likely be mounted less than 9" above and a few inches to the right or left side of the sand belt. The sand belt itself is about 1' wide on the 440. The objective would be to apply an even band of spray to the entire width of the sand belt, whichever nozzle is selected. For using nozzles with the drop-type belt topdressers, a preferred embodiment is to attach more than one nozzle close as possible to the sand to minimize wind interference and drift. A single nozzle was not found to be applicable to the drop-type top dressers because even a 110 degree even spray pattern nozzle would have to be mounted too high (above the machine) in order to cover a 5-6 ft swath. In a preferred embodiment, the top dressing vehicles have attached even-pattern nozzles each spraying approx. an 18" band on the wide belt top dressers.

For using nozzles with the spinner-type topdressers, a preferred embodiment is to attach at least one nozzle, as described for the drop-type top dressing vehicles. In even further embodiments, the inventors contemplate a top dressing vehicle with a flow rate adjustor. In a further embodiment the flow rate adjuster would control multiple types of nozzles in order to adjust the spray volume to match the application in addition to other variables such as the type and amount of top dressing material to be covered, the type of application, the ground speed of the vehicle, the terrain, hill vs. flat, etc. In yet a further embodiment, the attached nozzle would be a rotating nozzle assembly of different nozzle types and volumes, multiple nozzles mounted in series that can be shut off individually, and the like.

Further, certain types of turf allow lower applications of sand per acre. For example, recent cultivars of turfgrass plants growing on golf course areas and other types of turf show similar benefits with lower amounts of applied sand than used in the example above. Lower volumes of sand would require lower amounts of spray amounts. Even further, in another embodiment, the inventors contemplate formulations with higher percentages of A.I.s (concentrated sprays). In these applications the inventors contemplate nozzles using nozzles that are capable of dispensing even sprays with lower volumes of fluid.

Contemplated vehicles of the present inventions have, in one embodiment, at least one nozzle mounted above and to the side of the conveying means, such as a belt 8 at the rear of the vehicle (for example, the Dakota 440 has 2 ideal locations side mounted nozzles, FIG. 8) for spraying a liquid onto the conveying means. Off-center nozzle tips apply an even band of spray below, and off to the side of the nozzle itself, for examples, a TeeJet OC12, TeeJet OC16, and the like, nozzle delivering 1.0-1.5 gallons/minute. The number and size of nozzles used depend on various factors such as travel speed, swath width, and volume of sand moving under the spray. One additional advantage of using a side-mounted nozzle is physical, such that the nozzle is less likely to interfere with access to the rear areas of the vehicles where access to the rear gate is desired. Further, the inventors found that when they mounted and used a side mounted nozzle on a Dakota 440 with the blender unit attachment and with an elevator unit it did not interfere with the movement of these units whereas a top mounted nozzle was less compatible with FIGS. 8, 9 and 11.

Additional flexibility is contemplated through the use of a rotating spray head, which might contain 3 or more individual nozzles of various capacities. The operator (or computer) would simply rotate the spray head to utilize the appropriate spray tip for the speed of travel, swath width, and sand volume he plans to apply. Similar rotating spray heads are already used on spray booms in agriculture. Currently, a sand volume of 0.025 cubic yard/1000 sq. ft., a spread width of 18', and a ground speed of 2.3 MPH are being used. On the other hand, research may eventually show that one nozzle type and size can fit all applications, regardless of sand volume, travel speed, or swath width, if spray volume and sand spray coverage turn out to not be important efficacy factors. The nozzle height above the sand belt would depend on the nozzle type finally selected. A 110-degree even band nozzle would likely be mounted 4"-6" above the sand belt, while an 80 or 95 degree even band nozzle would likely be mounted at 5"-7" above the sand belt. An off-center, directed spray nozzle would likely be mounted less than 9" above and a few inches to the right or left side of the sand belt. The sand belt itself is about 1' wide on the 440. The objective would be to apply an even band of spray to the entire width of the sand belt, whichever nozzle size or type is selected. It is appreciated that various other nozzle configurations operative herein will be apparent to one of skill in the art.

D. Additional Embodiments for Preventing Accidental and Potentially Harmful Over Application of Agriculturally Active Ingredients onto Turf Grass.

The inventors further contemplate providing and using flow rate adjusters for adjusting spray volumes, user manuals, and markers for controlling the coverage of top dressing materials provided by vehicles of the present inventions.

During the course of developing vehicles of the present inventions, the inventors discovered that the Dakota 440 Turf Tender does not automatically compensate application rates for speed of the vehicle, nor gate height, nor conveyor speeds, nor blending speed, nor instructions specific to for applying and delivering a top dressing material. However, the gate heights and belt (conveyor) speeds were manually adjustable for controlling blending operations and spreading operations. Currently the vehicle operator has to calibrate each material separately for both the blending and spreading operations. For example, at any given gate setting or belt speed, dryer sand comes out at a different speed than wetter sand, such as kiln dried sand compared to saturated sand. In addition, the inventors discovered that different types of sand blends of the present inventions had different rates of application despite using identical settings. For example, a 5% Daconil™/sand blend moved and was applied at a different rate than Prophesy™/sand blends, etc., see Examples. This variability in amounts between products was also found in the blending operation, in addition to the spreading operation. Therefore the opportunity for error potential without calibration tests provides at least a 2-fold difference in the amount of sand/blend applied between the different blends over less error in simply spraying sand as it left the topdresser. In other words, spraying top dressing materials, by hand or with vehicles of the present inventions, the spray rate is the principle variable, whereas dry formulations have compound variables including blending rates and the spreading rates.

Therefore the inventors further contemplate providing several types of calibration aids for use with compositions, vehicles, and methods of use of the present inventions. Calibration aids are contemplated in the form of written instructions and/or charts for providing suggested machine settings and operator instructions. This information should decrease the amount of time and increase the efficiency when using the compositions and vehicles of the present inventions, in particular with using different types of formulations and top dressing materials under a variety of terrain, turf grass plants, and disease applications. In particular, the inventors contemplate removing variability between specific types of applications, such as blending and applying blends of Prophesy™ (GR), Andersons 5% Daconil™ GR fungicide and the like. In particular, the inventors contemplate providing instructions, such as charts showing optimal settings, either specific or in ranges, for treating various types of top dressing materials of the present inventions for the use of the vehicles of the present inventions. Further, these instructions are contemplated to provide specific application instructions for types of turf grass plants and severity of disease out breaks or maintenance goals.

The types of calibration aids are contemplated to include but are not limited to a users manual, such as a user guide, operating instructions, and the like. Calibration aids also include a label for attaching to the vehicle, a manual for attaching to a vehicle, such as an embossed metal label, a waterproof manual, wherein example of an attachment include a chain, bolt, rivet, glue and the like. A calibration aid of the present invention comprises providing recommended settings for blending and delivering a composition comprising any one or more of A.I.s in combination with at least one of the types of topdressing materials of the present inventions. In another embodiment, the calibration aid comprises recommended conveyor speeds, gate opening settings, etc. for use with commercially available A.I. formations, top dressings, type of turf grass cultivar, type of turf, i.e. golf course green. In further embodiment, a chart comprising the setting recommended by the inventors for use with a top dressing vehicle is provided.

Thus in one embodiment, the inventors contemplate a calibration label, for example, a label attached to a Dakota 440 for providing optimal settings for using a Dakota 440 TurfTender as a top dressing vehicle of the present inventions. In another embodiment, the inventions contemplate providing a chart, for use with the Dakota 440 TurfTender or other commercially available blender, elevator, drop-type and spreader-type topdressing vehicle.

In another embodiment, the inventions further provide a "flow adjuster compensator unit" comprising a flow compensator valve and software which alters the sprayer valve setting and thus the spray rate based upon defined variables for preventing over application of an A.I. to an area of turf. Examples of defined variables include but are not limited to the speed of the topdressing vehicle, thus in general, a slow moving vehicle has a slow spray rate where the spray rate increases as the vehicle increases speed, however other variables are contemplated to calculate into adjusting the flow rate, such as sensing variables of axel speed, speed of the conveyor belt, height of the gate in the rear of the spinner machine which regulates the amount of released topdressing material, and type of topdressing material, sand, peat, soil and mixtures thereof, and type and concentration of active ingredient. In further embodiments, the inventors contemplate calibration aids as described herein.

Many types of markers, including foam markers, are used for preventing overlapping of materials used to cover surface areas in order to provide an even coverage of materials. In particular, markers are used in the agricultural industry for preventing harmful over doses of active materials. For example, U.S. Pat. No. 4,126,274, herein incorporated by reference, provides a device for making furrow markers in order to show where materials were spread over the ground. However marking a furrow in turf areas, such as golf courses, damages the sod and renders the surface unplayable.

In order to overcome such damage, in one embodiment, the inventors contemplate using 100% overlap spinners to prevent skips and harmful overlaps on spinner machines. In other embodiments, brush-drop-type spreaders are used to apply coated sand without skips or harmful overlaps because the swath edges are more sharply delineated than the tapered swath edge observed with spinner-type topdressers.

Further contemplated is marking the edge of the throw pattern from spinner-type machines and drop-type topdresser applied swaths of applied coated top dressing material. Thus the inventors contemplate adding an adjustable foam-marking boom to the top dressing vehicle in order to allow the operator to locate the edge of the throw pattern. Even further, a marker composition is contemplated for use with the foam boom. Even further, a marker composition is contemplated for adding to the spray formulation for monitoring both the amount of sprayed material onto the top dressing material and for monitoring the swath of distributed top dressing material on the turf. For example, U.S. Pat. No. 6,369,122, herein incorporated by reference, which discloses foam marker compositions for delineating treated from untreated areas. Other types of foam marking systems contemplated for use with vehicles of the represent inventions include Richway marking systems, such as a Richway Trac Master, see, at World Wide Web richway.com/turftracker.pdf, herein incorporated by reference.

In one embodiment, the inventors contemplate a single line of foam. For example, a single line of foam provided by a foam unit mounted on the tractor pulling the vehicle is contemplated for use with Dakota top dressers. In other embodiments, two or more lines of foam are contemplated. In preferred embodiments, the inventors contemplate attaching a foam unit directly to the top dressing vehicle in order to provide a single line Of foam centered with the spread swath. In other embodiments, the foam unit is provided with the injector mounted on a boom, see FIG. 7B. In a further embodiment, the boom length is adjustable (as in telescoping) for various swath widths (12'-20' and others). In this case, the operator would center the tractor directly over a foam line to achieve 100% overlap, whatever swath width they are using.

Boom-mounted ejector units may be necessary if the sand, when applied heavily, masks a swath-centered foam line. In another embodiment, the foam disappears in about 15 minutes, for example, DAWN detergent foam.

Thus any type of marker is contemplated for use that will reveal the presence of and prevent skips and over-laps of coated material, which result in either untreated or damaged turf. It is anticipated that skips and unintentional overlaps will be minimized through the use of 100% overlap spinners, which are available for some spinner-type topdressers, such as the Dakota models. Additionally, spray volume is contemplated as adjustable for correlating with ground speed to increase/reduce spray volumes to the sand to adjust for increased/decreased ground speeds, respectively. The top dressing vehicles of the present inventions are contemplated for use in applying and delivering virtually any materials that can be sprayed on golf course turfs.

In one embodiment, clear foam with rapidly degrading foam is contemplated. Colored foam might be useful in areas of turf, such as fairways, where the foam would fall into the canopy, or areas where swaths are wider, making a clear foam line harder to observe (for example, at world wide web richway.com/buyersguide.pdf). Thus in some embodiments, the markers used for monitoring applications of coated top dressing materials would be colored in such as way as to reduce golfer anxiety, for example, using rapidly biodegradable markers, foam, and using neutral colors such as brown, yellow, blue, green, and the like.

In summary, the present invention provides top dressing vehicles for combining the sand top dressing operation and the chemical application operation normally practiced on golf courses into one procedure by mounting a chemical spray tank pump; spray nozzles, etc., onto finishing brush drop-type topdressers, spinner-type topdressers, and blending top dressers. Further, the inventors' contemplate, and provide herein, a range of embodiments of top dressing vehicles intended for particular applications of formulations of the present inventions. Additionally, any disclosed compositions, such as exemplary compositions referenced herein, may find use in methods providing such compositions using top dressing vehicles of the present inventions for applying liquid fungicides and other A.I.s onto top dressing materials and blending top dressing materials with A.I.s at a point-of-application, such that as the materials are blended they are used, in other words the compositions are simultaneously coated and dropped or broadcast onto areas of turf grass. Even further, the inventors' contemplate, and provide herein, a range of embodiments of top dressing vehicles for use in methods of applying commercially available and formulations available in the future intended for application onto turfgrass plants.

EXPERIMENTAL

The following examples serve to illustrate certain embodiments and aspects of the present invention and are not to be construed as limiting the scope thereof.

In the experimental disclosures which follow, the following abbreviations apply: g (grams); L and l (liters); ml (milliliters); m (meters); min (minute); s and sec (second); sq (square), ft (foot, feet), square foot ($^2$); ha (hectare), ac (acre), lb (pound), gpa (gallons per acre), gph (gallons per hour), GR (granule), Liters per Hectare (L/ha), Liters per acre (L/ac), and LSD (Least Significant Difference Test).

Example I

Materials and Methods.

Figure 2:
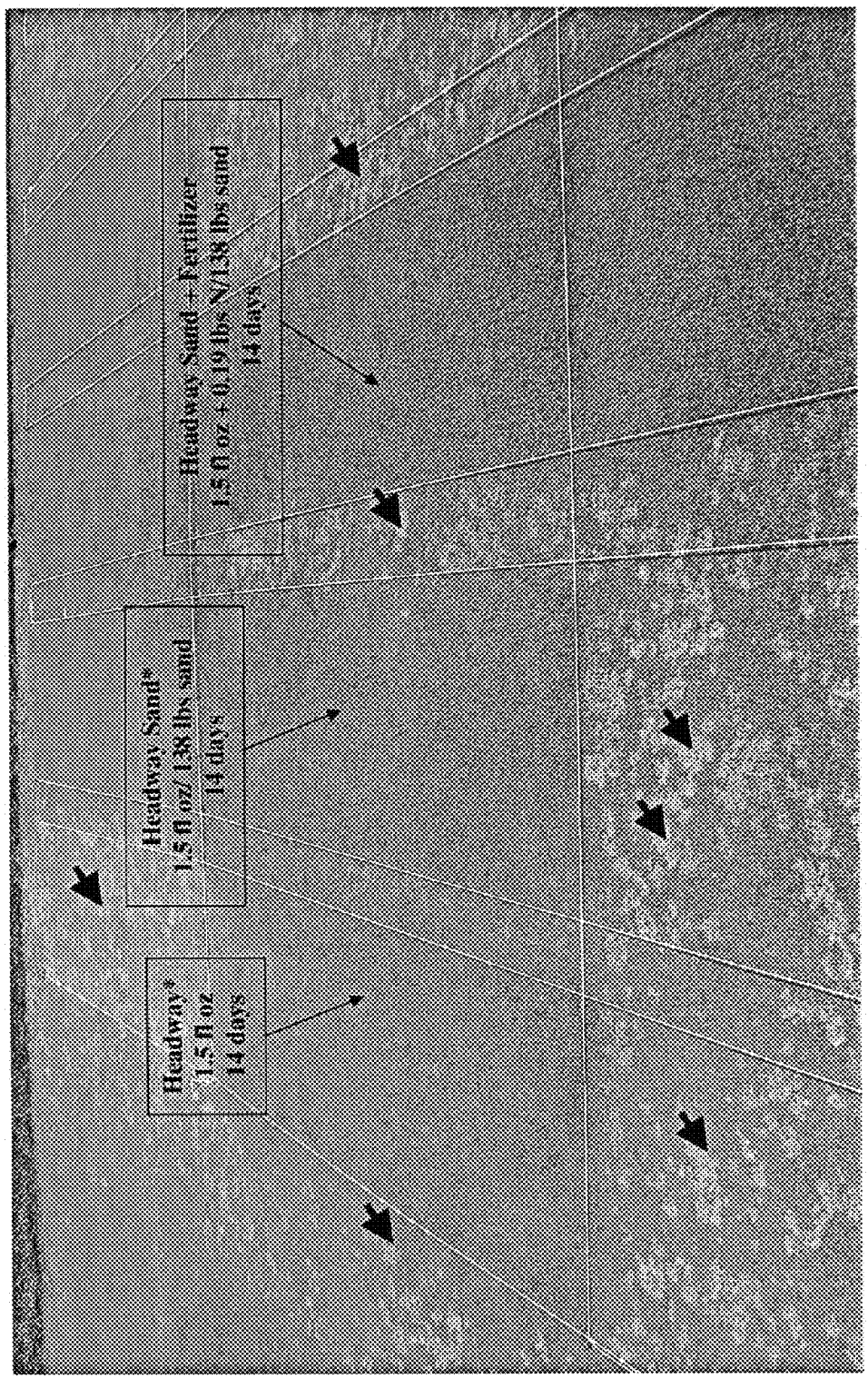
FIG. 2 is an exemplary photograph showing a Suppressive Sand Dollar Spot Study, 2007, demonstrating effectiveness of Headway fungicide treated sand on turfgrass disease. Conducted at the Hancock Turfgrass Research Center, Michigan State University (M.S.U.), East Lansing, Mich. (MI). Treatment rates indicated are per 1000 sq ft. *Treatments received greens grade Country Club fertilizer (18-3-12) at a rate of 0.19 lbs N/1000 sq ft every 14 days. Arrows point to areas of dead turf.
Figures 3A, 3B:
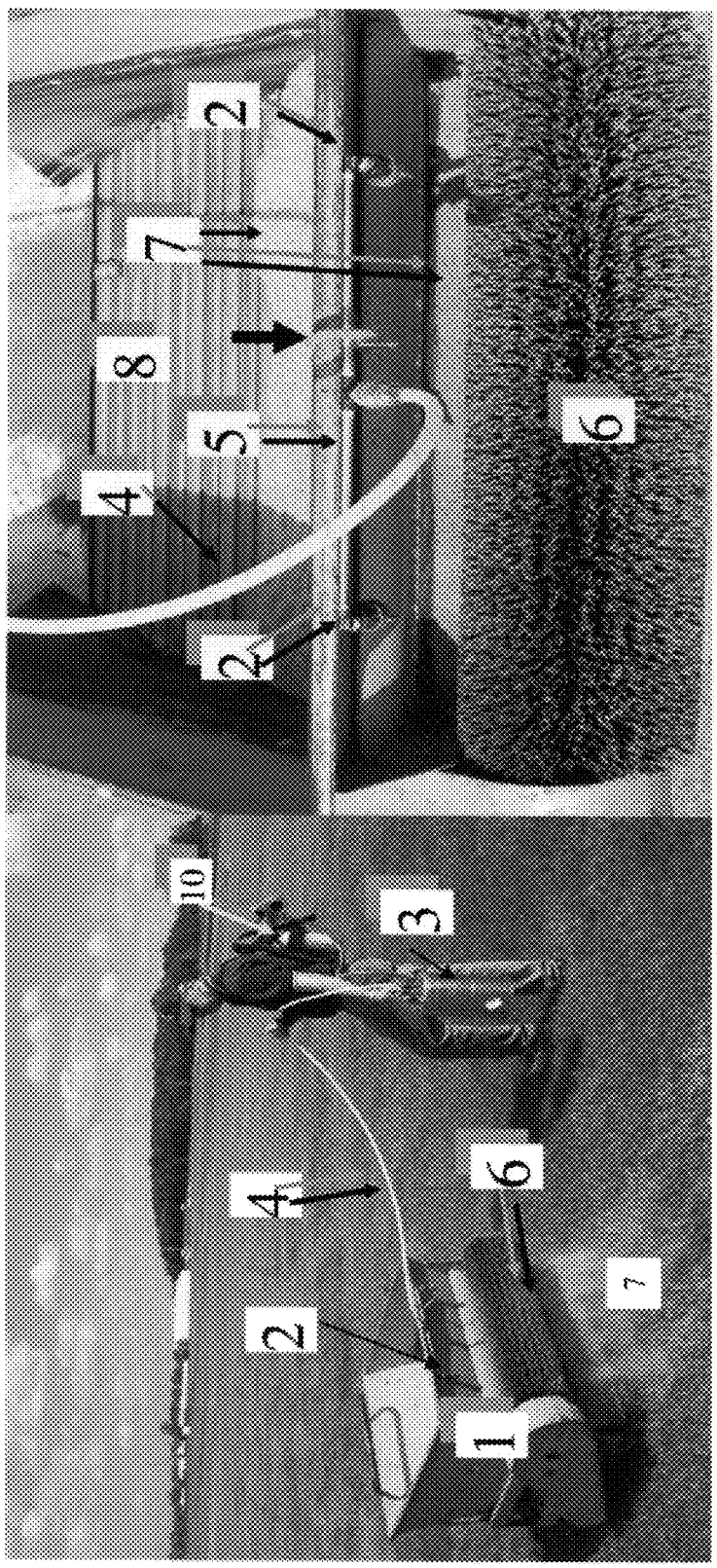
FIG. 3 shows an exemplary finishing brush drop-type topdressing vehicle 1, A) with an attached nozzle 2, and manually dispensing a spray of a liquid formulation, using a $CO_2$ compressor 10, from a tank 3, through a hose 4, onto a sand conveyor means, belt, 8 carrying sand to the finishing brush 6, for distributing a topdressing material 7 and B) showing two nozzles attached with a metal pipe 5, for dispensing liquid from hose 4, through nozzles 2, onto a sand conveyor belt 8 carrying sand 7 to the finishing brush 6.

The following is a description of exemplary materials and methods that were used in subsequent Examples II and III, with exemplary results shown in FIGS. 1 and 2, during the development of the present inventions.

Exemplary test compositions were provided and used as turfgrass treatments as shown in Tables below. Test treatments were applied to an established providence creeping bentgrass putting green (0.15 inch cutting height) on the Hancock Turfgrass Research Center on the Michigan State University campus in East Lansing, Mich. Treatments are applied to four replicate 2'×6' plots with 6" alleys using a $CO_2$-powered backpack sprayer (foliar applications) and a Scotts™ 22" drop spreader for delivering sand treatments and treatments comprising a granular formulation of A.I. hand blended with sand. Sand was supplied as local sand obtained in the Lansing, Mich. area of the United States.

Combined sand (topdressing) and chemical (A.I.) compositions for treatments were created by applying Scotts Miracle Gro™ (36-6-6) soluble fertilizer and/or commercial turfgrass fungicides in an aqueous solution, onto dry topdressing sand (sand meeting USGA specifications), and re-drying the treated sand prior to application/delivery. For these examples, the liquid was applied to the top dressing by soaking the sand in the aqueous solutions contained by a bucket.

Each treatment of a sand composition of the present inventions was then pre-weighed and applied to each plots individually, while the spray applications were applied at 50 GPA and allowed to dry on the grass plant foliage. The sand treatments were not brushed into the turf as would be customary, but irrigation was applied to wash the sand into the canopy, foliage and turfgrass plant, and activate the fertilizer or chemicals. The sand application rate of 138-lbs/1000 ft$^2$ approximates the highest application rate within the recommended range of 45-135 lbs/1000 ft$^2$ (Beard, J. B. 1982. Turf Management for Golf Courses p. 144, Burgess Publishing Co, Minneapolis; Beard, J. B. (and The United States Golf Association) 2002. Turf Management for Golf Courses, second Ed, Ann Arbor Press. p. 159 and Table 3.1, Ann Arbor Press, Chelsea, Mich., herein incorporated by reference). Treated plots that did not receive Miracle Gro™ fertilizer were fertilized with Lebanon Country Club™ (greens grade) fertilizer (18-3-12) at the same rate of actual nitrogen/1000 ft$^2$ that the Miracle Gro™ treated plots received.

Treatment application was initiated on Jul. 15, 2007, and on subsequent dates through Sep. 18, 2007, as indicated in the data tables that follow. In each experiment, the fungicides/fertilizer treatments were reapplied on a 14-day schedule. Natural infections of dollar spot within the study area were uniform ranging from 10-15% of the surface area when the July 15 treatments were initially applied.

Treatments initiated at later dates were placed on more heavily diseased plots because over time the disease intensity increased at least 60% in untreated and control plots over time of the duration of study.

Example II

This example demonstrates the effectiveness of compositions of the present inventions to suppress dollar spot fungus, in an exemplary "Suppressive dollar spot sand study." Field plots were treated with the compositions as described in Tables 3 and 4, with results demonstrated in FIGS. 1 and 2.

Sand top dressing compositions of the present inventions were prepared and used as treatments as described in the Example 1, while liquid formulations were applied by spraying on field plots in order to determine whether agricultural chemicals would continue to be effective while using sand as a carrier. Spraying rates were described in Example 1 at rates per 1000 s.q. feet.

The inventors found that formulations of the present inventions comprising sand coated with a liquid mixture of azoxystrobin and propiconazole in the form of Headway™ by Syngenta (Active Ingredients: Azoxystrobin: methyl (E)-2-{2-[6-(2-cyanophenoxy) pyrimidin-4-yloxy]phenyl}-3-methoxyacrylate as 5.73% and propiconazole: (CAS No. 60207-90-1) as 9.54%, in other words 0.868 lb A.I. propiconazble and 0.521 lb A.I. as azoxystrobin per gallon) in one embodiment as an exemplary fungicide in the strobilurin class of chemical compounds. Additional examples of compositions and methods of the present inventions were provided using a mixture of triadimefon and trifloxystrobins in a formulation of Tartan™ Bayer Environmental Science (Active Ingredients: triadimefon (CAS No. 141517-21 7) 4.17% and Trifloxystrobin (CAS No. 43121-43 3) 20.86%, equivalent to 2 pounds of triadimefon and 0.4 pounds of trifloxystrobin per gallon). In further embodiments, these fungicides were used with and without an All Purpose Miracle Gro™ fertilizer 24-8-16 (24-% nitrogen, 8% phosphorus, and 16% potassium by weight) (Scotts Miracle-Gro Company), provided dollar spot disease control comparable to the standard spray formulations of Headway™ and Tartan™ sprays alone on three successive rating dates. Exemplary data is shown in Tables 3, 4 and by arrows in FIGS. 1 and 2.

In terms of turfgrass quality, the combination of Headway™ with Miracle Gro™ fertilizer applied to sand gave significantly better turf quality on the three rating dates, compared to the Headway™ spray alone and Headway™ spray in combination with homogeneous methylene urea Country Club™ (18-3-12;18% nitrogen, 3% phosphorus, and 12% potassium) fertilizer (LebanonTurf). This improvement was consistent with the turf quality improvement often seen following sand topdressing applications. No phytotoxicity was observed during the study duration although turf greening/darkening was increasingly apparent with reapplication of Headway and Tartan treatments.

TABLE 3

Suppressive dollar spot sand study, 2007.
Rating Scale: Mean visual estimation of percent plot area infected with dollar spot disease.

| Trt # | Treatment (Trt) and Rate/1000 sq ft[a] | Application Timing | Aug. 4 Mean[b] | LSD[c] | Sep. 1 Mean | LSD | Sep. 22 Mean | LSD |
|---|---|---|---|---|---|---|---|---|
| 3 | Headway ™ and fertilizer-coated sand 1.5 fl oz and 0.19 lb nitrogen on 138 lb sand | 14 | 0.0 | a | 0.25 | a | 0.1 | a |
| 1 | Headway ™ spray 1.5 fl oz | 14 | 0.0 | a | 0.313 | a | 0.2 | a |
| 12 | Tartan ™ spray 1 fl oz | 14 | 0.5 | a | 0.25 | a | 0.4 | a |
| 2 | Headway ™ coated sand 1.5 fl oz on 138 lb sand | 14 | 0.2 | a | 0.688 | a | 0.4 | a |
| 15 | Tartan ™ coated sand 1 fl oz on 138 lb | 14 | 0.0 | a | 1.5 | a | 0.8 | a |
| 16 | Tartan ™ and fertilizer-coated sand 1 fl oz and 0.19 lb nitrogen on 138 lb sand | 14 | 0.1 | a | 1.5 | a | 0.8 | a |
| 17 | Headway ™ spray treatment alternated with a 138 lb sand application | 7 | na | | 0.875 | a | 0.9 | a |
| 18 | Tartan ™ spray treatment alternated with a 138 lb sand | 7 | na | | 1.875 | a | 1.9 | a |
| 6 | Fertilizer-coated sand 0.19 lb nitrogen on 138 lb sand | 14 | 32.5 | b | 45 | b | 38.8 | b |
| 13 | Untreated Control | 14 | 41.3 | c | 46.25 | b | 43.8 | b |
| 5 | Plain sand applied at 138 lb | 14 | 40.0 | c | 50 | c | 45.0 | b |

[a]Each treatment was applied on the same day, 7/15, 7/29, 8/11, 8/26, and 9/8, for 5 total applications.
[b]Average of 4 replicate plots.
[c]Means followed by the same letter are not significantly different from each other (LSD, 5%).

TABLE 4

Suppressive dollar spot sand study, 2007, for rating: Turfgrass quality following each application. Rating scale: 1-10, where 1 = poor, 7 = acceptable, and 10 = excellent.

| Trt # | Treatment and Rate/ 1000 sq ft[a] | Application Timing | Aug. 4 Mean[b] | LSD[c] | Sep. 1 Mean | LSD | Sep. 24 Mean | LSD |
|---|---|---|---|---|---|---|---|---|
| 3 | Headway ™ and fertilizer-coated sand 1.5 fl oz and 0.19 lb nitrogen on 138 lb sand | 14 | 8.6 | a | 11.3 | a | 9.0 | a |

TABLE 4-continued

Suppressive dollar spot sand study, 2007, for rating: Turfgrass quality
following each application. Rating scale: 1-10, where 1 = poor, 7 = acceptable, and
10 = excellent.

| Trt # | Treatment and Rate/ 1000 sq ft[a] | Application Timing | Aug. 4 Mean[b] | LSD[c] | Sep. 1 Mean | LSD | Sep. 24 Mean | LSD |
|---|---|---|---|---|---|---|---|---|
| 2 | Headway ™ coated sand 1.5 fl oz on 138 lb sand | 14 | 7.8 | bc | 10.9 | ab | 8.5 | b |
| 1 | Headway ™ spray 1.5 fl oz | 14 | 7.3 | c | 10.6 | bc | 8.4 | bc |
| 15 | Tartan ™ coated sand 1 fl oz on 138 lb | 14 | 7.5 | bc | 10.8 | d | 8.1 | cd |
| 12 | Tartan ™ spray 1 fl oz | 14 | 7.5 | bc | 10.8 | cd | 8.0 | d |
| 17 | Headway ™ spray treatment alternated with a 138 lb sand application | 7 | na | | 7.7 | e | 8.0 | d |
| 18 | Tartan ™ spray treatment alternated with a 138 lb sand | 7 | na | | 7.7 | e | 8.0 | d |
| 16 | Tartan ™ and fertilizer-coated sand 1 fl oz and 0.19 lb nitrogen on 138 lb sand | 14 | 8.1 | ab | 11.1 | cd | 7.9 | d |
| 6 | Fertilizer-coated sand 0.19 lb nitrogen on 138 lb sand | 14 | 5 | d | 9.5 | f | 2.3 | e |
| 5 | Plain sand applied at 138 lb | 14 | 3.5 | e | 8.8 | g | 2.0 | e |
| 13 | Untreated Control | 14 | 3.3 | e | 8.6 | fg | 2.0 | e |

[a]Each treatment was applied on the same day, 7/15, 7/29, 8/11, 8/26, and 9/8, for 5 total applications.
[b]Average of 4 replicate plots; na = not available.
[c]Means followed by the same letter are not significantly different from each other (LSD, 5%).

Example III

This example demonstrates the effectiveness of compositions of the present inventions to suppress dollar spot fungus, in an exemplary "curative study." The results of curative treatments shown in exemplary Tables 5-6 include treatments added to the study later in the growing season. The treated plots were in various stages of recovery from severe dollar spot infections (ranging from 50-60%) so conclusions in these later studies were not provided for treatment efficacy on a curative basis.

The data indicated that turfgrass recovery using an A.I. comprising fungicides including chlorothalonil in a formulation comprising Daconil Ultrex™ (Active Ingredient: Chlorothalonil (tetrachloroisophthalonitrile) 82.5% as Water Dispersible Granules, Syngenta) and Chipco 26GT™ (Active Ingredient: Iprodione (3-(3,5-dichlorophenyl)-N-(1-methylethyl)-2,4-dioxo-1-imidazolidinecarboxamide)) 23.3% (contains 2 pounds of active ingredient iprodione per gallon as Sextant™ now called OHP® Chipco® 26GT-O, OHP, Inc. P.O. Box 230, Mainland, Pa., 19451)) may be slower when these fungicides are place on sand compared to slightly better activity towards dollar spot when applied as foliar sprays. The delayed or reduced efficacy was especially apparent in contrast to highly successful control of dollar spot infections using formulations of sand comprising propiconazole as a Banner Maxx™ formulation. Banner Maxx™ formulations were equally successful with and without adding Miracle Gro™ fertilizer. A formulation of the present inventions was also provided as a Flowable Fungicide as an exemplary Daconil Weather Stik™ Fungicide (Active Ingredient:Chlorothalonil (tetrachloroisophthalonitrile) of 54.0% in other words, 6.0 pounds chlorothalonil per gallon (720 grams per liter) Syngenta Crop Protection, Inc. Greensboro, N. C. 27409).

In another embodiment of a granular formulation, the A.I. is Prophesy™. In another embodiment of a granular formulation, the A.I. is contained within a formulation of AND6259 (Prophesy GR plus fertilizer). Both treatment formulations provided rapid turf recovery from heavy dollar spot infections, with the treated areas recovering by approximately 50% when observed four days after initial treatment applications.

These treatments were included to investigate the efficacy of commercial fungicide and experimental fungicide granular products when they are applied to or blended with top dressings and distributed by hand. Thus the inventors contemplated that treated sand and a blend of granular fungicide and fertilizer products with top dressing sand is a viable option for disease control and turfgrass quality improvement.

TABLE 5

Curative suppressive dollar spot sand study, 2007.
Rating scale: Mean visual estimation of percent plot area infected
with dollar spot disease. Rating date: Sep. 22, 2007.

| Trt # | Treatment and Rate/1000 sq ft | Application Timing | Mean[a] | LSD[b] |
|---|---|---|---|---|
| 22 | Chipco 26GT ™ 4 fl oz[c] | 14 | 20.5 | a |
| 30 | AND 6259 ™ 10 lb + Prophesy ™ (GR) 5 lb + Sand 138 lb Dry Blend[f] | 14 | 22.5 | ab |

TABLE 5-continued

Curative suppressive dollar spot sand study, 2007.
Rating scale: Mean visual estimation of percent plot area infected
with dollar spot disease. Rating date: Sep. 22, 2007.

| Trt # | Treatment and Rate/1000 sq ft | Application Timing | Mean[a] | LSD[b] |
|---|---|---|---|---|
| 19 | Daconil™ Weather Stik 5.5 fl oz[c] | 14 | 23.8 | a-c |
| 29 | AND 6259™ 5 lb + Prophesy (GR) 2.5 lb + Sand 138 lb Dry Blend[f] | 14 | 27.5 | a-d |
| 27 | Prophesy™ (GR) 2.5 lb + Fertilizer Sand 0.19 lb N/138 lb Dry Blend[f] | 14 | 30.0 | a-d |
| 28 | Prophesy™ (GR) 5 lb + Fertilizer Sand 0.19 lb N/138 lb Dry Blend[f] | 14 | 30.0 | a-d |
| 23 | Banner MaxxTM™ 1 fl oz[d] | 14 | 33.0 | b-d |
| 20 | Daconil™ Weather Stik Sand 5.5 fl oz/138 lb[c] | 14 | 33.8 | b-d |
| 21 | Chipco 26GT™ Sand 4 fl oz/138 lb[c] | 14 | 35.0 | cd |
| 26 | Banner MaxxTM™ Sand (ETOH[h]) 1 fl oz/138 lb[e] | 14 | 36.3 | de |
| 25 | Banner MaxxTM™ Sand w/Fert 1 fl oz + 0.19 lb N/138 lb[d] | 14 | 47.5 | ef |
| 24 | Banner MaxxTM™ Sand 1 fl oz/138 lb[d] | 14 | 51.3 | f |
| 5 | Sand 138 lb[g] | 14 | 55.0 | f |
| 13 | Untreated Control | 14 | 55.0 | f |

[a]Average of 4 replicate plots.
[b]Means followed by the same letter are not significantly different from each other (LSD, 5%).
[c]Treatments applied 9/1 and 9/15.
[d]Treatments applied 9/8 and 9/22.
[e]Treatments applied once on 9/12.
[f]Treatments applied once on 9/18.
[g]Treatment applied 5 times, each on 7/15, 7/29, 8/11, 8/26 and 9/8.
[h]Banner MaxxTM applied to sand in an ethanol (EtOH) carrier rather than water.

TABLE 6

Curative suppressive dollar spot sand study, 2007.
Turfgrass quality using a rating scale: 1-10, where 1 = poor, 7 = acceptable,
and 10 = excellent. Rating date: Sep. 24, 2007.

| Trt # | Treatment (Trt) and Rate/1000 sq ft | Application Timing | Mean[a] | LSD[b] |
|---|---|---|---|---|
| 22 | Chipco 26GT™ 4 fl oz[c] | 14 | 5.5 | a |
| 30 | AND 6259™ 10 lb + Prophesy™ (GR) 5 lb + Sand 138 lb Dry Blend[f] | 14 | 5.5 | a |
| 19 | Daconil™ Weather Stik 5.5 fl oz[c] | 14 | 5.0 | a |
| 27 | Prophesy™ (GR) 2.5 lb + Fertilizer Sand 0.19 lb N/138 lb Dry Blend[f] | 14 | 4.8 | a |
| 29 | AND 6259™ 5 lb + Prophesy™ (GR) 2.5 lb + Sand 138 lb Dry Blend[f] | 14 | 4.8 | a |
| 20 | Daconil™ Weather Stik Sand 5.5 fl oz/138 lb[c] | 14 | 4.3 | ab |
| 21 | Chipco 26GT™ Sand 4 fl oz/138 lb[c] | 14 | 4.3 | ab |
| 23 | Banner MaxxTM 1 fl oz[d] | 14 | 4.3 | ab |
| 28 | Prophesy™ (GR) 5 lb + Fertilizer Sand 0.19 lb N/138 lb Dry Blend[f] | 14 | 4.3 | ab |
| 26 | Banner Maxx™ Sand (ETOH[h]) 1 fl oz/138 lb[e] | 14 | 3.3 | bc |
| 25 | Banner Maxx™ Sand w/Fertilizer 1 fl oz + 0.19 lb N/138 lb[d] | 14 | 3.0 | bc |
| 24 | Banner Maxx™ Sand 1 fl oz/138 lb[d] | 14 | 2.5 | c |
| 5 | Sand 138 lb[g] | 14 | 2.0 | c |
| 13 | Untreated Control | 14 | 2.0 | c |

[a]Average of 4 replicate plots.
[b]Means followed by the same letter are not significantly different from each other (LSD, 5%).
[c]Treatments applied 9/1 and 9/15.
[d]Treatments applied 9/8 and 9/22.
[e]Treatments applied one time on 9/12.
[f]Treatments applied one time on 9/18.
[g]Treatment applied 5 times, each on 7/15, 7/29, 8/11, 8/26 and 9/8.
[h]Banner MaxxTM applied to sand in an ethanol (EtOH) solvent rather than water.

Example IV

This example shows exemplary drop-type topdressing vehicle of the present inventions. See, exemplary topdressing vehicles in FIGS. 3-6.

In one embodiment, a sprayer was attached to a drop-type topdressing vehicle of the present inventions and then was used in field applications for applying/delivering fungicide-sprayed sand to an area of test turfgrass. In one embodiment, a trailer type drop-type topdressing vehicle was provided comprising a $CO_2$ backpack sprayer with two TeeJet™ 8002E even band nozzles attached to a topdressing vehicle. This exemplary attached sprayer was used for a fungicide to moist sand moving along the belt conveyor prior to reaching the brush and being distributed/delivered onto the turf. See, FIG. 3.

In another embodiment, a self propelled drop-type topdressing vehicle (providing a 3 foot wide swath of applied sand) of the present inventions was provided comprising a $CO_2$ backpack sprayer with two TeeJet™ 8002E even band nozzles attached to an exemplary topdressing vehicle, i.e. a Meter-R-Matic™ Top Dresser, Turfco™. See, FIG. 4. This exemplary attached sprayer was used for applying a fungicide to sand moving along the belt conveyor prior to reaching the brush and being distributed onto the turf. This exemplary topdressing vehicle was used for delivering moist sand compositions in the Examples.

In another embodiment, a trailer drop-type topdressing vehicle of the present inventions was provided showing an exemplary attached sprayer unit comprising a tank, hose, nozzles and schematic of compressor unit attached to an exemplary 5 foot wide (sand swath width) Tycrop™ Quick-Pass™ topdresser vehicle/machine. Further provided was exemplary foam marking system for attaching to a topdressing vehicle of the present inventions, FIG. 6B.

See, FIGS. 5 and 6, demonstrating a 5' (providing a swath of applied topdressing material 5 feet in width) drop-type topdresser retrofitted with a small spray unit to apply chemicals to the sand belt just before the sand reaches the finishing brush for spreading the sand formulation of the present inventions onto the turf.

Example V

This example demonstrates the curative capability of delivering a moist composition of the present inventions at a point-of-application using a drop-type topdressing vehicle of the present invention. Further, these results show superior results of delivering a moist top dressing composition consisting of sand and a granular/dry form of a fungicide, i.e. comprising propiconazole, as an Andersons Prophesy™ GR (propiconazole) formulation over delivering a blended formulation consisting of sand and Andersons 5% Daconil™ GR fungicide. See, FIG. 13, arrows point to brown areas of fungal infected turf.

The inventors tested a moist sand formulation of the present inventions on an area of turf as part of the Hancock Turfgrass Research Center on the Michigan State University campus in East Lansing, Mich. A vehicle of the present invention was provided as in FIG. 4, as described above, for distributing this moist formulation of the present inventions.

A moist formulation was provided by placing a topdressing sand material in the main hopper of a Meter-R-Matic™ Top Dresser, Turfco™, and placing a fungicidal spray mixture in the tank for spraying the fungicide as a coating onto the sand just prior to application onto an area of turf at the Hancock Turfgrass Research Center on the Michigan State University campus in East Lansing, Mich. Rating Scale was provided as a percent recovery determined 11 days after the first application.

The sand moisture level for earlier experiments ranged between 1%-8% water content by weight (based on air drying). Sand used during experiments later in the summer (Mete-R-Matic Study) had approximately 1%-2 percent water content. At saturation, the topdressing sand used for these experiments was approximately 16.5% water by weight. In general, water weight at saturation is a variable dependent upon the particular starting composition of sand. Sand processing practices and storage conditions prior to use as a topdressing material is a factor that determines the moisture level of any topdressing sand.

TABLE 7

Meter-R-Matic ™ sprayed sand curative dollar spot study, 2008.
Rating Date: Sep. 22, 2008. Rating Scale: Percent turfgrass recovery from dollar spot disease levels at study initiation.

| Trt # | Treatment (Trt) and rate/1000 sq ft | Mean[a] | LSD[b] |
|---|---|---|---|
| 7 | Chipco 26GT ™ topdresser sprayed sand 4 fl oz on 67.5 lbs sand | 84.2 | a |
| 6 | Chipco 26GT ™ spray 4 fl oz | 69.0 | ab |
| 1 | Banner Maxx ™ spray 1 fl oz | 68.0 | ab |
| 2 | Banner Maxx ™ topdresser sprayed sand 1 fl oz on 67.5 lbs sand | 50.1 | a-c |
| 4 | Andersons Prophesy ™ GR 2.5 lbs | 41.0 | b-d |
| 5 | Andersons Prophesy ™ GR 2.5 lbs blended w/ sand 67.5 lbs sand | 31.3 | cd |
| 8 | Untreated control (no sand) | 25.0 | cd |
| 3 | Topdresser sand only 67.5 lbs sand | 12.5 | d |

[a]Mean of four replicate plots.
[b]Means followed by the same letter do not differ significantly (LSD, p = 0.05).

Example VI

This example shows several embodiments of sprayer units attached to spinner-type topdressing vehicles and blending-type topdressing vehicles of the present inventions. Some embodiments are demonstrated as schematics while other embodiments are provided showing actual components. These types of topdressing vehicles are contemplated for use in spraying a liquid fungicide or any other liquid agriculturally active ingredient onto a topdressing material, such as sand, peat, soil and mixtures thereof.

Figure 7A:
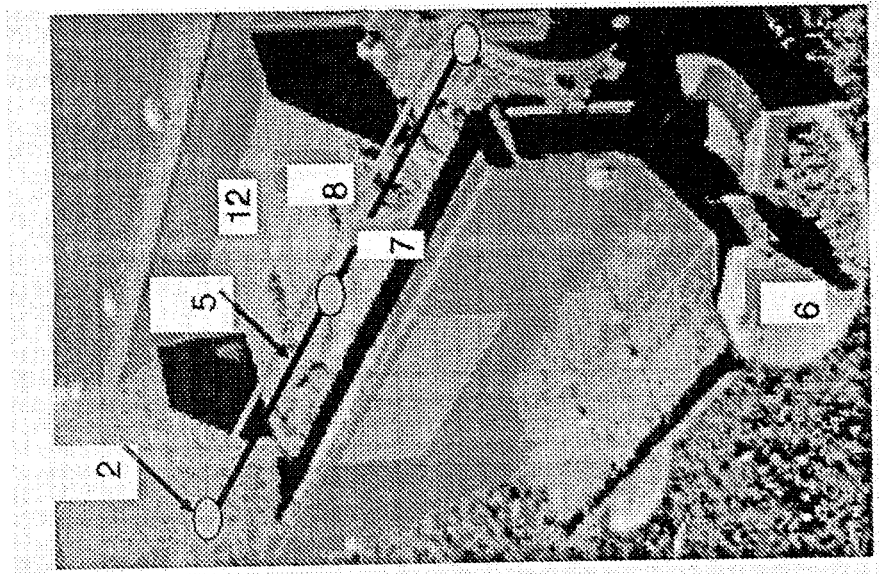
FIG. 7 shows an exemplary spinner topdressing vehicle 1 for use in the present inventions, A) shows a trailer-type spinner-type topdressing vehicle 1, showing an exemplary schematic for the placement and attachment of tank 3, compressor 10, B) shows one embodiment of exemplary nozzles 2, pipe 5, and a spray pattern schematic as white triangles showing where spray was applied to a topdressing material 7 distributed off the spinner unit 6 and an exemplary attachment foam marking system tank 3, compressor 10, hoses 4 leading to outlet tube 13 attached with bar/boom 5, C) shows another embodiment for the location of the nozzles 2 and pipe attachment 5 where the topdressing material, amount controlled by rear gate 12 is sprayed while on the conveying means prior to entering the spinner device 6.
Figure 7B:
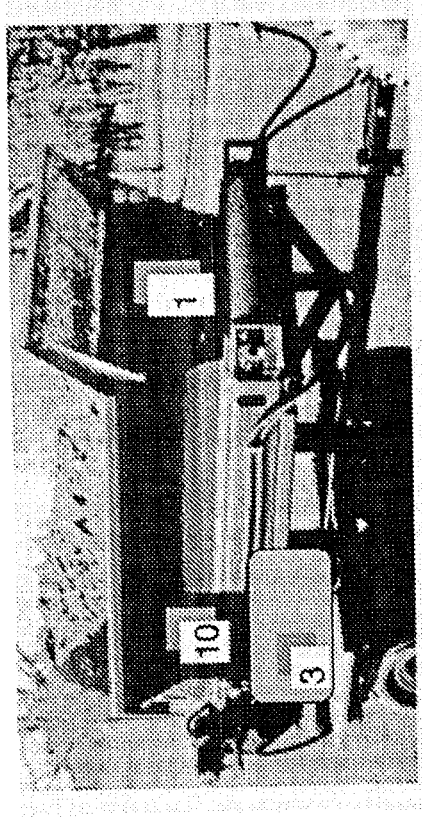
Figure 7C:
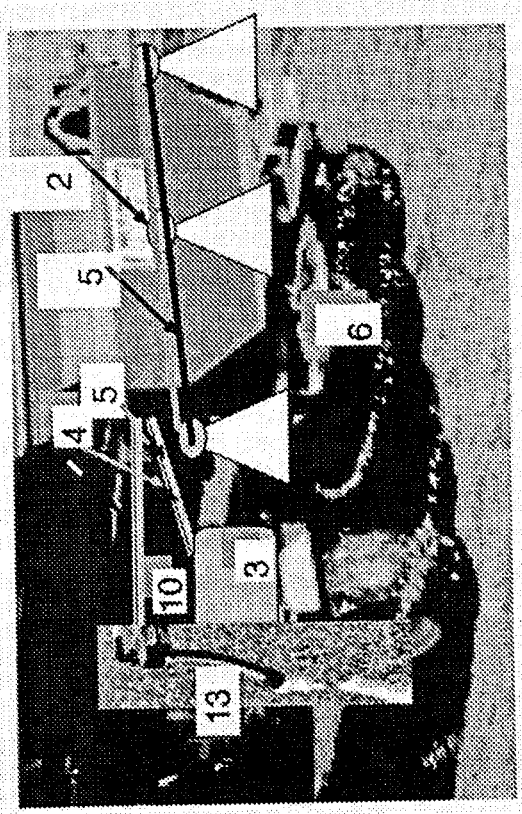
Figure 8C:
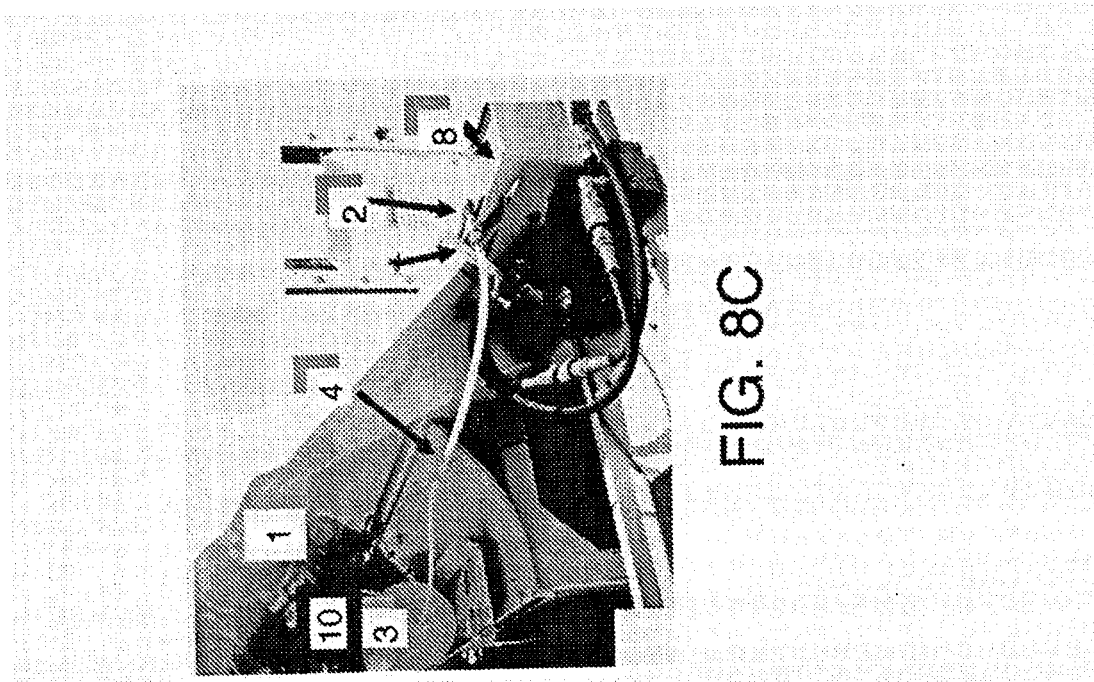
Figure 8A:
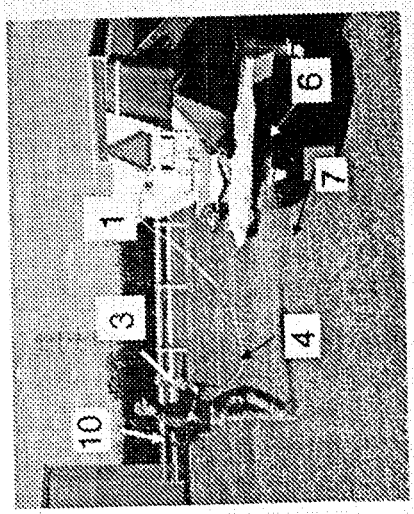
Figure 8B:
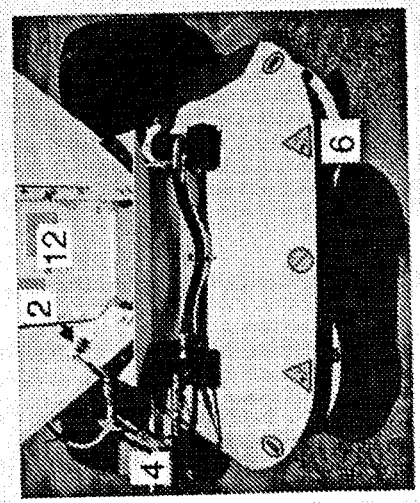
Figure 8E:
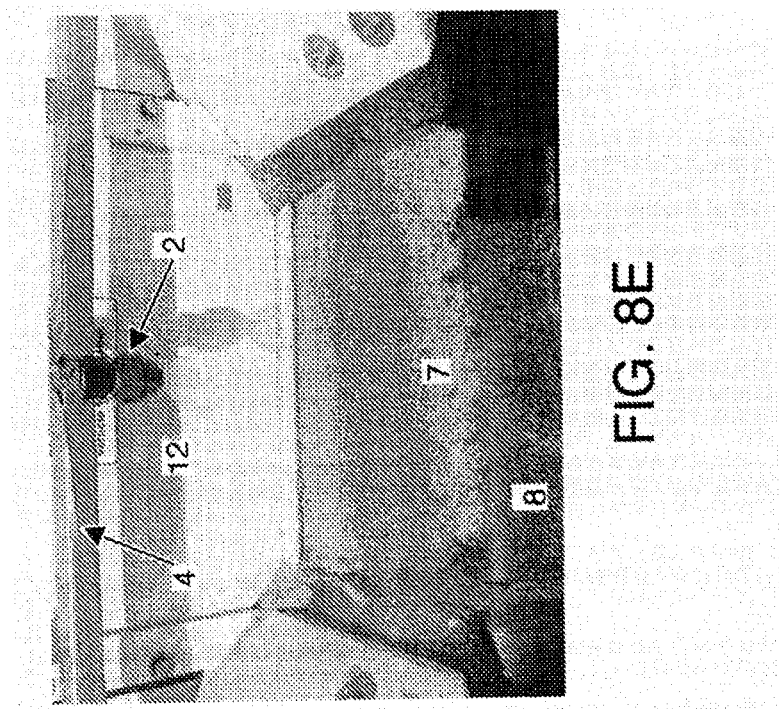
Figure 8D:
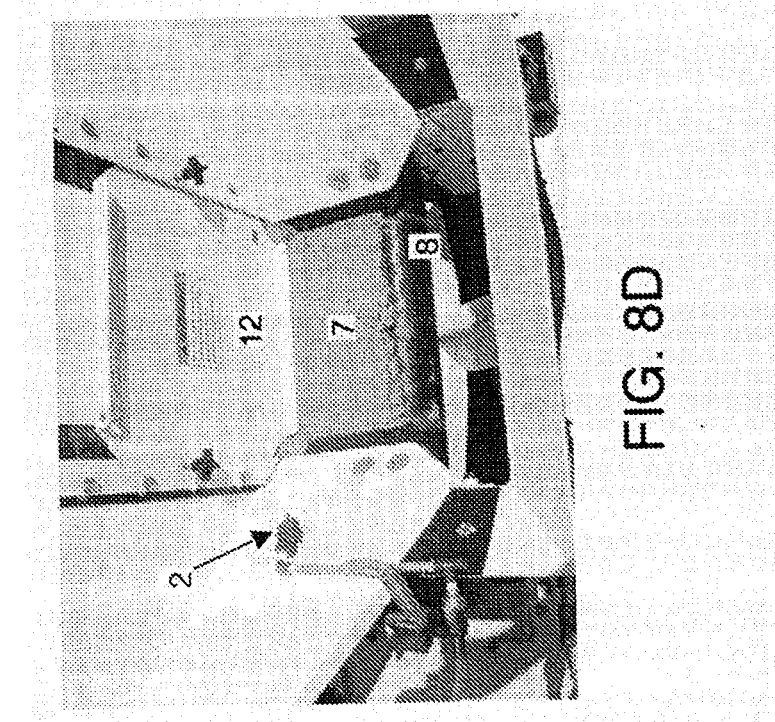

In one embodiment, a schematic showing the placement of a sprayer unit attached to a topdressing vehicle of the present invention is provided, see, FIG. 7A. In another embodiment, a schematic showing a contemplated placement of nozzles for spraying a liquid over sand during broadcast and a schematic of a spray curtain and attached foam marking system is provided, see, FIG. 7B. In another embodiment, a schematic showing a contemplated placement of nozzles for spraying a liquid over sand prior to entering the spinner device is provided, FIG. 7C. In particular, the schematic provides nozzles attached above the topdressing material providing a spray curtain directly above the topdressing material.

Further, this example provides a spinner-type topdressing vehicle of the present inventions used for delivering a moist sand formulation of the present inventions. This exemplary spinner-type topdressing vehicle, as shown in FIG. 8, comprises a sprayer unit attached to a Dakota 440 spinner topdressing vehicle 1 for coating a topdressing material at a point-of-application, where the nozzle is attached at the rear of the topdressing vehicle. In one embodiment, provided in FIG. 8, the nozzle is an off-center spray nozzle and attached to the vehicle at one side of the conveying means at the rear of the vehicle. In another embodiment, one off-center nozzle on each side is contemplated for attachment. In another embodiment, more than one nozzle per side of conveying means for spraying a liquid onto the conveying means is contemplated for attachment. The placement and number of the nozzles is for providing adequate coverage and even distribution of liquid onto the topdressing material being conveyed by the conveying means.

Figure 9A:
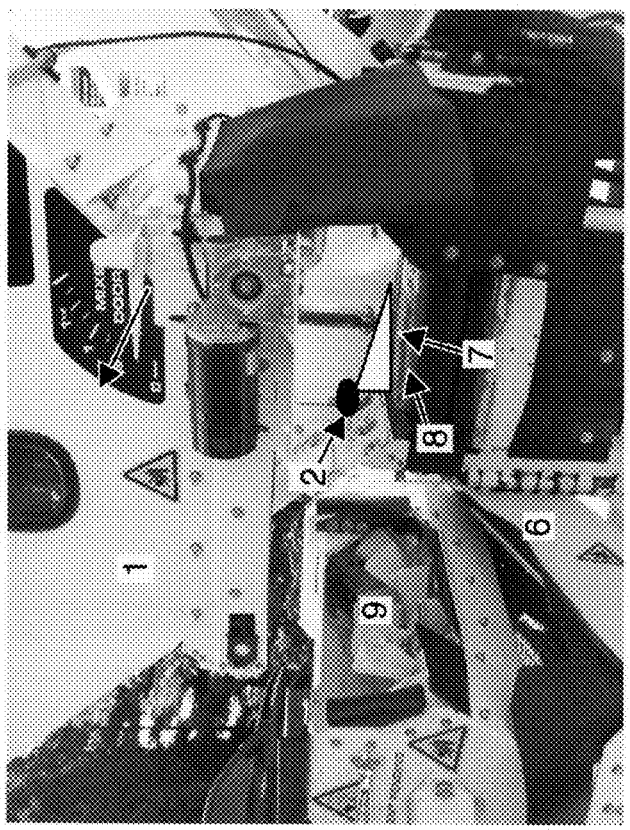
FIG. 9 shows an exemplary topdressing vehicle 1 for use in the present inventions where A) shows the blender 9 and elevator unit 6 with conveying means 8 in position for use, B) shows the blender 9 and elevator unit 6 with conveying means 8, and a schematic showing an offset nozzle 2 spraying and white spray curtain onto sand 7 being moved by conveyor 6 onto the ground because the blender unit 9 was out of position for use.
Figure 9B:
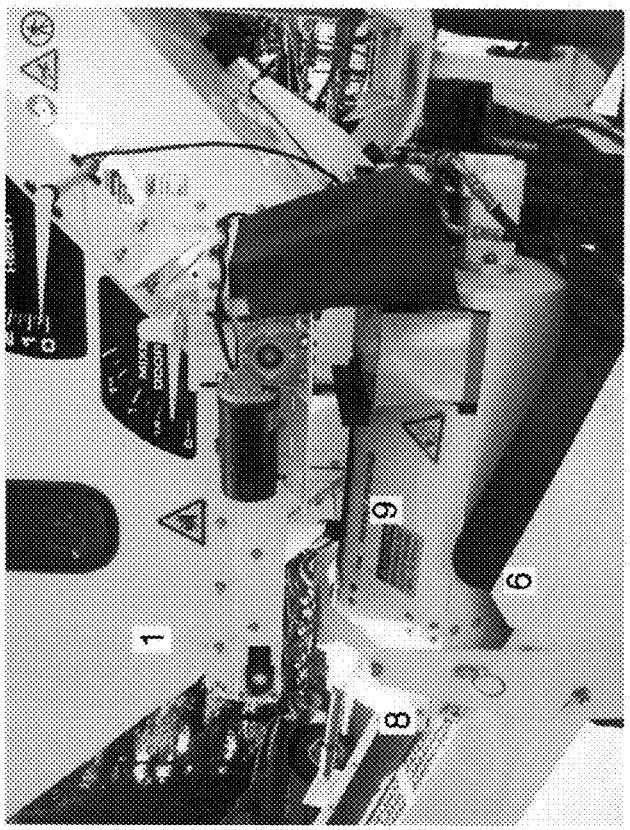
Figure 10B:
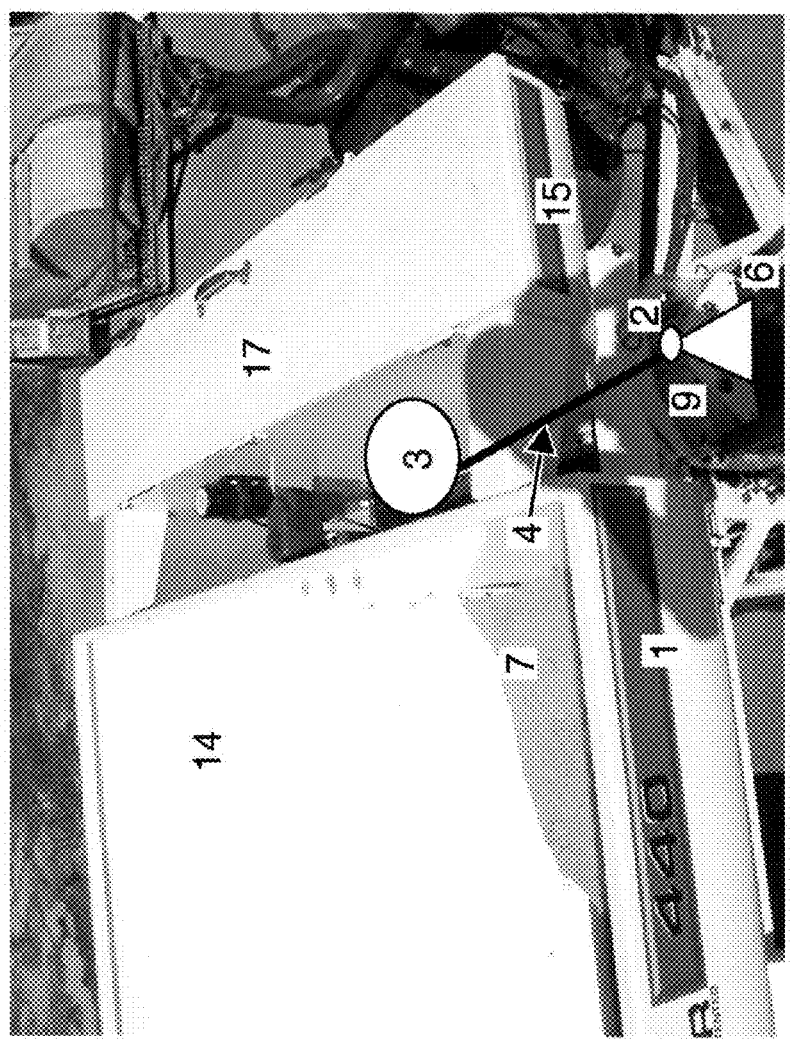
FIG. 10 shows an exemplary blending-type topdressing vehicle 1 with a primary hopper 14, a secondary hopper 15, a cover 17 for hopper 15, an attached blending unit 9, and elevator unit comprising a conveying means 8 for use in the present inventions, A) shows a contemplated hose 4, nozzle 2, and spray pattern as a schematic white triangle for treating a blended sand 7 with a dry AI formulation 16, such as an Andersons GR formulation, topdressing material on top of elevator conveying means 8, where the elevator and blending device are located under hopper 15, and B) showing another embodiment for attaching a sprayer unit represented by a schematic circle comprising tank 3 located in between hopper 14 and 15, above blending unit 9 and elevator in position in between hopper 14 and hopper 15.
Figure 10A:
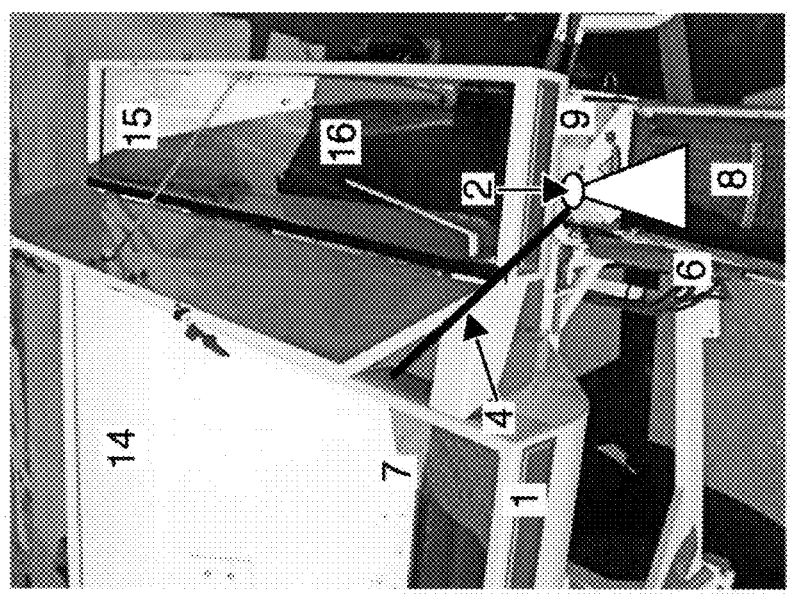
Figure 13A:
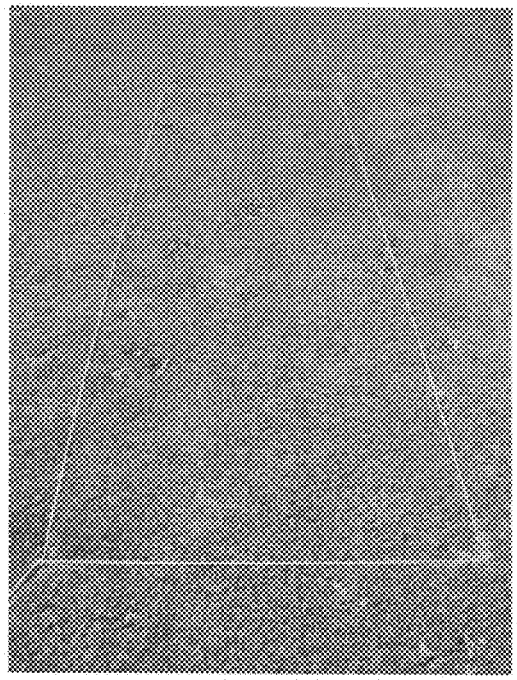
FIG. 13 shows exemplary test turf plots of annual bluegrass fairway turf that were naturally infected with Dollar Spot Fungi prior to testing formulations comprising Banner MaxxTM fungicide using vehicles of the present inventions showing comparable curative capabilities of a spray application of Banner Maxx™ fungicide applied using a 8002E flat fan two nozzle boom (1 fl oz/1000 sq ft), Treatment #1 (FIG. 13A), application of a treated sand formulation using a vehicle of the present invention, specifically a formulation of Banner MaxxTM fungicide sprayed on sand using two 8002E flat fan nozzles mounted on and while the sand was being applied by a 3' Mete-R-Matic finishing brush drop-type top
Figure 13B:
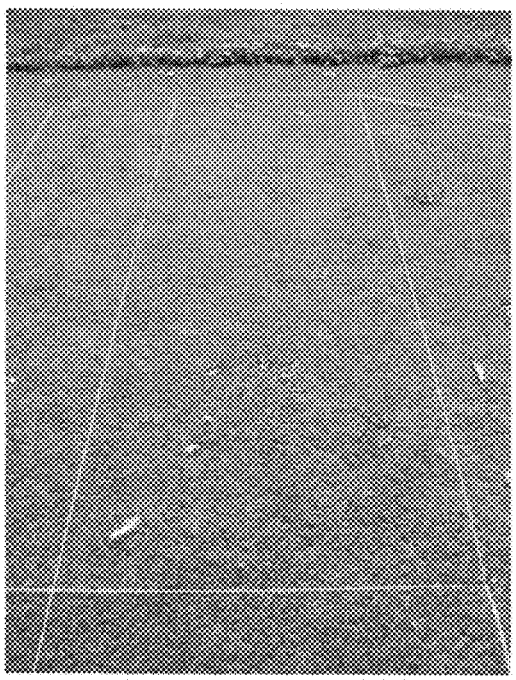
Figure 13C:
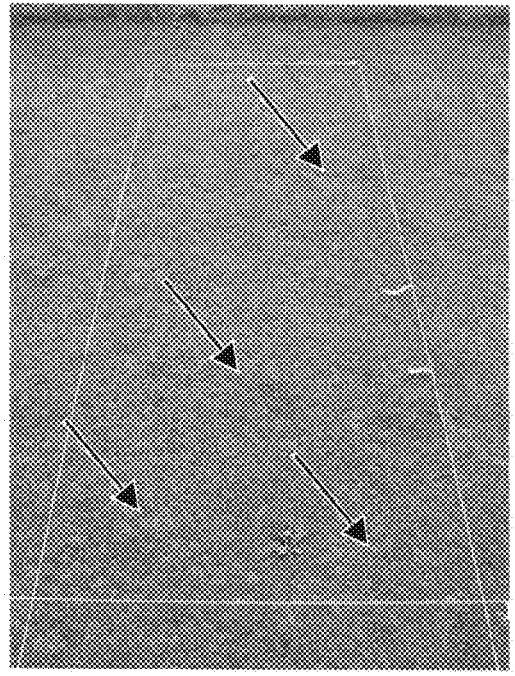
Figure 13D:
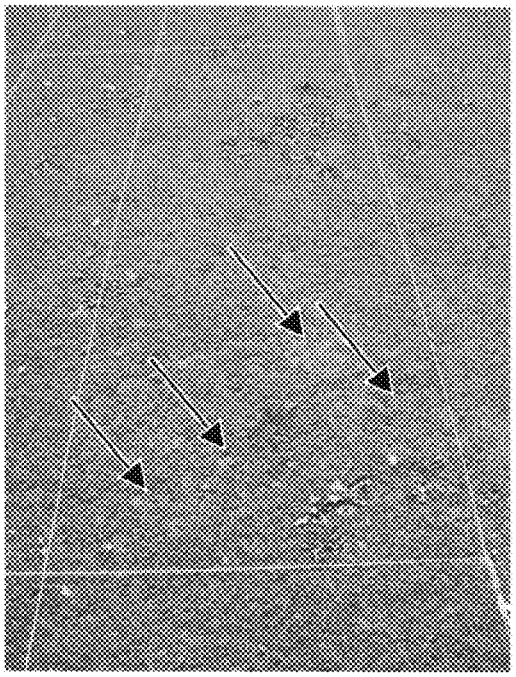
Figure 14A:
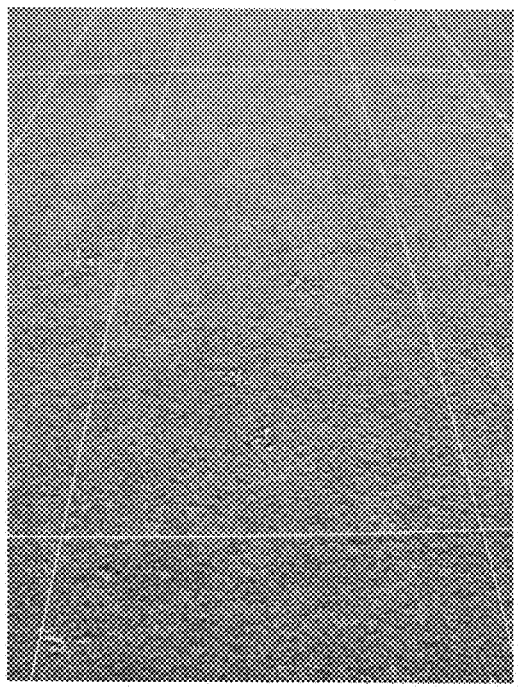
Figure 14B:
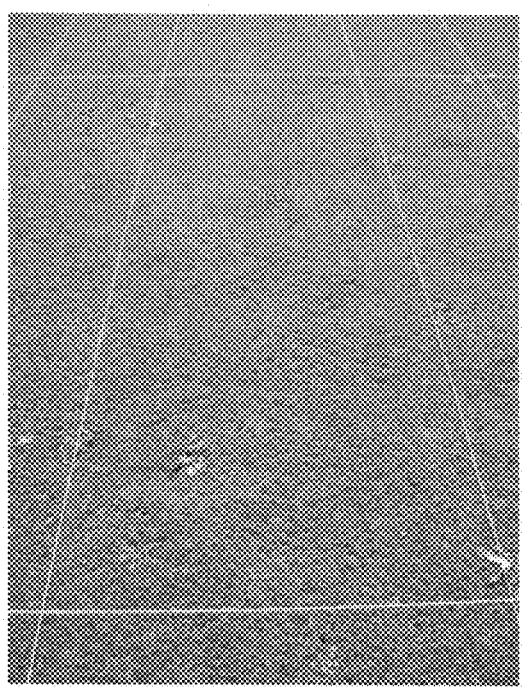
Figure 14C:
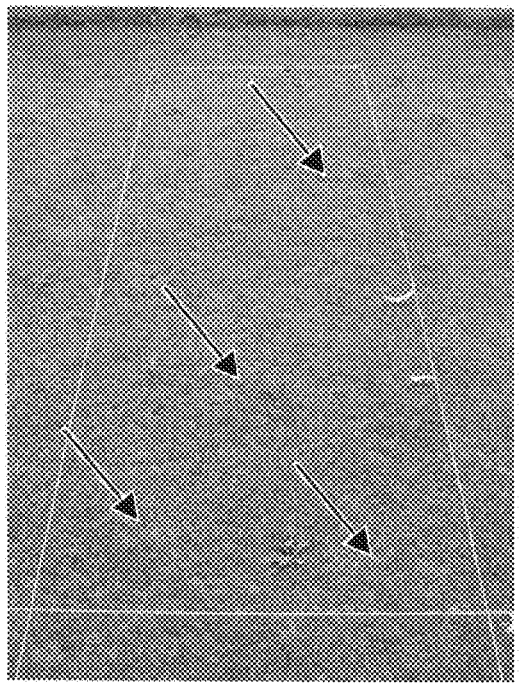
Figure 14D:
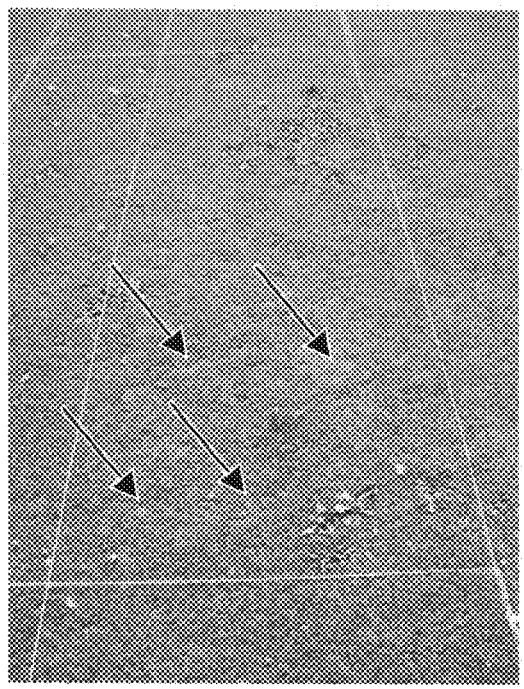
Figure 15A:
Figure 15B:
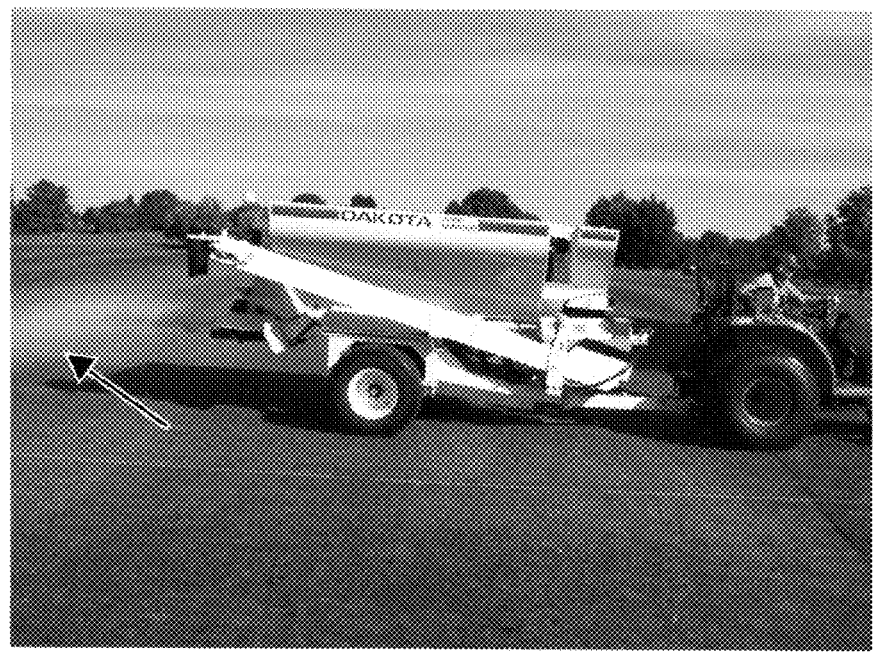
Figure 1:
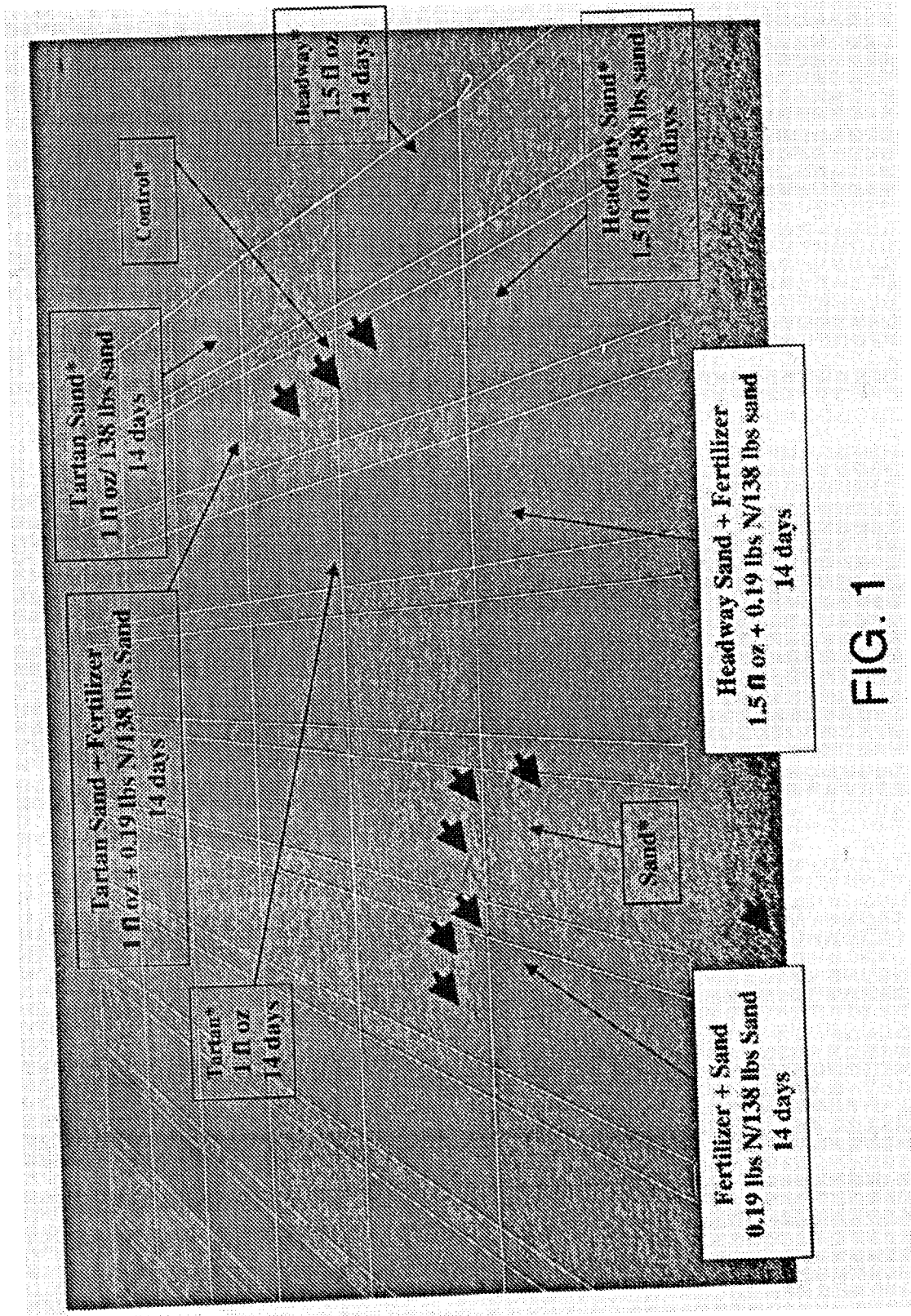
Figure 2:
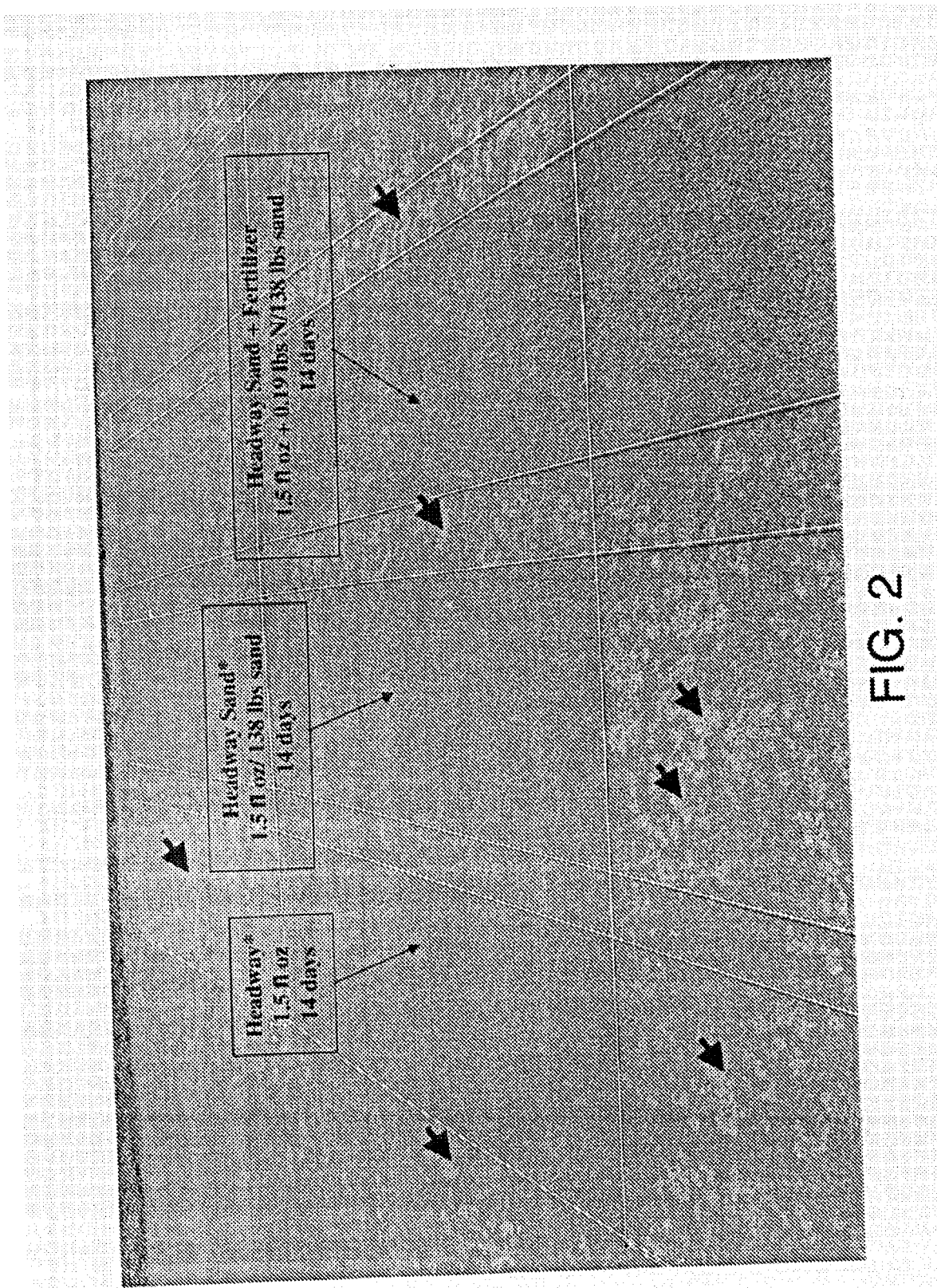
Figure 4A:
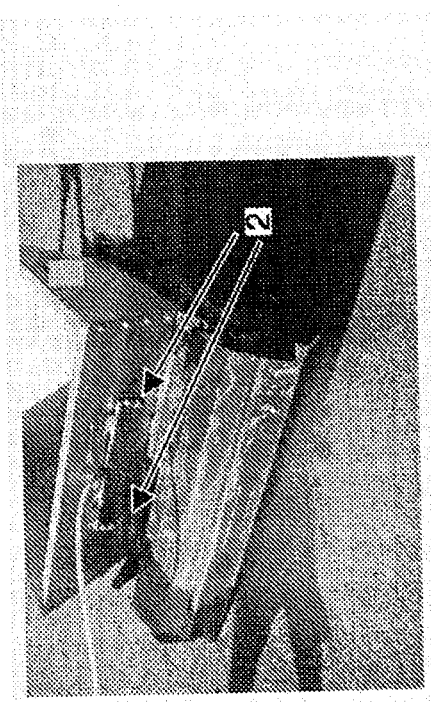
Figure 4B:
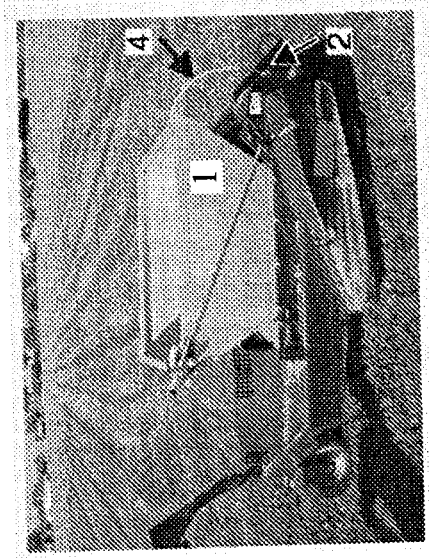
Figure 4C:
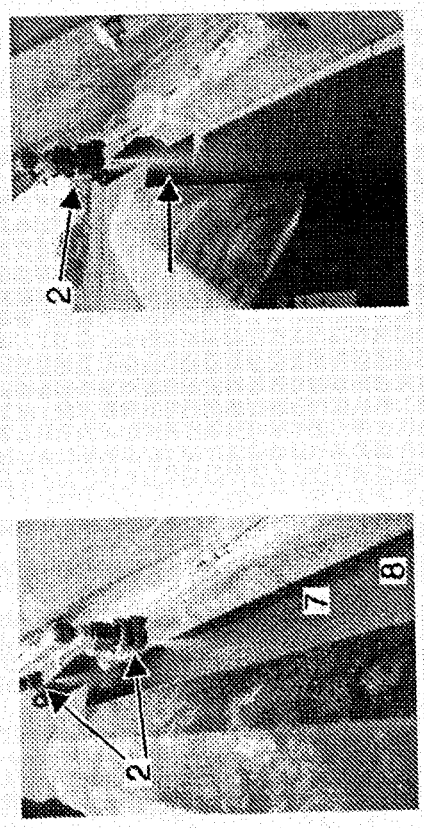
Figure 4D:
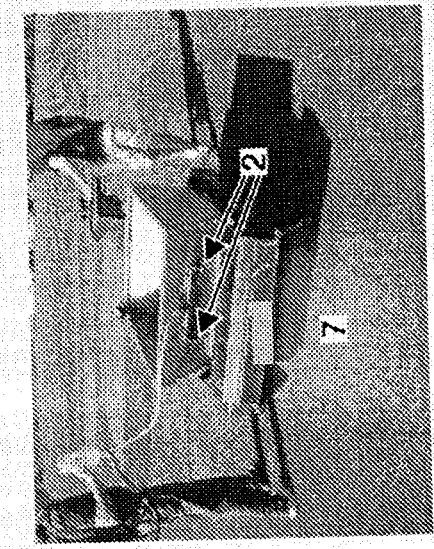
Figure 4E:
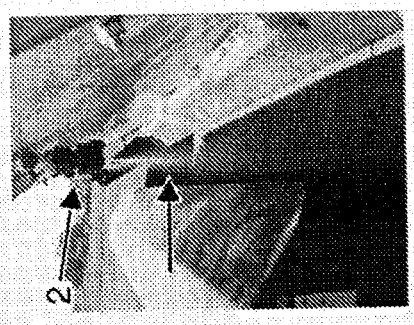
Figure 6B:
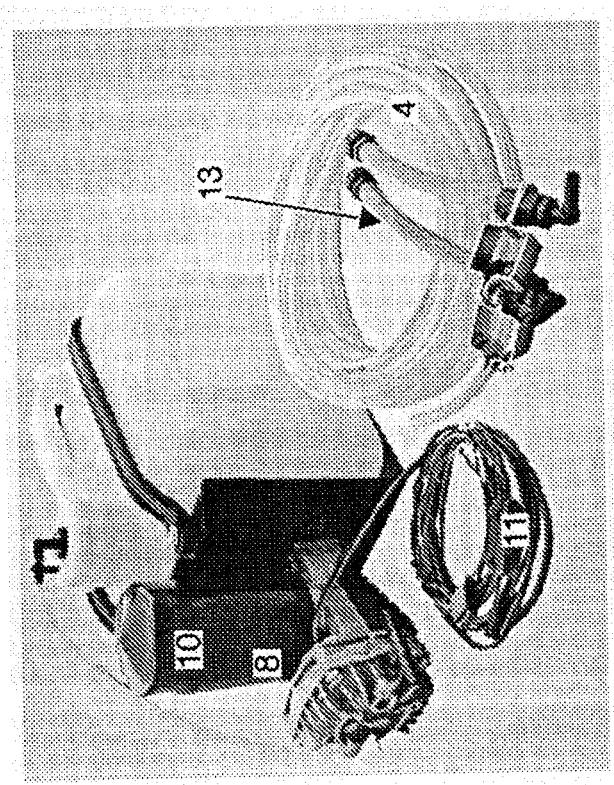
Figure 6A:
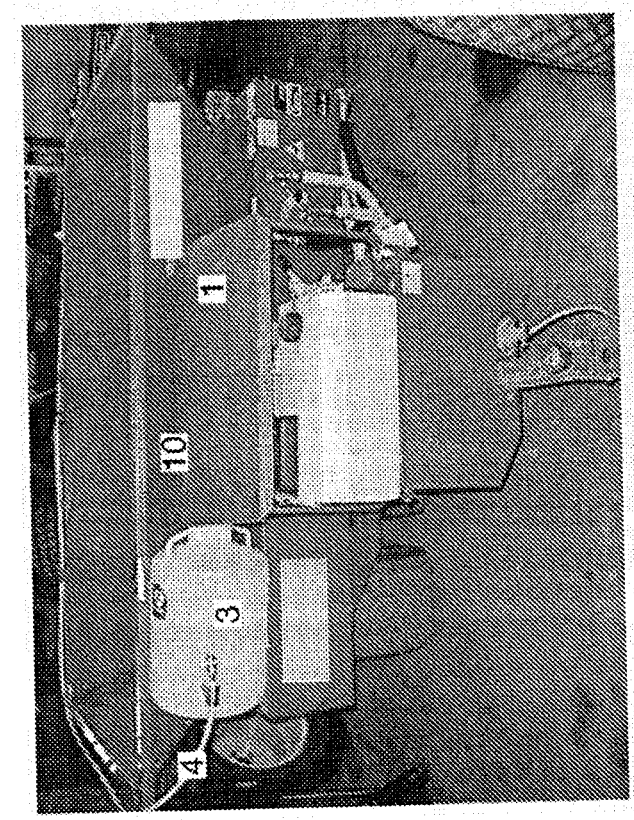

In another embodiment, the inventions provide a blending-type topdressing vehicle of the present inventions 1, wherein a sprayer unit is attached; see an exemplary topdressing vehicle in FIG. 9. In this example, a blending unit 9 capable of blending at least one additional material with a topdressing material is provided, where the attached nozzles are placed at the side and/or above the conveying means where the nozzles do not interfere with the operation or movement of the blending device into a nonoperable position. The blending device of the exemplary vehicle is shown in an operable location in FIG. 9A, and an inoperable location in FIG. 9B. Further, the exemplary topdressing vehicle shows a blender/elevator unit 6 attached with a conveying means 8. Thus in another embodiment, the nozzles are contemplated for attachment above the conveying means of the elevator for spraying a liquid onto the conveying means as shown schematically in FIG. 10A. In another embodiment, a schematic showing a contemplated location for an attached sprayer unit, as represented by tank 3, is shown in FIG. 10B. A further embodiment contemplates locating a spraying unit outside of or behind a second hopper attached to a topdressing vehicle or in place of a second hopper, where a second hopper is shown in FIGS. 10A, open, and 10B, closed, located in the front of this exemplary blender-type topdressing vehicle.

In a further embodiment, a topdressing vehicle of the present inventions is provided for coating a topdressing material. In this embodiment, the topdressing vehicle coats the topdressing without delivering it to an area of turf. As shown in FIG. 11, a schematic shows an attached sprayer, where the placement of a nozzle is above the conveying means. In this embodiment, the contemplated coated topdressing is provided in a moist form for subsequent disbursement. In a further embodiment, the moist formulations of the present inventions are contemplated to undergo subsequent drying prior to distribution onto an area of turf. The inventors contemplate air-drying and kiln drying of the formulations of the present inventions provided by the topdressing vehicles of the present inventions. The inventors do not intend to limit this type of coating to methods using topdressing vehicles, such that methods for coating a topdressing material with an A.I. comprises any type of spray device capable of spraying an A.I., such as a table or rotating drum mixer comprising a conveying means and a sprayer unit attached in a manner capable of providing spray coated sand formulations of the present inventions.

Figure 12A:
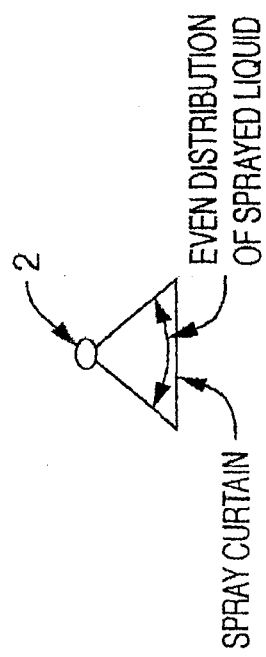
Figure 12B:
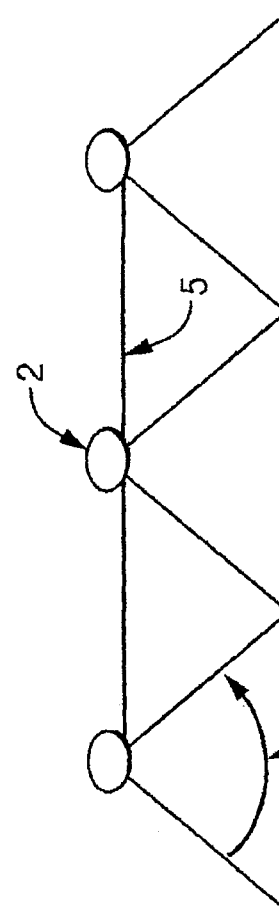
Figure 13A:
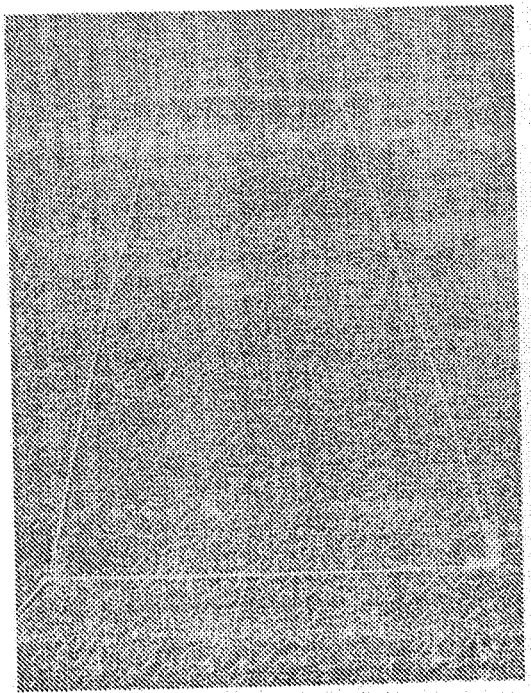
Figure 13B:
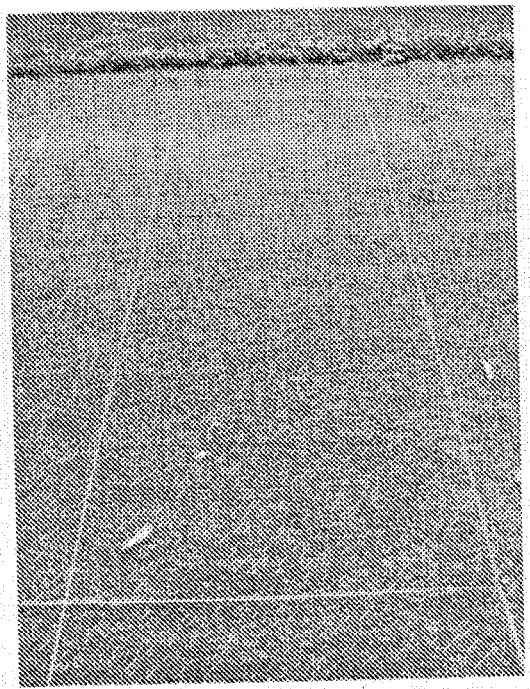
Figure 13C:
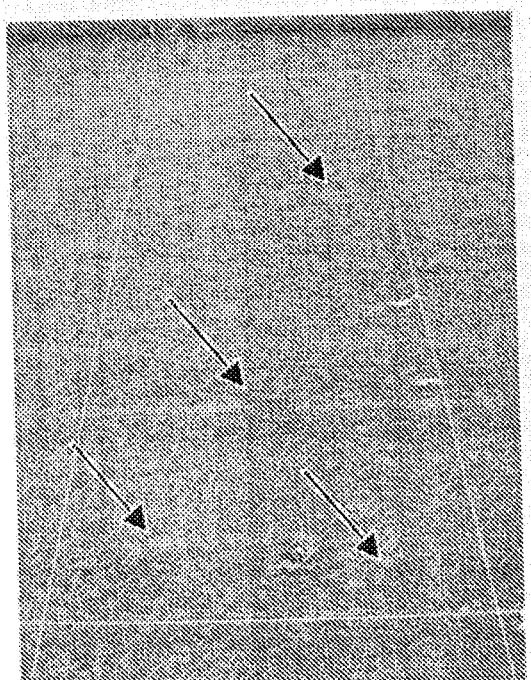
Figure 13D:
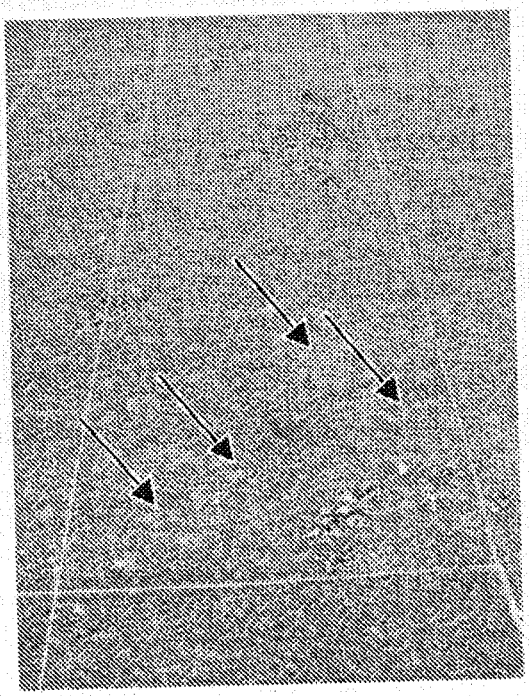
Figure 14A:
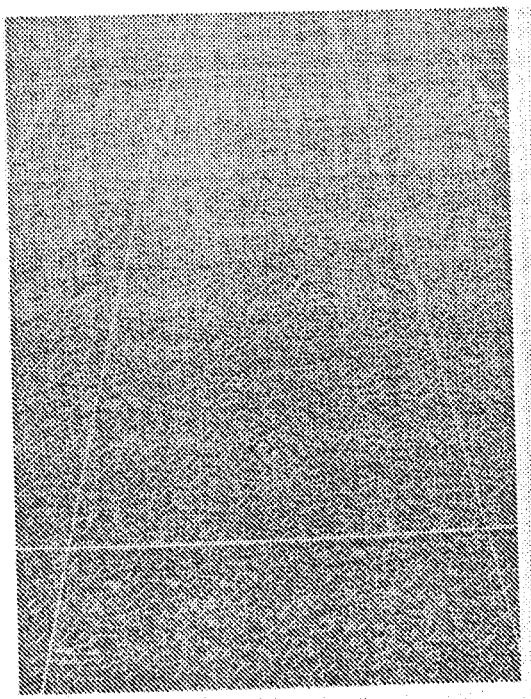
Figure 14B:
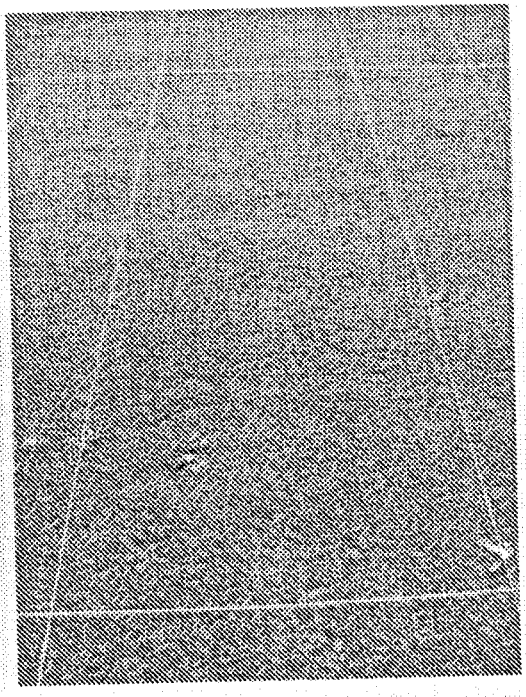
Figure 14C:
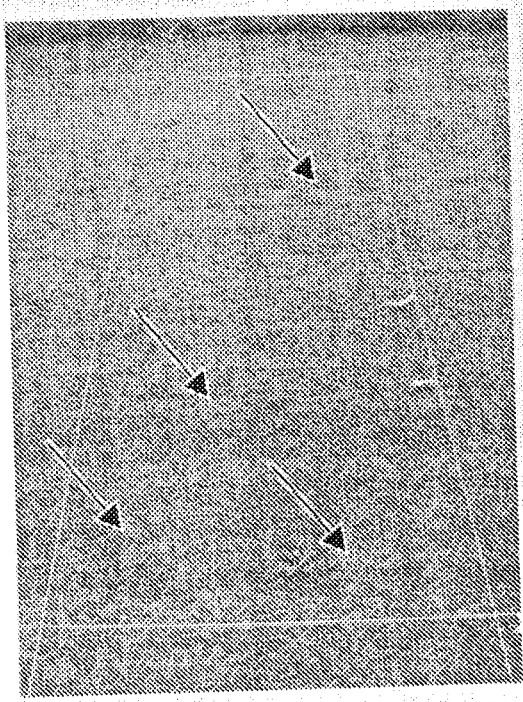
Figure 14D:
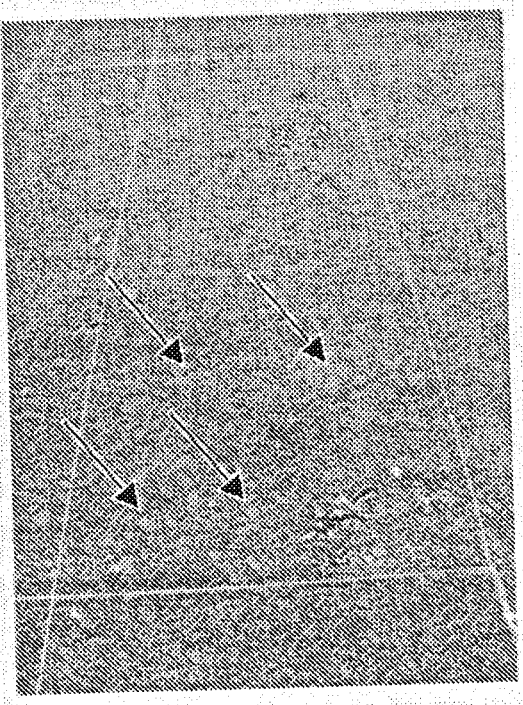
Figure 15A:
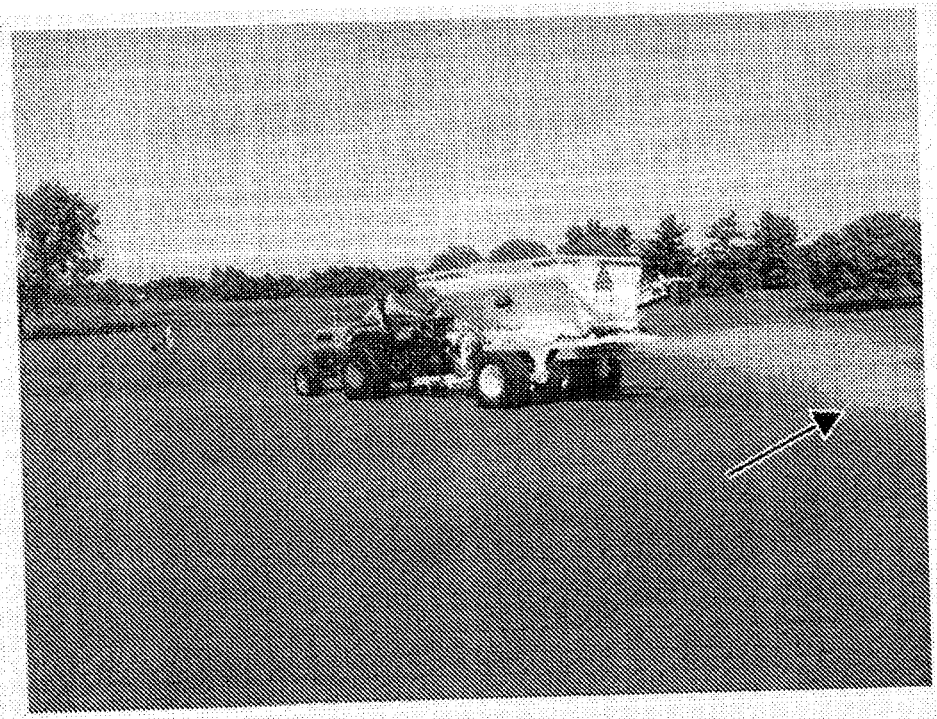
Figure 15B:
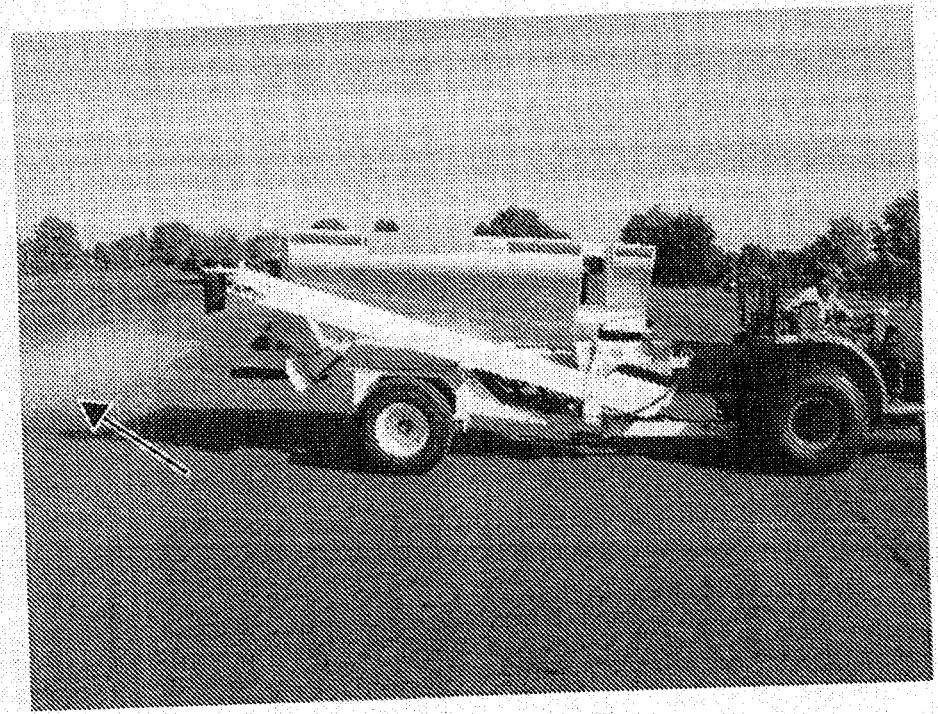

Exemplary spray curtains/patterns are provided in FIG. 12, wherein a schematic spray curtain formed by a single nozzle and two nozzles providing nonoverlapping spray curtains are shown in FIG. 12A. A schematic of an overlapping spray curtain is shown included in FIG. 12B, contemplated for attachment to topdressing vehicles of the present inventions and for use in spraying liquid formulations onto topdressing materials as provided herein.

Example VII

This example demonstrates the curative capability of treatments comprising dry formulations of the present inventions using a commercially available spinner-type Topdressing vehicle. Further, these results show superior results of treatments comprising a blended formulation consisting of sand and a granular/dry form of a fungicide, wherein the A.I. was propiconazole, as an Andersons Prophesy™ GR formulation over treatment comprising a blended formulation consisting of sand and chlorothalonil in the form of an Andersons 5% Daconil™ GR fungicide granule. For comparison, the same AIs were provided in liquid form and used as sprays.

The inventors tested dry formulations of the present inventions on an area of turf as part of the Forest Acres Golf Course, East Lansing, Mich. One dry formulation was provided by placing a topdressing sand material in the main hopper of a Dakota 440 TurfTender top dressing with a blending attachment 9 (see, FIG. 10) and placing the granular Andersons Prophesy™ GR in the smaller hopper leading to the blending unit. Another dry formulation was provided by placing Andersons 5% Daconil™ GR fungicide granule in the smaller hopper 15 for blending with sand as the sand was conveyed 8 to the spinner units 6.

The Dakota 440™ blended sand/granule application was a 1:27 blend of Andersons Prophesy™ GR (propiconazole) fungicide: moist sand (2.5 lbs/1000 sq. ft.: 67.5 lbs/1000 sq. ft.) applied in 2 trips (100% overlap) over the plots. The estimated total was 34-lbs/1000 sq ft of topdressing applied per trip. In one embodiment, the dry formulation was pre-blended with sand with the Dakota 440™ where the blender is mounted on the front of the vehicle with the blended material conveyed forward into a drop pile. The blended material was re-loaded into the main hopper for spreading with the conveyor belt moving the blended material towards and into the rear spinner unit.

For comparison, a spray solution being applied to sand on the Dakota 440 at a tank concentration of 3.8% Banner Maxx™ liquid comprising propiconazole, in other words 0.5 fl. oz. of tank solution was applied to 34 lbs topdressing sand/1000 sq. ft. with 2 trips over the plot with 100% overlap (1 fl. oz./1000 sq. ft. on 67.5 lbs sand). The spray was applied at 9 GPA. A foam marker unit was attached to the tractor towing the Dakota 440™ which provided a dotted line of foam, lasting approximately 15 minutes, which marked each trip allowing for an even distribution of the blended formulation.

Treatments of a usual sand volume application blended with Andersons Prophesy™ GR just prior to spreading were applied on areas of turf naturally infected with Dollar Spot fungi with visible brown areas. FIG. 15 shows the broadcast area and sand composition as an exemplary Dakota 440 spinner-type topdressing machine applied it. Arrows show the pattern of sand broadcast during application. Table 8 shows the curative capability of a dry formulation of blended sand comprising a propiconazole formulation application equivalent to a spray application of Banner Maxx™ (liquid propiconazole) spray and a Daconil™ Ultrex spray. In contrast, sand blended formulation of Andersons 5% Daconil™ GR fungicide did not appear to reduce fungal infection of the turfgrass.

The inventors discovered during test runs that several parameters of the Dakota 440 TurfTender™ had to be altered for using the Dakota 440 TurfTender™ in methods of distributing formulations of the present inventions. In particular, the blender-metering gate on the Dakota 440 TurfTender™ allowed the Anderson Prophesy™ granules to leak over the top of the metering gate, resulting in a higher blend rate than desired for that product. The inventors placed tape over the opening at the top of the gate, which stopped the excess granule distribution. Additionally, when the blender/elevator unit was in the operable position, granules exiting the blender bin tended to escape the blender unit and fall to the ground.

These leaks were sealed by the inventor prior to further treatments. Lastly, the rear-metering gate 12 on the Dakota 440 TurfTender machine 1 was insufficiently precise, under normal operation, to accurately apply pesticide granule/sand blends evenly across the spread swath. Therefore the inventors were required to begin providing specific calibration settings for use in the present inventions.

Further, the inventors discovered that when using the white spinner blade option, requiring one pass, they were unable to obtain a sufficiently consistent distribution of sand blended or sprayed with fungicide across the swath of distributed material. Specifically, the white spinner blades distributed the material too heavily near the machine and too lightly on the fringes of the swath. Testing the black spinner option, which requires for providing an overlap spread pattern, gave an acceptable distribution in the overlap pattern following two passes (100% overlap) of the topdresser.

TABLE 8

Forest Acres Dakota 440 ™ Top Dresser Dollar Spot Study, 2008.

| Trt No. | Treatment (Trt)[a] Name | Rate Amount | Rate Unit | Application Interval | Percent Dollar Spot per plot area on Sep. 18, 2008* Data By Rep 1 | 2 | 3 | 4 | Mean | LSD[b] |
|---|---|---|---|---|---|---|---|---|---|---|
| 1 | Andersons Prophesy ™ GR applied by hand | 2.5 | lbs/1000 ft2 | 14 days | 0 | 0 | 3 | 3 | 1.5 | B |
| 2 | Andersons Prophesy ™ GR/Sand hand blended and applied by hand | 2.5/67.5 | lbs/1000 ft2 | 14 days | 0 | 0 | 0 | | 0.0 | B |
| 3 | Andersons Prophesy ™ GR/Sand blended and applied with a Dakota 440 ™ Topdresser | 2.5/67.5 | lbs/1000 ft2 | 14 days | 0 | 0 | 0 | 0 | 0.0 | B |
| 4 | Sand applied by hand | 67.5 | lbs/1000 ft2 | 14 days | 5 | 15 | 40 | 15 | 18.8 | A |
| 5 | Untreated control without sand | | | | 7 | 20 | 35 | 35 | 24.3 | A |
| 6 | Andersons 5% DaconilTM ™ GR fungicide applied by hand | 3.35 | lbs/1000 ft2 | 14 days | 1 | 10 | 25 | 35 | 17.8 | A |
| 7 | Andersons 5% DaconilTM ™ GR fungicide/sand hand blended and applied by hand | 3.35/67.5 | lbs/1000 ft2 | 14 days | 5 | 20 | 10 | 35 | 17.5 | A |
| 8 | Andersons 5% DaconilTM ™ GR fungicide/sand blended and applied with a Dakota 440 Topdresser | 3.35/67.5 | lbs/1000 ft2 | 14 days | 20 | 25 | 25 | 15 | 21.3 | A |
| 9 | Banner Maxx ™ spray | 1 | fl oz/1000 ft2 | 14 days | 0 | 0 | 0 | 0 | 0.0 | B |
| 10 | DaconilTM Ultrex ™ spray | 3.2 | oz/1000 ft2 | 14 days | 0 | 3 | 0 | 3 | 1.5 | B |

*Treatments applied on Aug. 22, 2008 and Sep. 4, 2008.

[Sprayed treatments]were applied using a $CO_2$-powered backpack sprayer with a double nozzle (8002E) boom at 96 GPA with 40 PSI.

[b]Treatment means followed by the same letter are not significantly different from each other (p = 0.05).

Further types of blended mixtures were provided and used as test treatments. In particular, treatments comprising 90:10 sand:peat blends were sprayed with Banner Maxx™ fungicide and then used for treating turf infected with Dollar spot fungus for determining whether peat affected the efficacy and/or duration of fungal control using an effective formulation of Propiconazole in the form of Banner Maxx™ fungicide (Active Ingredient: propiconazole: (CAS No. 60207-90-1) 14.3%, contains a nominal 1.3 pounds of active ingredient per gallon (Label) (Syngenta Crop Protection, Inc. Greensboro, N.C. 27409).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in grounds keeping, green keeping, turf grass plants, turf grass fields, chemistry, botany, or related fields are intended to be within the scope of the following claims.

The invention claimed is:

1. A top dressing vehicle, wherein said vehicle is of a weight that avoids compaction of turf, comprising, a dispensing unit, a conveying means and a sprayer, wherein the sprayer comprises a tank of 5-50 gallons, wherein the sprayer comprises a pump, a regulator valve, a hose, and a nozzle, wherein said nozzle is capable of applying a spray volume in the range of 9-50 gallons to an amount of top dressing for covering one acre of turfgrass, wherein the nozzle is attached in a position for spraying a liquid in between the conveying means and the dispensing unit, wherein the dispensing unit is selected from the group consisting of a blending device, an elevator, a drop spreader, a brush spreader, and a spinner spreader.

2. A method for making an apparatus, comprising,
   a) providing,
      i) a top dressing vehicle, wherein said vehicle is of a size that avoids compaction of turf, selected from the group consisting of a blender machine, a drop spreading machine, a spinner spreading machine, and an elevator machine, wherein said vehicle comprises a conveying means and a dispensing unit; and
      ii) a sprayer unit comprising a tank, wherein said tank is selected from the group consisting of 5, 10, 20, 30, 40 and up to 50 gallon liquid tanks, a pump, a hose, and a nozzle, and
   b) attaching said nozzle of the sprayer unit to said top dressing vehicle in a position selected from the group consisting of a position for spraying a liquid in between the conveying means and the dispensing unit and a position for spraying a liquid onto the conveying means.

3. The method of claim 2, further comprising, attaching the tank to said top dressing vehicle.

4. The method of claim 2, further comprising, attaching the hose to said top dressing vehicle.

5. The method of claim 2, further comprising step c) attaching at least one element selected from the group consisting of a foam-marking unit, a foam ejector, a foam outlet tube, a flow rate adjuster unit, and a calibration aid to a top dressing vehicle.

6. A method of using a top dressing vehicle, comprising,
   a) providing,
      i) a top dressing material,
      ii) a sprayable formulation, comprising an agriculturally active ingredient for treating a top dressing material,
      iii) a top dressing vehicle, comprising a conveying means, and a sprayer unit, comprising a nozzle, wherein said sprayer unit is capable of spraying the formulation onto a top dressing material, and
   b) spraying the formulation onto the top dressing material while the top dressing material is in the vehicle with the nozzle of the sprayer unit of the top dressing vehicle for providing a treated top dressing material.

7. The method of claim 6, wherein during the spraying of step b) the top dressing material is moving through the spray.

8. The method of claim 6, wherein the agriculturally active ingredient is selected from the group consisting of a fungicide, insecticide, herbicide, plant growth regulator, soil wetting agent, fertilizer, plant hormone, plant extract, biological control agent, and plant nutrients.

9. The method of claim 6, wherein the sprayer unit is attached to the top dressing vehicle.

10. The method of claim 6, wherein said top dressing vehicle further comprises a dispensing unit.

11. The method of claim 10, wherein the dispensing unit is selected from the group consisting of a blending device, a drop spreader, a brush spreader, a spinner spreader, an elevator, and a broadcast spreader.

12. The method of claim 10, wherein said treated top dressing continues to move to a dispensing unit.

13. The method of claim 12, wherein said treated top dressing is dispensed onto turf by said dispensing unit.

14. The method of claim 6, wherein said top dressing material comprises sand.

15. The method of claim 6, wherein said top dressing material is selected from the group consisting of sand, peat, soil, and blends thereof.

16. The method of claim 6, wherein said nozzle is capable of applying a spray volume in the range of 9-50 gallons to an amount of top dressing for covering one acre of turfgrass.

17. The top dressing vehicle of claim 6, wherein said small tank is selected from a range of 5-50 gallon liquid tanks.

18. The method of claim 6, wherein said sprayer applies from 0.01 ounce-8 ounces of agriculturally active ingredient per 1000 square foot of top dressing material.

19. The method of claim 6, wherein the top dressing vehicle further comprises a foam-marking unit, a foam ejector, a foam outlet tube, a flow rate adjuster unit, and a calibration aid.

* * * * *

UNITED STATES PATENT AND TRADEMARK OFFICE
CERTIFICATE OF CORRECTION

| | | |
|---|---|---|
| PATENT NO. | : 8,028,928 B2 | |
| APPLICATION NO. | : 12/288193 | |
| DATED | : October 4, 2011 | |
| INVENTOR(S) | : Ronald A. Detweiler, Nancy M. Dykema and Joseph M. Vargas | |

It is certified that error appears in the above-identified patent and that said Letters Patent is hereby corrected as shown below:

The title page, showing an illustrative Figure, should be deleted and substitute therefor the attached title page In the Drawings Please delete Drawing Sheets 1-17 and replace with attached Drawing Sheets 1-16, which drawing sheets consist of Figures 1, 2, 3A-3B, 4A-4E, 5A-5B, 6A-6B, 7A-7C, 8A-8E, 9A-9B, 10A-10B, 11A-11B, 12A-12B, 13A-13D, 14A-14D and 15A-15B.

In the Specification

Pat col. 1/Line 67: Error reads as "produced turf compaction and interfered" and should read as "produce turf compaction and interfere"

Pat col. 2/Line 2: Error reads as "areas in" and should read as "areas, in"

Pat col. 3/Line 24: Error reads as "and ii) b)" and should read as "and b)"

Pat col. 5/Line 57: Error reads as "fertilizer, refers to" and should read as "fertilizer, the term "soluble" refers to"

Pat col. 6/Line 9: Error reads as "regulator, composition that have" and should read as "regulator, or composition that has"

Pat col. 6/Line 40: Error reads as "refer" and should read as "refers"

Pat col. 6/Line 55: Error reads as "activates" and should read as "activities"

Signed and Sealed this
Eighth Day of July, 2014

Michelle K. Lee
*Deputy Director of the United States Patent and Trademark Office*

CERTIFICATE OF CORRECTION (continued)
U.S. Pat. No. 8,028,928 B2

Pat col. 7/Line 60: Error reads as "7.0 mm" and should read as "7.0 mm."

Pat col. 8/Line 49: Error reads as "invention, for" and should read as "invention. For"

Pat col. 8/Line 56: Error reads as "presenting" and should read as "present"

Pat col. 9/Line 11: Error reads as "pest" and should read as "pests,"

Pat col. 9/Lines 44-45: Error reads as "mowing, examples include," and should read as "mowing. Examples include"

Pat col. 9/Line 46: Error reads as "the like, in particular" and should read as "the like, and in particular"

Pat col. 9/Line 55: Error reads as "lawn, in" and should read as "lawn. In"

Pat col. 11/Lines 4-21: Delete selection- duplicate text from columns 5-6

Pat col. 11/Lines 25-37: Delete selection- duplicate text from column 6

Pat col. 13/Line 7: Error reads as "direct, bolts" and should read as "direct, such as bolts"

Pat col. 13/Line 8: Error reads as "indirect, for example" and should read as "indirect, including, for example"

Pat col. 13/Line 44: Error reads as "it growth check," and should read "its growth in check"

Pat col. 14/Line 3: Error reads as "substances" and should read as "substance"

Pat col. 14/Line 16: Error reads as "formulation, for example" and should read as "formulation, such as, for example"

Pat col. 14/Line 43: Error reads as "Potassium often" and should read as "Potassium is often"

Pat col. 14/Lines 49-50: Error reads as "stage, examples include, Miracle-Gro" and should read as "stage. Examples include Miracle-Gro"

Pat col. 14/Line 54: Error reads as "nutrition, for" and should read as "nutrition, including, for"

Pat col. 15/Line 32: Error reads as "*Treatments" and should read as "Treatments"

Pat col. 18/Lines 66-67: Error reads as "2004, at world wide web.ncturfgrass.org (at world wide web.ncturfgrass.org/pdf/july/JulyAugustPage14Link.pdf)" and should read as "2004, www.ncturfgrass.org/pdf/july/JulyAugustPage14Link.pdf"

CERTIFICATE OF CORRECTION (continued)
U.S. Pat. No. 8,028,928 B2

Pat col. 19/Line 51: Error reads as "soil pH, for" and should read as "soil pH. For"

Pat col. 19/Line 56: Error reads as "prone this" and should read as "prone to this"

Pat col. 20/Line 22: Error reads as "loosing" and should read as "losing"

Pat col. 20/Line 24: Error reads as "matrix however" and should read as "matrix. However,"

Pat col. 20/Line 31: Error reads as "further mere" and should read as "mere"

Pat col. 20/Line 36: Error reads as "looses" and should read as "losses"

Pat col. 20/Line 60: Error reads as "explain" and should read as "explaining"

Pat col. 20/Line 62: Error reads as "particular combined" and should read as "particular, when combined"

Pat col. 20/Line 66: Error reads as "further, these" and should read as "further, there"

Pat col. 21/Line 8: Error reads as "personal" and should read as "personnel"

Pat col. 21/Lines 39-40: Error reads as "world wide web.horizononline.com" and should read as "www.horizononline.com."

Pat col. 21/Lines 48-49: Error reads as "world wide web.harfordmineral-s.net/topdressing.html" and should read as "www.harfordminerals.net/topdressing.html"

Pat col. 22/Line 3: Error reads as "plants, Bermuda" and should read as "plants or Bermuda"

Pat col. 22/Line 5: Error reads as "plants, see" and should read as "plants. See"

Pat col. 22/Line 46: Error reads as "application, in particular providing" and should read as "application, and, in particular, the inventors contemplated providing"

Pat col. 22/Line 49: Error reads as "like)" and should read as "like,"

Pat col. 22/Line 52: Error reads as "like)." and should read as "like."

Pat col. 24/Lines 7-8: Error reads as "(see, at world wide web.dakotapeat.com/news/equipment/022508.html" and should read as "(See www.dakotapeat.com/news/equipment/022508.html".

Pat col. 24/Lines 21-22: Error reads as "(see, at world wide web.turfco.com/html/osforsptd.htm," and should read as "(See www.turfco.com/html/osforsptd.htm,"

CERTIFICATE OF CORRECTION (continued)

U.S. Pat. No. 8,028,928 B2

Pat col. 24/Lines 58-59: Error reads as "comprise" and should read as "comprises"

Pat col. 24/Line 60: Error reads as "compounds however" and should read as "compounds. However"

Pat col. 25/Lines 22-23: Error reads as "http://at worldwide web.plantman-agementnetwork.org/pub/php/research/2003/dollar/, and should read as "www.plantmanagementnetwork.org/pub/php/research/2003/dollar/,"

Pat col. 25/Line 28: Error reads as "reference, benzoyl" and should read as "reference, such as benzoyl"

Pat col. 25/Line 30: Error reads as "example, those" and should read as "example, and those"

Pat col. 25/Line 31: Error reads as "reference)," and should read as "reference,"

Pat col. 25/Line 36: Error reads as "reference), and 4-trifluoromethylpyrazolyl-substituted" and should read as "reference, and 4-trifluoromethylpyrazolyl-substituted"

Pat col. 26/Line 16: Error reads as "but not" and should read as "but are not"

Pat col. 26/Line 58: Error reads as "examples" and should read as "example"

Pat col. 27/Line 62: Error reads as "delivery" and should read as "deliver"

Pat col. 28/Line 4: Error reads as "unit are of turf" and should read as "unit area of turf"

Pat col. 28/Line 10: Error reads as "inventions. Depending" and should read as "inventions depend"

Pat col. 28/Line 12: Error reads as "sand, the " and should read as "sand. The"

Pat col. 28/Line 17: Error reads as "contemplated" and should read as "contemplate"

Pat col. 29/Line 12: Error reads as "that at" and should read as "at a"

Pat col. 29/Lines 17-18: Error reads as "peat see examples described herein" and should read as "peat. (See examples described herein)."

Pat col. 29/Line 28: Error reads as "embodiment In one embodiment, the" and should read as "embodiment, the"

Pat col. 29/Line 54: Error reads as "amount that" and should read as "amount, such that"

Pat col. 30/Lines 8-9: Error reads as "easy to mix, handle and apply; controlled" and should read as "provide ease of mixing, handling and applying, and controlled"

Pat col. 30/Line 26: Error reads as "tend granules" and should read as "granules tend to"

Pat col. 30/Lines 35-36: Error reads as "contemplate" and should read as "contemplated"

Pat col. 32/Line 9: Error reads as "design" and should read as "designed"

Pat col. 32/Line 19: Error reads as "matter so" and should read as "matter,"

Pat col. 33/Lines 10-11: Error reads as "The inventors further contemplate compositions of the present inventions comprising" - DELETE Pat col. 33/Line 13: Error reads as "a" and should read as "as"

Pat col. 34/Line 57: Error reads as "contain" and should read as "contains"

Pat col. 36/Line 22: Error reads as "penetrated" and should read as "penetrate"

Pat col. 37/Line 58: Error reads as "disclose" and should read as "disclosed"

Pat col. 37/Lines 62-63: Error reads as "are herein incorporated in their" and should read as "is herein incorporated in its"

Pat col. 38/Line 14: Error reads as "spryer" and should read as "sprayer"

Pat col. 38/Line 20: Error reads as "contemplate top" and should read as "contemplate a top"

Pat col. 38/Line 24: Error reads as "nozzles. Specifically" and should read as "nozzles, i.e., specifically"

Pat col. 39/Line 31: Error reads as "include:" and should read as "including:"

Pat col. 40/Lines 15-17: Error reads as "Exemplary topdressers/machines include but are not limited to the following vehicles." - DELETE Pat col. 40/Line 29: Error reads as "spreading, sand" and should read as "spreading sand"

Pat col. 40/Line 31: Error reads as "material, listed with a capacility" and should read as "material, the BTD-05 is listed with a capacity"

Pat col. 40/Line 33: Error reads as "powered" and should read as "is powered"

Pat col. 40/Line 34: Error reads as "pack, a" and should read as "pack, and has a"

Pat col. 40/Line 35: Error reads as "surface, in particular" and should read as "surface. In particular,"

CERTIFICATE OF CORRECTION (continued)
U.S. Pat. No. 8,028,928 B2

Pat col. 40/Line 36: Error reads as "providing" and should read as "provide"

Pat col. 40/Line 38: Error reads as "world wide web.sportsturfmagic.com" and should read as "www.sportsturfmagic.com)."

Pat col. 41/Line 28: Error reads as "is application to" and should read as "is applicable to"

Pat col. 41/Line 50: Error reads as "contemplated, however" and should read as "contemplated. However"

Pat col. 41/Line 63: Error reads as "built in, for" and should read as "built-in. For"

Pat. col. 41/Line 64: Error reads "is" and should read "may be"

Pat col. 41/Line 65: Error reads as "vehicle, tank holding clamps or straps, hose clips, are" and should read as "vehicle; tank holding clamps or straps, or hose clips may be"

Pat col. 42/Line 6: Error reads as "to top" and should read as "to a top"

Pat col. 42/Line 13: Error reads as "topdressers. Such that in another" and should read as "topdressers. In another"

Pat col. 42/Line 67: Error reads as "recommended in Beard" and should read as "recommended in the Beard references."

Pat col. 43/Line 10: Error reads as "chemicals, however" and should read as "chemicals. However,"

Pat col. 43/Line 12: Error reads as "greater. Such that," and should read as "greater, such that"

Pat col. 43/Line 40: Error reads as "need" and should read as "needed"

Pat col. 43/Line 41: Error reads as "possible while" and should read as "possible, while"

Pat col. 43/Line 46: Error reads as "accomodate, thus the" and should read as "accomodate. Thus, the"

Pat col. 43/Line 58: Error reads as "stuffiest" and should read as "sufficient"

Pat col. 43/Line 66: Error reads as "worldwide web.masspray.com" and should read as "www.masspray.com"

Pat col. 44/Lines 5-6: Error reads as "In another exemplar speed" and should read as "In another embodiment, an exemplary speed"

Pat col. 44/Line 55: Error reads as "spinners, as" and should read as "spinners. As one"

Pat col. 44/Line 66: Error reads as "nozzles. Such that," and should read as "nozzles), such that,"

Pat col. 45/Line 8: Error reads as "volume to for" and should read as "volume for"

Pat col. 45/Line 41: Error reads as "nozzle close" and should read as "nozzle as close as"

Pat col. 46/Line 1: Error reads "amounts of spray amounts." and should read as "amounts of spray."

Pat col. 46/Line 4: Error reads as "contemplate nozzles using" and should read as "contemplate using"

Pat col. 46/Line 10: Error reads as "has 2 ideal locations" and should read as "two ideally located"

Pat col. 46/Line 14: Error reads as "examples," and should read as "example,"

Pat col. 46/Line 25: Error reads as "with FIGS." and should read as "with vehicles shown in FIGS."

Pat col. 46/Line 63: Error reads "specific to for" and should read "specific to"

Pat col. 47/Line 2: Error reads as "dryer" and should read as "drier"

Pat col. 47/Line 14: Error reads as "over less error in " and should read as "as compared with"

Pat col. 47/Lines 15-16: Error reads as "In other words, spraying" and should read as "In other words, when spraying"

Pat col. 47/Line 47: Error reads as "wherein example" and should read as "wherein an example"

Pat col. 47/Line 48: Error reads as "include a" and should read as "includes a"

Pat col. 47/Line 57: Error reads as "In further" and should read as "In a further"

Pat col. 48/Line 7: Error reads as "vehicle, thus in" and should read as "vehicle. Thus, in"

Pat col. 48/Line 9: Error reads as "speed, however other" and should read as "speed. However, other"

Pat col. 48/Line 10: Error reads as "to calculate" and should read as "to be calculated"

Pat col. 48/Line 11: Error reads as "axel" and should read as "axle"

Pat col. 48/Line 22: Error reads as "over doses" and should read as "overdoses"

Pat col. 48/Line 47: Error reads as "reference, which discloses" and should read as "reference, discloses"

CERTIFICATE OF CORRECTION (continued)
U.S. Pat. No. 8,028,928 B2

Pat col. 48/Line 50: Error reads as "represent" and should read as "representative"

Pat col. 48/Line 52: Error reads as "World Wide Web richway.com/turftracker.pdf" and should read as "www.richway.com/tracker.pdf"

Pat col. 49/Lines 21-22: Error reads as "world wide web richway.com/buyersguide.pdf" and should read as "www.richway.com/buyersguide.pdf"

Pat col. 49/Line 33: Error reads as "inventors' contemplate" and should read as "inventors contemplate"

Pat col. 49/Line 42: Error reads as "blended they are used, in other" and should read as "blended as they are used. In other"

Pat col. 49/Line 45: Error reads as "inventors' contemplate" and should read as "inventors contemplate"

Pat col. 49/Line 47: Error reads as "available and formulations" and should read as "available formulations"

Pat col. 50/Line 8: Error reads as "are" and should read as "were"

Pat col. 50/Line 24: Error reads as "each plots" and should read as "each plot"

Pat col. 50/Line 50: Error reads as "because over time the" and should read as "because the"

Pat col. 50/Lines 51-52: Error reads as "over time of the" and should read as "over the"

Pat col. 51/Line 7: Error reads as "as 9.54%, in other words" and should read as "9.54%. In other words,"

Pat col. 51/Line 8: Error reads as "as azoxystrobin per gallon) in" and should read as "(as azoxystrobin per gallon) was used in"

Pat col. 53/Line 52: Error reads as "are place on" and should read as "are placed on"

Pat col. 57/Line 40: Error reads as "formulation of" and should read as "formulations of"

Pat col. 60/Line 54: Error reads as "formulation of" and should read as "formulations of"

(12) United States Patent
Detweiler et al.

(10) Patent No.: US 8,028,928 B2
(45) Date of Patent: Oct. 4, 2011

(54) SPREADER APPARATUS FOR SAND BASED FORMULATIONS

(75) Inventors: A. Ronald Detweiler, Okemos, MI (US); Nancy M. Dykema, Holt, MI (US); Joseph M. Vargas, Jr., East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 162 days.

(21) Appl. No.: 12/288,193

(22) Filed: Oct. 17, 2008

(65) Prior Publication Data
US 2009/0151243 A1 Jun. 18, 2009

Related U.S. Application Data

(60) Provisional application No. 61/002,898, filed on Nov. 13, 2007.

(51) Int. Cl.
*B05B 17/04* (2006.01)
(52) U.S. Cl. ....... 239/7; 239/214.25; 239/662; 239/663; 239/672; 239/681; 504/261
(58) Field of Classification Search ............ 239/7, 172, 239/214.25, 661, 662, 663, 667, 672, 673, 239/679, 681; 504/261
See application file for complete search history.

(56) References Cited

U.S. PATENT DOCUMENTS

| | | | | |
|---|---|---|---|---|
| 4,886,208 A * | 12/1989 | Strand | | 239/662 |
| 5,860,604 A * | 1/1999 | Kooiker | | 239/672 |
| 6,336,600 B1 * | 1/2002 | Jessen | | 239/663 |
| 7,370,818 B2 * | 5/2008 | Ward et al. | | 239/662 |
| 2004/0077500 A1 * | 4/2004 | Sakata et al. | | 504/261 |
| 2006/0006256 A1 * | 1/2006 | Smith et al. | | 239/672 |

* cited by examiner

*Primary Examiner* — Steven J Ganey
(74) *Attorney, Agent, or Firm* — Melden & Carroll, LLP

(57) ABSTRACT

The present inventions relate to top dressing vehicles for coating, mixing, and dispensing compositions of top dressing materials comprising agriculturally active ingredients (A.I.s). More particularly, these inventions relate to apparatus for spraying liquid formulations comprising active ingredients A.I.s onto top dressing materials prior to and during delivering top dressing applications. Further, these inventions relate to applying liquids comprising A.I.s to top dressing materials at a point-of-application. Even further, these inventions relate to delivering treated top dressing, specifically, to broadcast spreading of top dressing comprising sand and agriculturally active ingredients as moist and dry compositions.

19 Claims, 16 Drawing Sheets
(4 of 16 Drawing Sheet(s) Filed in Color)

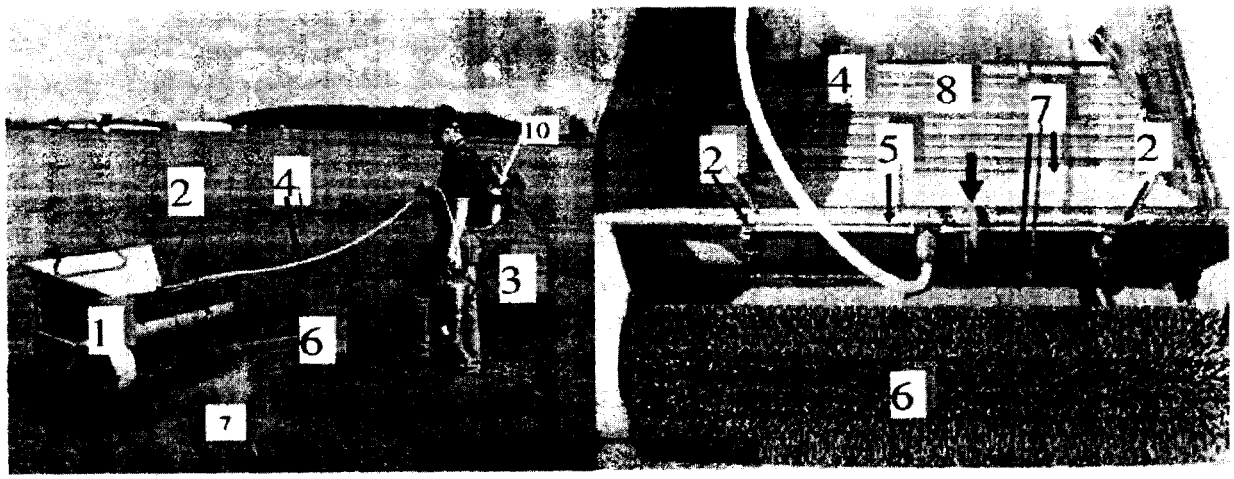

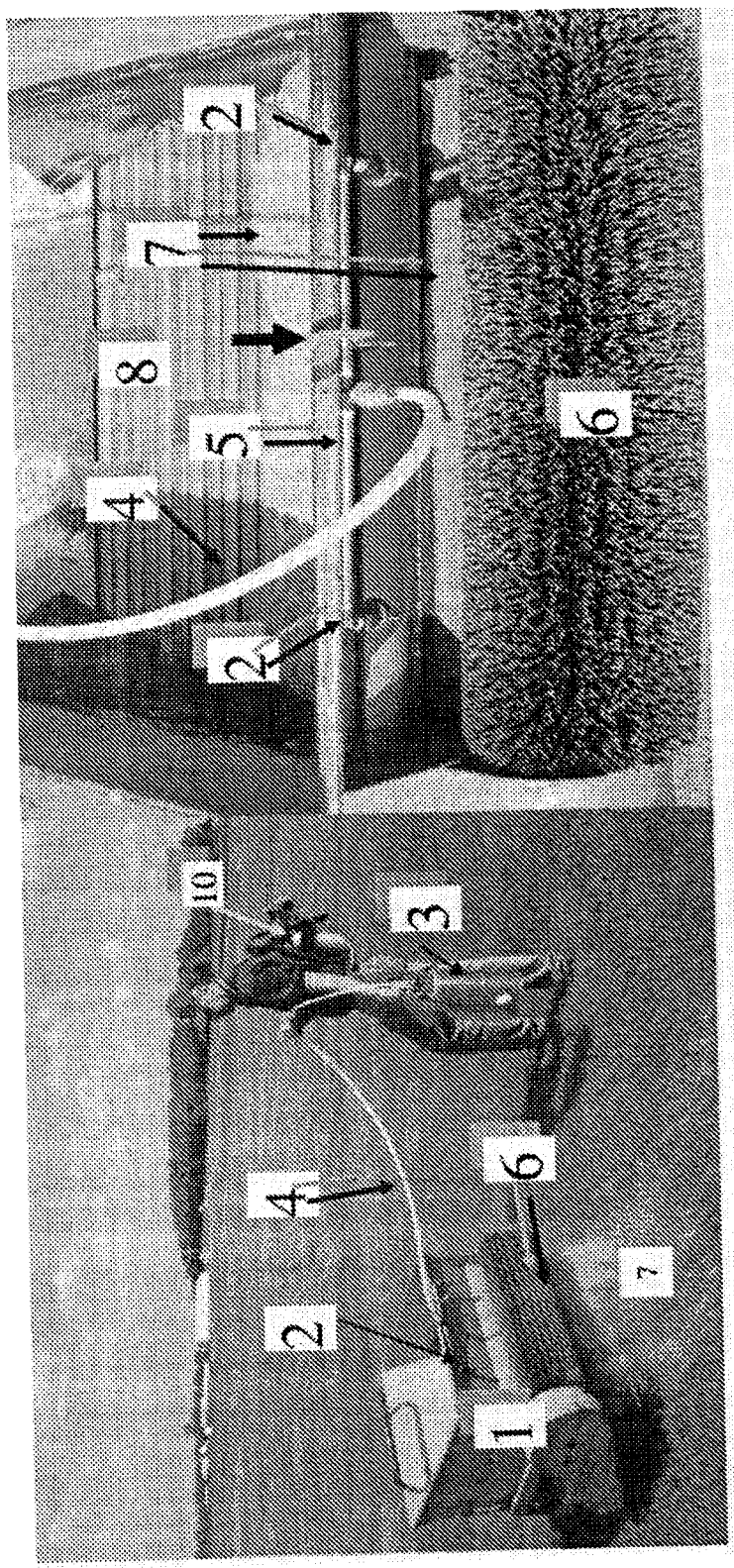

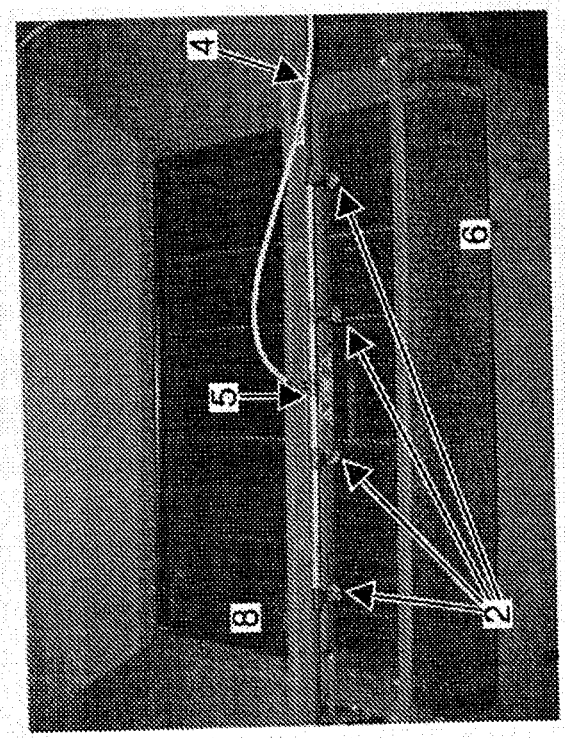
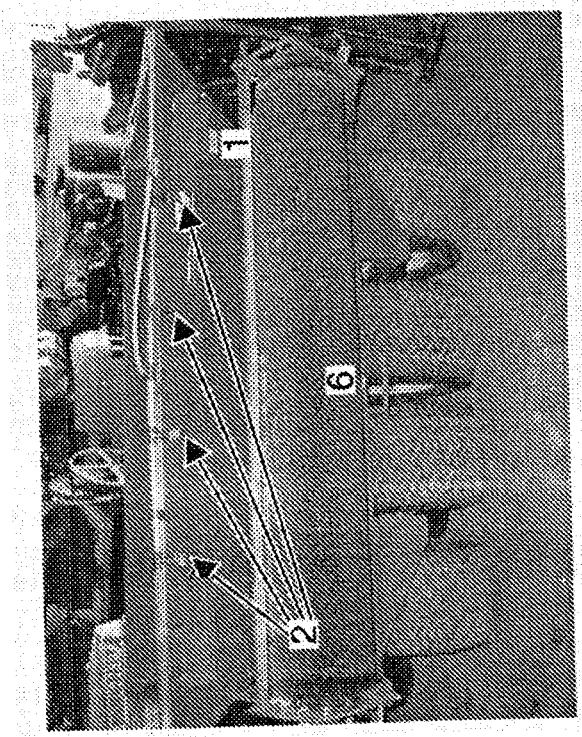
FIG. 5A
FIG. 5B

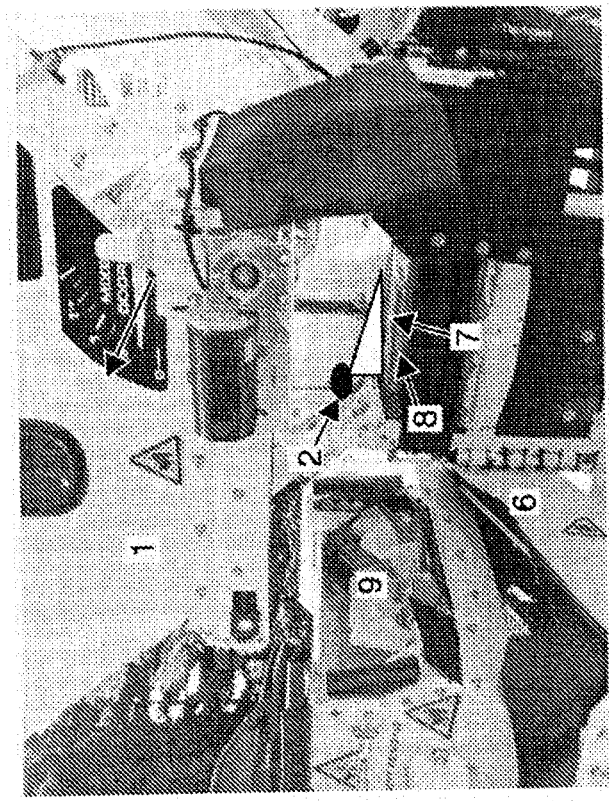
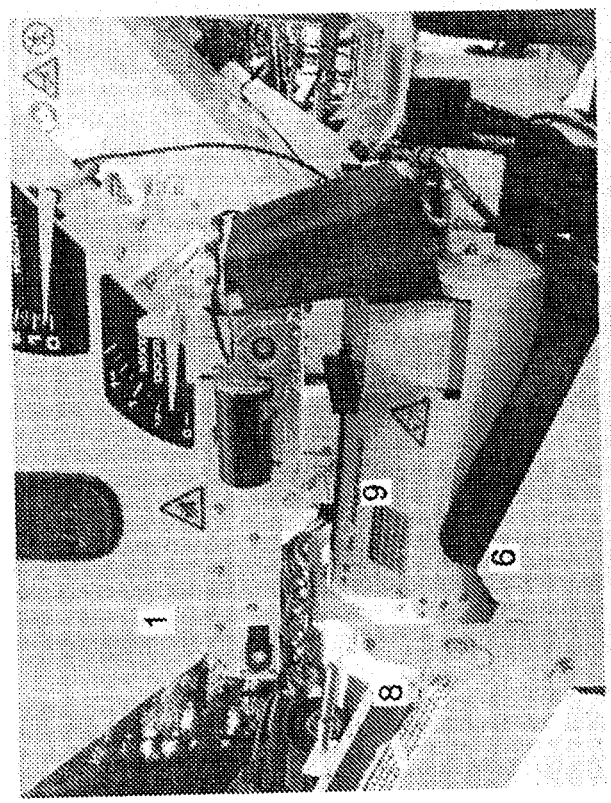
FIG. 9A
FIG. 9B

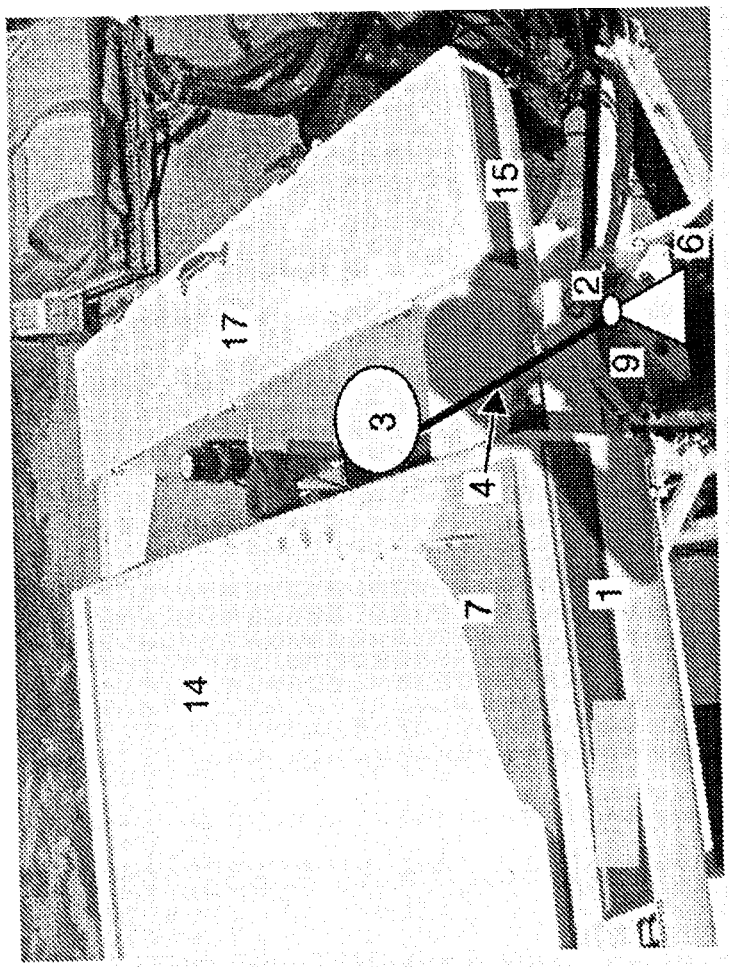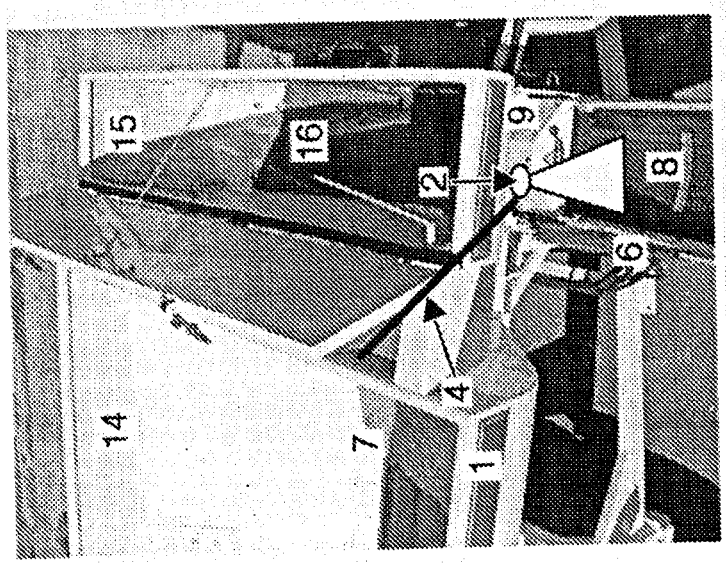

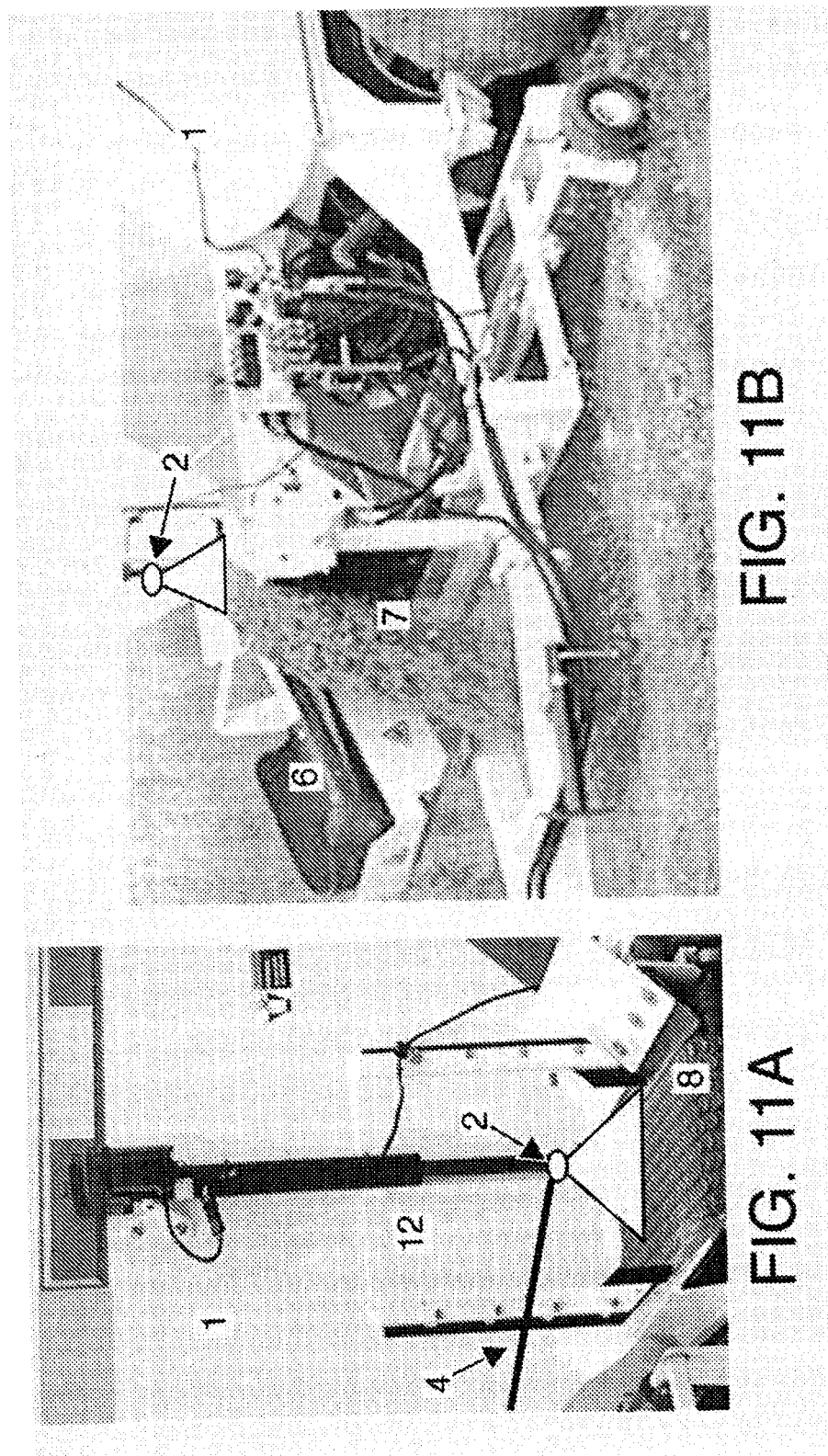

TREATMENT #1

TREATMENT #2

TREATMENT #3

TREATMENT #8

TREATMENT #6

TREATMENT #7

TREATMENT #3

TREATMENT #8